United States Patent
Rabe et al.

(10) Patent No.: US 12,305,210 B2
(45) Date of Patent: May 20, 2025

(54) IN VITRO TRANSCRIPTION TECHNOLOGIES

(71) Applicant: BioNTech SE, Mainz (DE)

(72) Inventors: Irena Rabe, Mainz (DE); Maximilian Buff, Hofheim (DE); Thomas Ziegenhals, Undenheim (DE); Johanna Drögemüller, Weiterstadt (DE); Andreas Kuhn, Mainz (DE); Stephanie Fesser, Mannheim (DE); Rodney Gene Combs, Wildwood, MO (US); Nicole Star Eschmann, St Peters, MO (US); Jennifer Ann Schoborg Romine, St. Louis, MO (US); Jenna Kathryn Williamson, Chesterfield, MO (US)

(73) Assignee: BioNTech SE, Mainz (DE)

( * ) Notice: Subject to any disclaimer, the term of this patent is extended or adjusted under 35 U.S.C. 154(b) by 0 days.

(21) Appl. No.: 17/893,742

(22) Filed: Aug. 23, 2022

(65) Prior Publication Data

US 2023/0183769 A1    Jun. 15, 2023

Related U.S. Application Data

(60) Provisional application No. 63/236,660, filed on Aug. 24, 2021.

(30) Foreign Application Priority Data

Sep. 1, 2021   (WO) ................. PCT/EP2021/074139

(51) Int. Cl.
  *C12P 19/34*   (2006.01)
  *C12N 9/12*    (2006.01)

(52) U.S. Cl.
  CPC ............ *C12P 19/34* (2013.01); *C12N 9/1247* (2013.01)

(58) Field of Classification Search
  CPC .... C12N 2330/30; C12N 9/1247; C12P 19/34
  See application file for complete search history.

(56) References Cited

U.S. PATENT DOCUMENTS

| | | | |
|---|---|---|---|
| 7,074,596 | B2 | 7/2006 | Darzynkiewicz et al. |
| 9,334,328 | B2 | 5/2016 | Schrum et al. |
| 11,135,312 | B2 | 10/2021 | Von Der Mülbe et al. |
| 2008/0171711 | A1 | 7/2008 | Hoerr et al. |

(Continued)

FOREIGN PATENT DOCUMENTS

| | | |
|---|---|---|
| EP | 3155129 A1 | 4/2017 |
| WO | WO-1995/08626 A1 | 3/1995 |
| WO | WO-99/020774 A2 | 4/1999 |

(Continued)

OTHER PUBLICATIONS

Baiersdörfer, M. et al., A Facile Method for the Removal of dsRNA Contaminant from In Vitro-Transcribed mRNA, Molecular Therapy: Nucleic Acids, 15:26-35 (2019).

(Continued)

*Primary Examiner* — Terra C Gibbs
(74) *Attorney, Agent, or Firm* — Choate, Hall & Stewart LLP; Brenda Herschbach Jarrell; Beejan Asady

(57) ABSTRACT

The present disclosure provides technologies for in vitro transcription reactions, particularly for production of pharmaceutical grade RNA, and in some embodiments for large scale production.

18 Claims, 20 Drawing Sheets

Specification includes a Sequence Listing.

| | Linearized plasmid template for modRNA |
|---|---|
| Cap | 1.5 mM CleanCap |
| NTP starting concentrations | 9 mM ATP and CTP<br>0.5 mM GTP and 0.5 mM m1ΨTP |
| Buffer | 40 mM HEPES<br>40 mM Magnesium acetate<br>10 mM DTT<br>2 mM Spermidine |
| DNA Template (linearized Plasmid) | 0.1 μg/μL |
| Ribolock | 0.05 U/μL |
| Pyrophosphatase | 0.1 mU/μL |
| T7-Polymerase | 16 U/μL |
| Fedbatch additions / Interval | 11x 0.77 mM GTP and m1ΨTP / 6:15 min |
| Reaction time | 75+30 min |
| Temperature | 37 °C |
| DNaseI addition | 4 U/μg, 0.1 mM CaCl$_2$ |
| Time DNaseI step | 30-40 min |
| Temperature DNaseI step | 37 °C |
| EDTA addition | 63 mM |

(56) References Cited

U.S. PATENT DOCUMENTS

| | | |
|---|---|---|
| 2012/0213818 A1 | 8/2012 | Hoerr et al. |
| 2024/0110214 A1 | 4/2024 | Ziegenhals et al. |

FOREIGN PATENT DOCUMENTS

| | | | |
|---|---|---|---|
| WO | WO-2008/016473 A2 | 2/2008 | |
| WO | WO-2008/157688 A2 | 12/2008 | |
| WO | WO-2009/149253 A2 | 12/2009 | |
| WO | WO-2010/066418 A1 | 6/2010 | |
| WO | WO-2011/015347 A1 | 2/2011 | |
| WO | WO-2013/059475 A1 | 4/2013 | |
| WO | WO-2013/103146 A1 | 7/2013 | |
| WO | WO-2015/188933 A1 | 12/2015 | |
| WO | WO-2015/199952 A1 | 12/2015 | |
| WO | WO-2016/005324 A1 | 1/2016 | |
| WO | WO-2017/053297 A1 | 3/2017 | |
| WO | WO-2017/060314 A2 | 4/2017 | |
| WO | WO-2017/218573 A1 | 12/2017 | |
| WO | WO-2018/081318 A1 | 5/2018 | |
| WO | WO-2020/185811 A1 | 9/2020 | |
| WO | WO-2021/156267 A1 | 8/2021 | |
| WO | WO-2022/122689 A1 | 6/2022 | |
| WO | WO-2023/025404 A1 | 3/2023 | |

OTHER PUBLICATIONS

Govind, K. and Savithri, H.S., Primer-independent initiation of RNA synthesis by SeMV recombinant RNA-dependent RNA polymerase, Virology, 401:280-292 (2010).

International Search Report for PCT/EP2021/074139, 6 pages (mailed Jun. 9, 2022).

International Search Report for PCT/EP2021/084488, 5 pages (Mar. 25, 2022).

Yin, Y. and Carter, C. W., Incomplete Factorial and Response Surface Methods in Experimental Design: Yield Optimization of tRNATrp from In vitro T7 RNA Polymerase Transcription, Nucleic Acids Research, 24(7):1279-1286 (1996).

Zweerink, H. et al., Synthesis of Reovirus Double-Stranded RNA Within Virionlike Particles, Virology, 50:349-358 (1972).

Berensmeier, Sonja, Magnetic particles for the separation and purification of nucleic acids, Appl Microbiol Biotechnol., 73(3):495-504 (2006).

Holtkamp, S. et al., Modification of antigen-encoding RNA increases stability, translational efficacy, and T-cell stimulatory capacity of dendritic cells, Blood, 108(13):4009-17 (2006).

Kowalska, J. et al., Synthesis and characterization of mRNA cap analogs containing phosphorothioate substitutions that bind tightly to eIF4E and are resistant to the decapping pyrophosphatase DcpS, RNA, 14(6):1119-31 (2008).

Kozak, Marilyn, An analysis of 5'-noncoding sequences from 699 vertebrate messenger RNAs, Nucleic Acids Res., 15(20):8125-48 (1987).

Kuhn, A. et al., Phosphorothioate cap analogs increase stability and translational efficiency of RNA vaccines in immature dendritic cells and induce superior immune responses in vivo, Gene Ther., 17(8):961-71 (2010).

Mu, X. et al., An origin of the immunogenicity of in vitro transcribed RNA, Nucleic Acids Res., 46(10):5239-5249 (2018).

Pasquinelli, A. et al., Reverse 5' caps in RNAs made in vitro by phage RNA polymerases, RNA, 1(9):957-67 (1995).

Peng, Z. et al., Synthesis and application of a chain-terminating dinucleotide mRNA cap analog, Org Lett., 4(2):161-4 (2002).

Stepinski, J. et al., Synthesis and properties of mRNAs containing the novel "anti-reverse" cap analogs 7-methyl(3'-O-methyl)GpppG and 7-methyl (3'-deoxy)GpppG, RNA, 7(10):1486-95 (2001).

Van De Merbel, N.C., Membrane-based sample preparation coupled on-line to chromatography or electrophoresis, J Chromatogr A., 856(1-2):55-82 (1999).

Written Opinion for PCT/EP2021/074139, 7 pages (mailed Jun. 9, 2022).

| | |
|---|---|
| | Linearized plasmid template for modRNA |
| Cap | 1.5 mM CleanCap |
| NTP starting concentrations | 9 mM ATP and CTP<br>0.5 mM GTP and 0.5 mM m1ΨTP |
| Buffer | 40 mM HEPES<br>40 mM Magnesium acetate<br>10 mM DTT<br>2 mM Spermidine |
| DNA Template (linearized Plasmid) | 0.1 µg/µL |
| Ribolock | 0.05 U/µL |
| Pyrophosphatase | 0.1 mU/µL |
| T7-Polymerase | 16 U/µL |
| Fedbatch additions / Interval | 11x 0.77 mM GTP and m1ΨTP / 6-15 min |
| Reaction time | 75 + 30 min |
| Temperature | 37 °C |
| DNaseI addition | 4 U/µg, 0.1 mM CaCl2 |
| Time DNaseI step | 30-40 min |
| Temperature DNaseI step | 37 °C |
| EDTA addition | 63 mM |

FIG. 1

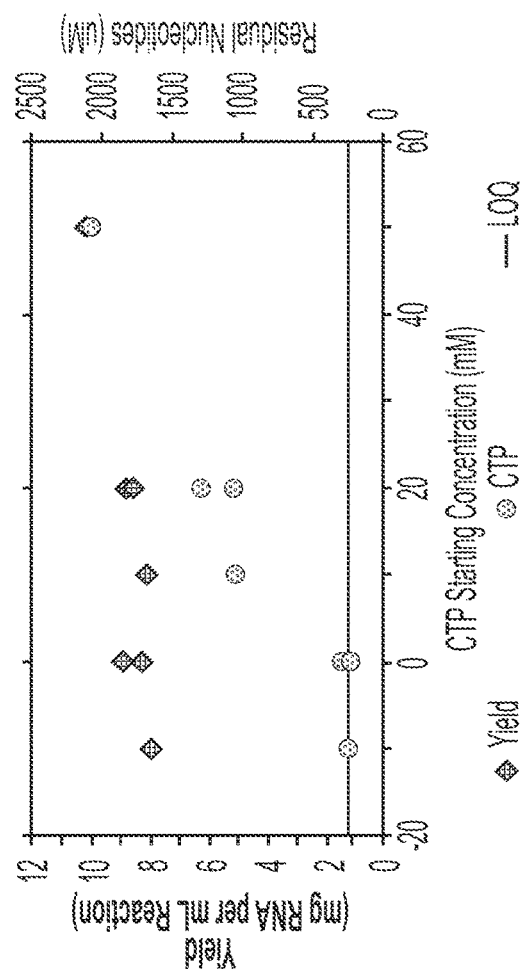
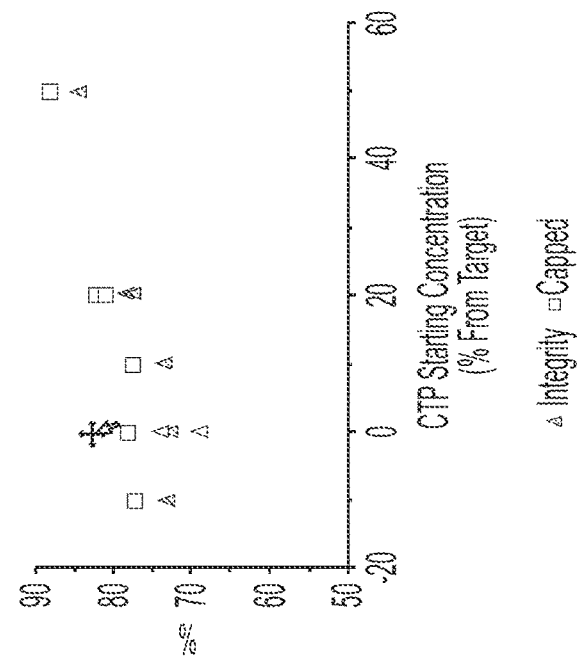
FIG. 6

| RXN-ID | DNA-Template | CTP amount in IVT | RNA yield [µg/µL] | Integrity BA [%] | dsRNA content [pg dsRNA/µg RNA] | Residual DNA [ng DNA/mg RNA] |
|---|---|---|---|---|---|---|
| 1 | Construct X | Control (+0% CTP)/Standard | 8.3 | 76 | 124 | 6.71 |
| 2 | | | 8.2 | 76 | 101 | 16.12 |
| 3 | | +10% CTP | 8.2 | 78 | 121 | n.a |
| 4 | | | 8.7 | 78 | 71 | n.a |
| 5 | | +20% CTP | 8.3 | 78 | 35 | 36.95 |
| 6 | | | 9.0 | 79 | 46 | 58.49 |
| 7 | | +50% CTP | 9.2 | 81 | 16 | 30.97 |
| 8 | | | 9.7 | 80 | 14 | 26.16 |

FIG. 16

| RXN-ID | DNA-Template | NTP amount in IVT | RNA yield [µg/µL] | Integrity BA [%] | Integrity FA [%] (without baseline correction) | dsRNA content [pg dsRNA/µg RNA] | Residual DNA [ng DNA/mg RNA] |
|---|---|---|---|---|---|---|---|
| 1 | Construct X | Standard-Process | 8.43 | 70 | 76.3 | < 0 | 0.30 |
| 2 | | Standard-Process | 8.55 | 71 | 76.4 | < 0 | 1.42 |
| 3 | | + 50% CTP, 20% ATP | 10.97 | 79 | 84.0 | < 0 | 1.84 |
| 4 | | + 50% CTP, 20% ATP | 10.34 | 78 | 82.5 | < 0 | 10.29 |
| 5 | | + 50% CTP | 10.20 | 80 | 83.3 | 6 | 14.53/15.30 |
| 6 | | + 50% CTP | 10.02 | 79 | 83.2 | 5 | 8.23 |
| 7 | | + 20% ATP | 8.33 | 76 | 79.3 | < 0 | <15* |
| 8 | | + 20% ATP | 8.27 | 74 | 80.9 | < 0 | 30.34 |

*only measured one dilution

FIG. 18

| RXN-ID | DNA-Template | ATP/CTP Range in % | NTP concentration in mM (ATP/CTP) | NTPs total conc. | trx-yield [μg/μL] | Integrity [%] | [pg dsRNA/ μg RNA] /SD |
|---|---|---|---|---|---|---|---|
| 1 | Construct X | Standard | 10.8/13.5 | 42.3 | 10.12 | 84 | 122 (SD: 8) |
| 2 | | Standard | 10.8/13.5 | 42.3 | 9.50 | 86 | #DIV/0! |
| 3 | | ATP +25% / CTP +7% | 13.5/14.4 | 45.9 | 8.66 | 86 | 48 (SD: 5) |
| 4 | | ATP +25% / CTP +7% | 13.5/14.4 | 45.9 | 8.61 | 86 | 64 (SD: 3) |
| 5 | | ATP -21% / CTP -37% | 8.5/8.5 | 35 | 7.01 | 86 | 145 (SD: 18) |
| 6 | | ATP -21% / CTP -37% | 8.5/8.5 | 35 | 7.37 | 86 | 35 (SD: 5) |
| 7 | | ATP +25% | 13.5/13.5 | 45 | 8.96 | 88 | 81 (SD: 9) |
| 8 | | ATP +25% | 13.5/13.5 | 45 | 8.28 | 85 | n.a. |
| 9 | | CTP +7% | 10.8/14.4 | 43.2 | 6.60 | 84 | 193 (SD: 13) |
| 10 | | CTP +7% | 10.8/14.4 | 43.2 | 6.48 | 84 | n.a. |

FIG. 20

SEQUENCE LISTING

```
Sequence total quantity: 25
SEQ ID NO: 1             moltype = AA  length = 27
FEATURE                  Location/Qualifiers
source                   1..27
                         mol_type = protein
                         organism = Human alphaherpesvirus 1
SEQUENCE: 1
MGGAAARLGA VILFVVIVGL HGVRSKY                                          27

SEQ ID NO: 2             moltype = AA  length = 25
FEATURE                  Location/Qualifiers
source                   1..25
                         mol_type = protein
                         organism = Human alphaherpesvirus 2
SEQUENCE: 2
MGRLTSGVGT AALLVVAVGL RVVCA                                            25

SEQ ID NO: 3             moltype = AA  length = 28
FEATURE                  Location/Qualifiers
source                   1..28
                         mol_type = protein
                         organism = Human alphaherpesvirus 2
SEQUENCE: 3
MGRLTSGVGT AALLVVAVGL RVVCAKYA                                         28

SEQ ID NO: 4             moltype = AA  length = 19
FEATURE                  Location/Qualifiers
source                   1..19
                         mol_type = protein
```

```
                        organism = Severe acute respiratory syndrome coronavirus 2
SEQUENCE: 4
MFVFLVLLPL VSSQCVNLT                                                    19

SEQ ID NO: 5            moltype = AA  length = 21
FEATURE                 Location/Qualifiers
source                  1..21
                        mol_type = protein
                        organism = Homo sapiens
SEQUENCE: 5
MDWIWRILFL VGAATGAHSQ M                                                 21

SEQ ID NO: 6            moltype = AA  length = 20
FEATURE                 Location/Qualifiers
source                  1..20
                        mol_type = protein
                        organism = Homo sapiens
SEQUENCE: 6
METPAQLLFL LLLWLPDTTG                                                   20

SEQ ID NO: 7            moltype = AA  length = 18
FEATURE                 Location/Qualifiers
source                  1..18
                        mol_type = protein
                        organism = unidentified
SEQUENCE: 7
MDWTWILFLV AAATRVHS                                                     18

SEQ ID NO: 8            moltype = AA  length = 24
FEATURE                 Location/Qualifiers
source                  1..24
                        mol_type = protein
                        organism = Japanese encephalitis virus
SEQUENCE: 8
MLGSNSGQRV VFTILLLLVA PAYS                                              24

SEQ ID NO: 9            moltype = AA  length = 17
FEATURE                 Location/Qualifiers
source                  1..17
                        mol_type = protein
                        organism = Indiana vesiculovirus
SEQUENCE: 9
MKCLLYLAFL FIGVNCA                                                      17

SEQ ID NO: 10           moltype = AA  length = 18
FEATURE                 Location/Qualifiers
source                  1..18
                        mol_type = protein
                        organism = unidentified
SEQUENCE: 10
MDWTWILFLV AAATRVHS                                                     18

SEQ ID NO: 11           moltype = AA  length = 19
FEATURE                 Location/Qualifiers
source                  1..19
                        mol_type = protein
                        organism = Homo sapiens
SEQUENCE: 11
ETPAQLLFLL LLWLPDTTG                                                    19

SEQ ID NO: 12           moltype = AA  length = 24
FEATURE                 Location/Qualifiers
source                  1..24
                        mol_type = protein
                        organism = Japanese encephalitis virus
SEQUENCE: 12
MLGSNSGQRV VFTILLLLVA PAYS                                              24

SEQ ID NO: 13           moltype = AA  length = 17
FEATURE                 Location/Qualifiers
source                  1..17
                        mol_type = protein
                        organism = Indiana vesiculovirus
SEQUENCE: 13
MKCLLYLAFL FIGVNCA                                                      17

SEQ ID NO: 14           moltype = AA  length = 15
FEATURE                 Location/Qualifiers
source                  1..15
```

```
                        mol_type = protein
                        organism = unidentified
SEQUENCE: 14
MWLVSLAIVT ACAGA                                                         15

SEQ ID NO: 15           moltype = AA  length = 15
FEATURE                 Location/Qualifiers
source                  1..15
                        mol_type = protein
                        organism = Severe acute respiratory syndrome coronavirus 2
SEQUENCE: 15
MFVFLVLLPL VSSQC                                                         15

SEQ ID NO: 16           moltype = DNA  length = 81
FEATURE                 Location/Qualifiers
source                  1..81
                        mol_type = genomic DNA
                        organism = Human alphaherpesvirus 1
SEQUENCE: 16
atggggggg ctgccgccag gttgggggcc gtgattttgt tgtcgtcat agtgggcctc          60
catgggtcc gcagcaaata t                                                   81

SEQ ID NO: 17           moltype = DNA  length = 81
FEATURE                 Location/Qualifiers
source                  1..81
                        mol_type = other DNA
                        organism = synthetic construct
SEQUENCE: 17
atgggaggag ccgccgccag actgggagcc gtgatcctgt cgtggtgat cgtgggactg         60
catggagtga gaagcaagta c                                                  81

SEQ ID NO: 18           moltype = DNA  length = 57
FEATURE                 Location/Qualifiers
source                  1..57
                        mol_type = genomic DNA
                        organism = Severe acute respiratory syndrome coronavirus 2
SEQUENCE: 18
atgtttgtgt tcttgtgct gctgcctctt gtgtcttctc agtgtgtgaa tttgaca           57

SEQ ID NO: 19           moltype = DNA  length = 63
FEATURE                 Location/Qualifiers
source                  1..63
                        mol_type = genomic DNA
                        organism = Homo sapiens
SEQUENCE: 19
atggattgga tttggagaat cctgttcctc gtgggagccg ctacaggagc ccactcccag        60
atg                                                                      63

SEQ ID NO: 20           moltype = RNA  length = 278
FEATURE                 Location/Qualifiers
source                  1..278
                        mol_type = other RNA
                        organism = synthetic construct
SEQUENCE: 20
ctggtactgc atgcacgcaa tgctagctgc ccctttcccg tcctgggtac cccgagtctc        60
ccccgacctc gggtcccagg tatgctccca cctccacctg ccccactcac cacctctgct      120
agttccagac acctcccaag cacgcagcaa tgcagctcaa aacgcttagc ctagccacac      180
ccccacggga aacagcagtg attaacctt agcaataaac gaaagtttaa ctaagctata      240
ctaaccccag ggttggtcaa tttcgtgcca gccacacc                              278

SEQ ID NO: 21           moltype = RNA  length = 57
FEATURE                 Location/Qualifiers
source                  1..57
                        mol_type = other RNA
                        organism = synthetic construct
SEQUENCE: 21
gggaaataag agagaaaaga agagtaagaa gaaatataag accccggcgc cgccacc           57

SEQ ID NO: 22           moltype = RNA  length = 47
FEATURE                 Location/Qualifiers
source                  1..47
                        mol_type = other RNA
                        organism = synthetic construct
SEQUENCE: 22
gggaaataag agagaaaaga agagtaagaa gaaatataag agccacc                      47

SEQ ID NO: 23           moltype = RNA  length = 11
FEATURE                 Location/Qualifiers
source                  1..11
```

```
                        mol_type = other RNA
                        organism = synthetic construct
SEQUENCE: 23
gggatcctac c                                                            11

SEQ ID NO: 24           moltype = RNA  length = 119
FEATURE                 Location/Qualifiers
source                  1..119
                        mol_type = other RNA
                        organism = synthetic construct
SEQUENCE: 24
tgataatagg ctggagcctc ggtggcctag cttcttgccc cttgggcctc cccccagccc       60
ctcctcccct tcctgcaccc gtaccccgt ggtctttgaa taaagtctga gtgggcggc        119

SEQ ID NO: 25           moltype = RNA  length = 119
FEATURE                 Location/Qualifiers
source                  1..119
                        mol_type = other RNA
                        organism = synthetic construct
SEQUENCE: 25
tgataatagg ctggagcctc ggtggccatg cttcttgccc cttgggcctc cccccagccc       60
ctcctcccct tcctgcaccc gtaccccgt ggtctttgaa taaagtctga gtgggcggc        119
```

IN VITRO TRANSCRIPTION TECHNOLOGIES

SEQUENCE LISTING

The instant application contains a Sequence Listing which has been submitted electronically in XML format and is hereby incorporated by reference in its entirety. Said XML copy, created on Jan. 3, 2023, is named 2013237-0391_SL.xml and is 23,740 bytes in size.

BACKGROUND

Particularly in light of its increasing importance as a therapeutic modality, technologies for manufacturing RNA are important and valuable.

SUMMARY

The present disclosure provides certain insights relating to technologies for manufacturing RNA, particularly therapeutic RNA (e.g., therapeutic mRNA). In some embodiments, provided technologies are particularly useful, and/or offer surprising benefits and/or advantages, when used for large scale production, e.g., of therapeutic grade RNA.

For example, the present disclosure provides insights regarding particularly useful concentrations of cytidine triphosphate (CTP) and/or adenosine triphosphate (ATP) in in vitro transcription (IVT) reaction mixtures (e.g., in initial reaction mixtures, it being understood by those skilled in the art that NTPs are utilized during the reaction, so that their concentrations decrease over time unless supplemented).

In some embodiments, the present disclosure provides technologies that improve one or more of RNA yield, RNA integrity, RNA capping level and/or efficiency; alternatively or additionally, in some embodiments, the present disclosure provides technologies that reduce levels of one or more contaminants or aberrant products (e.g., dsRNA).

In some embodiments, the present disclosure provides IVT reaction conditions (e.g., nucleotide concentrations in reaction mixtures) that are useful independent of sequence of the RNA transcript generated in the reaction.

The present disclosure encompasses the recognition of a problem with production of RNA by IVT, in particular at large-scale (e.g., commercial scale). Among other things, the present disclosure identifies that RNA transcribed in vitro can be challenging to produce with high yield and/or integrity, and/or with low level of aberrant products (e.g., double-stranded RNA (dsRNA)). The present disclosure particularly appreciates that such challenges can be particularly acute when producing therapeutic (e.g., for administration to animal(s), and particularly to humans) RNA (e.g., mRNA), especially at a commercial scale (e.g., 0.1-10 g, 10-500 g, 500 g-1 kg, 750 g-1.5 kg; those skilled in the art will appreciate that different products may be manufactured at different scales, e.g., depending on patient population size) and/or at pharmaceutical quality (which can typically be more challenging to achieve, for example, at larger scales, for example because contaminants and/or integrity issues may be more pronounced at such scales).

In some embodiments, provided technologies may be useful when applied to production of transcripts with relatively high C and/or A content (e.g., relative to G and/or U content in the transcript). However, in some embodiments, the present disclosure provides a surprising insight that provided reaction conditions (e.g., levels [e.g., absolute and/or relative levels] of CTP and/or ATP [or analogs thereof] in reaction mixtures) may be useful independent of transcript sequence.

In some embodiments, elevated CTP and/or ATP as described herein improves yield and/or integrity and/or capping, and/or lowers production of one or more aberrant products (e.g., dsRNA); in some embodiments, independently of the percent and/or molar ratio of nucleotides (e.g., nucleotide content) in the produced RNA.

In some embodiments, technologies provided herein are particularly useful for manufacturing RNA at commercial quality and/or in commercial scale. Those skilled in the art will be aware that different therapeutic RNAs are utilized at very different scales. For example, subject-specific RNAs have been described and are used in individualized cancer vaccines (see, e.g., RO7198457); these need only be manufactured on a scale sufficient to treat the relevant individual. By contrast, RNAs developed for other purposes, e.g., as general cancer vaccines, as infectious agent vaccines, as vectors for expression of antibodies, enzymes, cytokines, etc., may typically be manufactured on larger scale(s). Therapeutic RNA has proven to be particularly valuable in the recent SARS-CoV-2 pandemic, which required manufacturing at unprecedented scales. Technologies provided herein, in various embodiments, may be utilized at each of these scales. Thus for example, in some embodiments, technologies described herein are useful to produce RNAs (e.g., at a manufacturing scale) within a range of about 0.01 g/hr RNA to about 1 g/hr RNA, 1 g/hr RNA to about 100 g/hr RNA, about 1 g RNA/hr to about 20 g RNA/hr, or about 100 g RNA/hr to about 10,000 g RNA/hr). In some embodiments, technologies described herein are utilized in reactions that produce tens or hundreds of milligrams to tens or hundreds of grams (or more) of RNA per batch. Those skilled in the art, reading the present disclosure, will appreciate that certain benefits achieved (e.g., improved integrity and/or yield) may be particularly advantageous in the context of pharmaceutical grade manufacturing and/or particularly at large scale as described herein.

In some embodiments, technologies described herein can be utilized in parallel, for example to further improve throughput capacity.

In some particular embodiments, provided technologies may be useful for manufacturing RNA preparations (e.g., RNA drug substance) in a batch size of at least 0.01 g, 0.02 g, 0.03 g, 0.04 g, 0.05 g, 0.06 g, 0.07 g, 0.08 g, 0.09 g, 0.1 g, 0.5 g, 1 g, 2 g, 3 g, 4 g, 5 g, 6 g, 7 g, 8 g, 9 g, 10 g RNA (including, e.g., at least 15 g RNA, at least 20 g RNA, at least 25 g RNA, at least 30 g RNA, at least 35 g RNA, at least 40 g RNA, at least 45 g RNA, at least 50 g RNA, at least 55 g RNA, at least 60 g RNA, at least 70 g RNA, at least 80 g RNA, at least 90 g RNA, at least 100 g RNA, at least 150 g RNA, at least 200 g RNA, at least 300 g RNA, at least 400 g RNA, at least 500 g RNA, at least 750 g, at least 1 kg, at least 1.1 kg, at least 1.2 kg, at least 1.3 kg, at least 1.4 kg, at least 1.5 kg or more). In some embodiments, technologies provided herein can be used to produce batch sizes within a range of about 0.01 g to about 500 g RNA, about 0.01 g to about 10 g RNA, about 1 g to about 10 g RNA, about 10 g to about 500 g RNA, about 10 g to about 300 g RNA, about 10 g to about 200 g RNA or about 30 g to about 60 g RNA.

In some embodiments, technologies provided herein are useful for large scale manufacturing that produces a mass throughput of at least 1.5 g RNA per hour (including, e.g., at least 2 g RNA per hour, at least 2.5 g RNA per hour, at least 3 g RNA per hour, at least 3.5 g RNA per hour, at least 4 g RNA per hour, at least 4.5 g RNA per hour, at least 5 g RNA per hour, at least 5.5 g RNA per hour, at least 6 g RNA per hour, at least 6.5 g RNA per hour, at least 7 g RNA per hour, at least 7.5 g RNA per hour, at least 8 g RNA per hour, at least 8.5 g RNA per hour, at least 9 g RNA per hour, at least 10 g RNA per hour or higher). In some embodiments, large scale manufacture methods described herein can reach a capacity of 15 g RNA per hour to 20 g RNA per hour (e.g., about 17 g per hour).

Indeed, in some embodiments, provided technologies offer a surprising advantage that they are useful at a variety of scales and/or specifically at very large manufacturing scales (e.g., above about 10s or even 100s of grams/batch), and/or are useful (e.g., even at such very large scales) substantially independent of RNA sequence (e.g., for production of RNAs with various C and/or A content)

In some aspects, the present disclosure provides methods of producing a ribonucleic acid (RNA) molecule through in vitro transcription, the method comprising creating a reaction mixture under reaction conditions to form the RNA molecule, the reaction mixture comprising a nucleic acid polymerase, a nucleic acid template, and: a molar ratio a of total cytidine triphosphate (CTP) and/or one or more functional CTP analog(s) to total guanosine triphosphate (GTP) and/or one or more functional GTP analog(s); and/or a molar ratio b of total CTP and/or one or more functional CTP analog(s) to total uridine triphosphate (UTP) and/or one or more functional UTP analog(s); and/or a molar ratio c of total CTP and/or one or more functional CTP analog(s) to total adenosine triphosphate (ATP) and/or one or more functional ATP analog(s), wherein the RNA molecule comprises: a molar ratio x of total cytidine and/or one or more functional cytidine analog(s) to total guanosine and/or one or more functional guanosine analog(s); and/or a molar ratio y of total cytidine and/or one or more functional cytidine analog(s) to total uridine and/or one or more functional uridine analog(s); and/or a molar ratio z of total cytidine and/or one or more functional cytidine analog(s) to total adenosine and/or one or more functional adenosine analog(s), and wherein: a is at least 1.25, and/or a is at least about 1.10-fold greater than x; and/or b is at least 1.25, and/or b is at least about 1.10-fold greater than y; and/or c is at least 1.10, and/or c is at least about 1.10-fold greater than z.

In some embodiments, a is at least 1.30, 1.35, 1.40, 1.45, 1.50, 1.55, 1.60, 1.65, 1.70, 1.75, or 1.8. In some embodiments, a is at least 1.5. In some embodiments, a is at least about 1.15-fold, 1.20-fold, 1.25-fold, 1.30-fold, 1.35-fold, 1.40-fold, 1.45-fold, 1.50-fold, 1.55-fold, 1.60-fold, 1.65-fold, 1.70-fold, or 1.75-fold greater than x. In some embodiments, a is at least about 1.15-fold greater than x. In some embodiments, a is at least about 1.20-fold greater than x.

In some embodiments, b is at least 1.30, 1.35, 1.40, 1.45, 1.50, 1.55, 1.60, 1.65, 1.70, 1.75, or 1.8. In some embodiments, b is at least 1.5. In some embodiments, b is at least about 1.15-fold, 1.20-fold, 1.25-fold, 1.30-fold, 1.35-fold, 1.40-fold, 1.45-fold, 1.50-fold, 1.55-fold, 1.60-fold, 1.65-fold, 1.70-fold, or 1.75-fold greater than y. In some embodiments, b is at least about 1.15-fold greater than y. In some embodiments, b is at least about 1.20-fold greater than y.

In some embodiments, c is at least 1.15, 1.20, 1.25, 1.30, 1.35, 1.40, 1.45, or 1.50. In some embodiments, c is at least 1.25. In some embodiments, c is at least about 1.15-fold, 1.20-fold, 1.25-fold, 1.30-fold, 1.35-fold, 1.40-fold, 1.45-fold, 1.50-fold, 1.55-fold, 1.60-fold, 1.65-fold, 1.70-fold, or 1.75-fold greater than z. In some embodiments, c is at least about 1.15-fold greater than z. In some embodiments, c is at least about 1.20-fold greater than z.

In some embodiments, the present disclosure provides methods further comprising combining into the reaction mixture: a molar ratio d of total ATP and/or one or more functional ATP analog(s) to total GTP and/or one or more functional GTP analog(s); and/or a molar ratio e of total ATP and/or one or more functional ATP analog(s) to total UTP and/or one or more functional UTP analog(s), wherein the RNA molecule further comprises: a molar ratio v of total adenosine and/or one or more functional adenosine analog(s) to total guanosine and/or one or more functional guanosine analog(s); and/or a molar ratio w of total adenosine and/or one or more functional adenosine analog(s) to total uridine and/or one or more functional uridine analog(s), and wherein: d is at least 1.10, and/or d is at least about 1.05-fold greater than v; and/or e is at least 1.10, and/or e is at least about 1.05-fold greater than w. In some such embodiments, d is at least 1.15, 1.20, 1.25, 1.30, 1.35, 1.40, 1.45, or 1.50. In some such embodiments, d is at least 1.20. In some such embodiments, d is at least about 1.10-fold, 1.15-fold, 1.20-fold, 1.25-fold, 1.30-fold, 1.35-fold, 1.40-fold, 1.45-fold, or 1.50-fold greater than v. In some such embodiments, d is at least about 1.10-fold greater than v. In some such embodiments, d is at least about 1.20-fold greater than v. In some such embodiments, e is at least 1.15, 1.20, 1.25, 1.30, 1.35, 1.40, 1.45, or 1.50. In some such embodiments, e is at least 1.20. In some such embodiments, e is at least about 1.10-fold, 1.15-fold, 1.20-fold, 1.25-fold, 1.30-fold, 1.35-fold, 1.40-fold, 1.45-fold, or 1.50-fold greater than w. In some such embodiments, e is at least about 1.10-fold greater than w. In some such embodiments, e is at least about 1.20-fold greater than w.

In some embodiments, a portion of the total CTP and/or one or more functional CTP analog(s) is added to the reaction mixture before transcription begins and/or at a start of transcription and a remaining portion of the total CTP and/or one or more functional CTP analog(s) is added to the reaction mixture after the start of transcription.

In some embodiments, all of the total CTP and/or one or more functional CTP analog(s) is added to the reaction mixture before transcription begins and/or at a start of transcription.

In some embodiments, a portion of the total GTP and/or one or more functional GTP analog(s) is added to the reaction mixture before transcription begins and/or at a start of transcription and a remaining portion of the total GTP and/or one or more functional GTP analog(s) is added to the reaction mixture after the start of transcription.

In some embodiments, all of the total GTP and/or one or more functional GTP analog(s) is added to the reaction mixture before transcription begins and/or at a start of transcription.

In some embodiments, a portion of the total UTP and/or one or more functional UTP analog(s) is added to the reaction mixture before transcription begins and/or at a start of transcription and a remaining portion of the total UTP and/or one or more functional UTP analog(s) is added to the reaction mixture after the start of transcription.

In some embodiments, all of the total UTP and/or one or more functional UTP analog(s) is added to the reaction mixture before transcription begins and/or at a start of transcription.

In some embodiments, a portion of the total ATP and/or one or more functional ATP analog(s) is added to the reaction mixture before transcription begins and/or at a start of transcription and a remaining portion of the total ATP and/or one or more functional ATP analog(s) is added to the reaction mixture after the start of transcription.

In some embodiments, all of the total ATP and/or one or more functional ATP analog(s) is added to the reaction mixture before transcription begins and/or at a start of transcription.

In some embodiments, the RNA molecule is single-stranded. In some embodiments, the RNA molecule is linear RNA, messenger RNA, and/or nucleoside-modified messenger RNA.

In some embodiments, a nucleic acid template is a DNA template. In some embodiments, a template is a linear template (e.g., a linear DNA template). In some embodiments, a template is a plasmid (e.g., a DNA plasmid). In some embodiments, a template is an amplicon (e.g., as generated by polymerase chain reaction).

In some embodiments, a reaction mixture comprises a nucleic acid template at a concentration of 0.01-2 µg/µL.

In some embodiments, a nucleic acid polymerase is an RNA polymerase. In some embodiments, a nucleic acid polymerase is a T7 RNA polymerase, a T3 RNA polymerase, a SP6 RNA polymerase, a N4 virion RNA polymerase, or a variant or functional domain thereof.

In some embodiments, a reaction mixture comprises (e.g., further comprises) one or more of a reaction buffer, an RNase inhibitor, a pyrophosphatase, one or more salts, a reducing agent, and spermidine. In some embodiments, the reaction buffer comprises HEPES, Tris-HCl, or PBS. In some embodiments, the reaction mixture comprises the reaction buffer at a concentration of 20-60 mM or 100-150 mM. In some embodiments, a reaction buffer has a pH of 7-9. In some embodiments, the reaction mixture comprises an RNase inhibitor at a concentration of 0.01-0.1 U/µL. In some embodiments, one unit (U) of an RNase inhibitor inhibits the activity of 5 ng of RNase A by at least 50%. In some embodiments, the pyrophosphatase is an inorganic pyrophosphatase. In some embodiments, the reaction mixture comprises the pyrophosphatase at a concentration of 0.01-0.2 mU/µL. In some embodiments, one or more salts included in a reaction mixture comprise one or more magnesium salts and/or one or more calcium salts. In some embodiments, one or more magnesium salts comprises magnesium acetate or magnesium chloride. In some embodiments, a reaction mixture comprises one or more salts at a concentration of 20-60 mM. In some embodiments, a reaction mixture comprises one or more salts at a concentration of 100-150 mM. In some embodiments, a reducing agent comprises dithithreitol or 2-mercaptoethanol. In some embodiments, a reaction mixture comprises a reducing agent at a concentration of 5-15 mM. In some embodiments, a reaction mixture comprises a sperimidine at a concentration of 0.5-3 mM.

In some embodiments, in vitro transcription is performed for at least 20-180 minutes. In some embodiments, in vitro transcription is performed at a temperature of 25-55° C.

In some embodiments, methods disclosed herein further comprise digesting the nucleic acid template after in vitro transcription of the RNA molecule. In some such embodiments, the nucleic acid template is digested by a DNase. In some such embodiments, DNase comprises DNase I.

In some embodiments, methods disclosed herein comprise (e.g., further comprise) digesting polypeptides of a IVT reaction mixture (e.g., a nucleic acid polymerase, pyrophosphatase, DNAses such as DNAse I, RNAse inhibitors) after in vitro transcription to produce an RNA molecule. In some such embodiments, the nucleic acid polymerase is digested by a proteinase. In some such embodiments, the proteinase is or comprises proteinase K.

In some embodiments, technologies provided by the present disclosure comprise (e.g., further comprise) performing one or more assessments (e.g., assessments of one or more quality control parameters) of an in vitro transcription reaction and/or of an RNA produced thereby. In some such embodiments, one or more quality control parameters are selected from the group consisting of RNA integrity, RNA concentration, residual double-stranded RNA (dsRNA), and/or capping of the RNA molecule during and/or after transcription. In some such embodiments, RNA integrity is assessed using agarose gel electrophoresis. In some such embodiments, RNA integrity is assessed using capillary gel electrophoresis. In some such embodiments, RNA integrity of RNA molecules produced by the method is at least about 40%, 45%, 50%, 55%, 60%, 65%, 70%, 75%, 80%, 85%, 90%, or 95%.

In some embodiments, RNA integrity of RNA molecule(s) produced in accordance with technologies provided herein is increased at least about 1%, 2%, 3%, 4%, 5%, 6%, 7%, 8%, 9%, 10%, 11%, 12%, 13%, 14%, 15%, 16%, 17%, 18%, 19%, or 20% relative to an appropriate comparator (e.g., an otherwise comparable in vitro transcription reaction, for example utilizing a reaction mixture in which a is not at least 1.25, b is not at least 1.25, and/or c is not at least 1.10). In some embodiments, RNA integrity is increased at least about 1%, 2%, 3%, 4%, 5%, 6%, 7%, 8%, 9%, 10%, 11%, 12%, 13%, 14%, 15%, 16%, 17%, 18%, 19%, or 20% relative to an appropriate comparator (e.g., an otherwise comparable to in vitro transcription reaction, for example utilizing a reaction mixture in which: d is not at least 1.10 and/or e is not at least 1.10; a is not at least 1.25, b is not at least 1.25, c is not at least 1.10, and/or d is not at least 1.10 and/or e is not at least 1.10; a is not at least 1.25, b is not at least 1.25, c is not at least 1.10, and/or d is at least 1.10 and/or e is at least 1.10; and/or a is at least 1.25, b is at least 1.25, and/or c is at least 1.10, and/or d is not at least 1.10 and/or e is not at least 1.10). In some embodiments, RNA integrity is increased at least about 1%, 2%, 3%, 4%, 5%, 6%, 7%, 8%, 9%, 10%, 11%, 12%, 13%, 14%, 15%, 16%, 17%, 18%, 19%, or 20% relative to an appropriate comparator (e.g., an otherwise comparable in vitro transcription reaction, for example utilizing a reaction mixture in which a is not at least about 1.10-fold greater than x, b is not at least about 1.10-fold greater than y, and/or c is not at least about 1.10-fold greater than z). In some embodiments, RNA integrity is increased at least about 1%, 2%, 3%, 4%, 5%, 6%, 7%, 8%, 9%, 10%, 11%, 12%, 13%, 14%, 15%, 16%, 17%, 18%, 19%, or 20% relative to an appropriate comparator (e.g., an otherwise comparable in vitro transcription reaction, for example utilizing a reaction mixture in which: d is not at least about 1.05-fold greater than v and/or e is not at least about 1.05-fold greater than w; a is not at least about 1.10-fold greater than x, b is not at least about 1.10-fold greater than y, c is not at least about 1.10-fold greater than z, and/or d is not at least about 1.05-fold greater than v and/or e is not at least about 1.05-fold greater than w; a is not at least about 1.10-fold greater than x, b is not at least about 1.10-fold greater than y, c is not at least about 1.10-fold greater than z, and/or d is at least about 1.05-fold greater than v and/or e is at least about 1.05-fold greater than w; and/or a is at least about 1.10-fold greater than x, b is at least about 1.10-fold greater than y, and/or c is at least about 1.10-fold greater than z, and/or d is not at least about 1.05-fold greater than v and/or e is not at least about 1.05-fold greater than w). In some such embodiments, RNA integrity is increased at least about 5%. In some such embodiments, RNA integrity is increased at least about 8%.

In some embodiments, RNA concentration is assessed using UV absorption spectrophotometry. In some embodiments of the present disclosure, concentration of RNA molecule(s) in a relevant sample or preparation (e.g., in an IVT-solution) produced in accordance with technologies provided herein is at least about 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 11 mg/mL, 12 mg/mL, 13 mg/mL, 14, mg/mL, or 15 mg/mL. In some such embodiments, concentration of RNA molecule(s) (e.g., in a relevant sample or preparation, such as in an IVT-solution) is increased at least about 10%, 11%, 12%, 13%, 14%, 15%, 16%, 17%, 18%, 19%, 20%, 21%, 22%, 23%, 24%, 25%, 26%, 27%, 28%, 29%, or 30% relative to an appropriate comparator (e.g., an otherwise comparable in vitro transcription reaction, for example utilizing a reaction mixture in which a is not at least 1.25, b is not at least 1.25, and/or c is not at least 1.10). In some such embodiments, the concentration of RNA molecule(s) is increased at least about 1%, 2%, 3%, 4%, 5%, 6%, 7%, 8%, 9%, 10%, 11%, 12%, 13%, 14%, 15%, 16%, 17%, 18%, 19%, or 20% relative to an appropriate comparator (e.g., an otherwise comparable in vitro transcription reaction, for exampling utilizing a reaction mixture in which: d is not at least 1.10 and/or e is not at least 1.10; a is not at least 1.25, b is not at least 1.25, c is not at least 1.10, and/or d is not at least 1.10 and/or e is not at least 1.10; a is not at least 1.25, b is not at least 1.25, c is not at least 1.10, and/or d is at least 1.10 and/or e is at least 1.10; and/or a is at least 1.25, b is at least 1.25, and/or c is at least 1.10, and/or d is not at least 1.10 and/or e is not at least 1.10). In some such embodiments, the concentration of RNA molecule(s) produced in accordance with technologies provided herein is increased at least about 10%, 11%, 12%, 13%, 14%, 15%, 16%, 17%, 18%, 19%, 20%, 21%, 22%, 23%, 24%, 25%, 26%, 27%, 28%, 29%, or 30% relative to an appropriate comparator (e.g., an otherwise comparable in vitro transcription reaction, for example utilizing a reaction mixture in which a is not at least about 1.10-fold greater than x, b is not at least about 1.10-fold greater than y, and/or c is not at least about 1.10-fold greater than z). In some such embodiments, concentration of RNA molecule(s) is increased at least about 1%, 2%, 3%, 4%, 5%, 6%, 7%, 8%, 9%, 10%, 11%, 12%, 13%, 14%, 15%, 16%, 17%, 18%, 19%, or 20% relative to an appropriate comparator (e.g., an otherwise comparable in vitro transcription reaction, for example utilizing a reaction mixture in which: d is not at least about 1.05-fold greater than v and/or e is not at least about 1.05-fold greater than w; a is not at least about 1.10-fold greater than x, b is not at least about 1.10-fold greater than y, c is not at least about 1.10-fold greater than z, and/or d is not at least about 1.05-fold greater than v and/or e is not at least about 1.05-fold greater than w; a is not at least about 1.10-fold greater than x, b is not at least about 1.10-fold greater than y, c is not at least about 1.10-fold greater than z, and/or d is at least about 1.05-fold greater than v and/or e is at least about 1.05-fold greater than w; and/or a is at least about 1.10-fold greater than x, b is at least about 1.10-fold greater than y, and/or c is at least about 1.10-fold greater than z, and/or d is not at least about 1.05-fold greater than v and/or e is not at least about 1.05-fold greater than w). In some such embodiments, concentration of RNA molecule(s) is increased at least about 20%.

In some embodiments, residual dsRNA is assessed using polymerase chain reaction (PCR), absorbance, fluorescent dyes, and/or or gel electrophoresis. In some embodiments, residual dsRNA (e.g., in an IVT solution) is assessed using quantitative PCR. In some such embodiments, residual dsRNA during and/or after transcription of RNA molecules is at least about 25 pg dsRNA/μg RNA, 50 pg dsRNA/μg RNA, 75 pg dsRNA/μg RNA, 100 pg dsRNA/μg RNA, 125 pg dsRNA/μg RNA, 150 pg dsRNA/μg RNA, 175 pg dsRNA/μg RNA, 200 pg dsRNA/μg RNA, 225 pg dsRNA/μg RNA, 250 pg dsRNA/μg RNA, 275 pg dsRNA/μg RNA, or 300 pg dsRNA/μg RNA. In some such embodiments, residual dsRNA during and/or after transcription is decreased at least about 60%, 61%, 62%, 63%, 64%, 65%, 66%, 67%, 68%, 69%, 70%, 71%, 72%, 73%, 74%, 75%, 76%, 77%, 78%, 79%, or 80% relative to an appropriate comparator (e.g., relative to an appropriate comparator (e.g., an otherwise comparable in vitro transcription reaction, for example utilizing a reaction mixture in which a is not at least 1.25, b is not at least 1.25, and/or c is not at least 1.10). In some embodiments, residual dsRNA during and/or after transcription is increased at least about 1%, 2%, 3%, 4%, 5%, 6%, 7%, 8%, 9%, 10%, 11%, 12%, 13%, 14%, 15%, 16%, 17%, 18%, 19%, or 20% relative to an appropriate comparator (e.g., an otherwise comparable in vitro transcription reaction, for example utilizing a reaction mixture in which: d is not at least 1.10 and/or e is not at least 1.10; a is not at least 1.25, b is not at least 1.25, c is not at least 1.10, and/or d is not at least 1.10 and/or e is not at least 1.10; a is not at least 1.25, b is not at least 1.25, c is not at least 1.10, and/or d is at least 1.10 and/or e is at least 1.10; and/or a is at least 1.25, b is at least 1.25, and/or c is at least 1.10, and/or d is not at least 1.10 and/or e is not at least 1.10). In some embodiments, residual dsRNA during and/or after transcription is decreased at least about 60%, 61%, 62%, 63%, 64%, 65%, 66%, 67%, 68%, 69%, 70%, 71%, 72%, 73%, 74%, 75%, 76%, 77%, 78%, 79%, or 80% relative to an appropriate comparator (e.g., an otherwise comparable in vitro transcription reaction, for example utilizing a reaction mixture in which a is not at least about 1.10-fold greater than x, b is not at least about 1.10-fold greater than y, and/or c is not at least about 1.10-fold greater than z). In some such embodiments, residual dsRNA during and/or after transcription is increased at least about 1%, 2%, 3%, 4%, 5%, 6%, 7%, 8%, 9%, 10%, 11%, 12%, 13%, 14%, 15%, 16%, 17%, 18%, 19%, or 20% relative to an appropriate comparator (e.g., an otherwise comparable in vitro transcription reaction, for example utilizing a reaction mixture in which: d is not at least about 1.05-fold greater than v and/or e is not at least about 1.05-fold greater than w; a is not at least about 1.10-fold greater than x, b is not at least about 1.10-fold greater than y, c is not at least about 1.10-fold greater than z, and/or d is not at least about 1.05-fold greater than v and/or e is not at least about 1.05-fold greater than w; a is not at least about 1.10-fold greater than x, b is not at least about 1.10-fold greater than y, c is not at least about 1.10-fold greater than z, and/or d is at least about 1.05-fold greater than v and/or e is at least about 1.05-fold greater than w; and/or a is at least about 1.10-fold greater than x, b is at least about 1.10-fold greater than y, and/or c is at least about 1.10-fold greater than z, and/or d is not at least about 1.05-fold greater than v and/or e is not at least about 1.05-fold greater than w). In some such embodiments, residual dsRNA concentration is decreased at least about 70%.

In some embodiments, capping of RNA molecule(s) is assessed by: (a) assessing translation of functionally capped RNA; (b) performing a biological activity test to confirm the RNA molecule is translated into a polypeptide (e.g., protein) of correct size; (c) conducting a nuclease-based assay; and/or (d) conducting a catalytic nucleic acid-based assay. In some such embodiments, a nuclease-based assay comprises an RNase-based assay, for example wherein the RNase-based assay comprises one or more of: (a) annealing a multitude of RNA molecules to one or more probes binding the RNA molecules to form RNA-probe complexes; (b) digesting the RNA-probe complexes with RNase to generate fragments comprising the 5' terminus of the RNA molecules; (c) purifying the fragments using affinity-based purification, chromatography-based purification, or a combination thereof; (d) subjecting the purified fragments to mass spectrometry (MS); (e) identifying capped and uncapped fragments based on observed MS values; and/or (f) comparing the amount of capped and uncapped fragments to calculate the percentage of capped RNA. In some such embodiments, the RNase comprises RNase H. In some such embodiments, the nuclease-based assays comprises one or more of: (a) contacting a multitude of the RNA molecules with one or more DNA oligonucleotides complementary to a sequence in a 5' untranslated region of the RNA molecules adjacent to a 5' RNA cap or an uncapped penultimate base of the RNA; (b) annealing the one or more DNA oligonucleotides to the sequence in the 5' untranslated region of the RNA molecules to form DNA/RNA hybrid complexes; (c) degrading the DNA/RNA hybrid complexes and/or unannealed RNA molecules with one or more nucleases to produce capped and uncapped 5' terminal RNA fragments and 3' RNA fragments; (d) separating the capped and uncapped 5' terminal RNA fragments from the 3' RNA fragments using affinity-based purification, chromatography-based purification, or a combination thereof; and/or (e) comparing the amount of capped and uncapped 5' terminal RNA fragments to calculate the percentage of capped RNA. In some such embodiments, catalytic nucleic acid-based assay comprises one or more of: (a) cleaving a multitude of RNA molecules with a catalytic nucleic acid molecule into 5' terminal RNA fragments and at least one 3' RNA fragments, wherein the RNA molecules have a cleavage site for a catalytic nucleic acid molecule; (b) separating the 5' terminal RNA fragments and 3' RNA fragments using affinity-based purification, chromatography-based purification, or a combination thereof; (c) measuring the amount of capped and uncapped 5' terminal RNA fragments using spectroscopy, quantitative mass spectrometry, sequencing, or a combination thereof; and/or (d) comparing the amount of capped and uncapped 5' terminal RNA fragments to calculate the percentage of capped RNA. In some such embodiments, the catalytic nucleic acid molecule comprises a DNAzyme or a ribozyme. In some such embodiments, at least about 40%, 50%, 60%, 70%, 80%, 90%, or 99% of the RNA molecule(s) produced in accordance with technologies provided herein are capped. In some such embodiments, capping of the RNA molecule(s) produced in accordance with technologies provided herein is increased at least about 1%, 2%, 3%, 4%, 5%, 6%, 7%, 8%, 9%, or 10% relative to an appropriate comparator (e.g., an otherwise comparable in vitro transcription reaction, for example utilizing a reaction mixture in which a is not at least 1.25, b is not at least 1.25, and/or c is not at least 1.10).

In some embodiments, residual dsRNA during and/or after transcription is increased at least about 1%, 2%, 3%, 4%, 5%, 6%, 7%, 8%, 9%, 10%, 11%, 12%, 13%, 14%, 15%, 16%, 17%, 18%, 19%, or 20% relative to an appropriate comparator (e.g., an otherwise comparable in vitro transcription reaction, for example utilizing a reaction mixture in which: d is not at least 1.10 and/or e is not at least 1.10; a is not at least 1.25, b is not at least 1.25, c is not at least 1.10, and/or d is not at least 1.10 and/or e is not at least 1.10; a is not at least 1.25, b is not at least 1.25, c is not at least 1.10, and/or d is at least 1.10 and/or e is at least 1.10; and/or a is at least 1.25, b is at least 1.25, and/or c is at least 1.10, and/or d is not at least 1.10 and/or e is not at least 1.10).

In some embodiments, capping of the RNA molecule(s) produced in accordance with technologies provided herein is increased at least about 1%, 2%, 3%, 4%, 5%, 6%, 7%, 8%, 9%, or 10% relative to an appropriate comparator (e.g., an otherwise comparable in vitro transcription reaction, for example utilizing a reaction mixture in which a is not at least about 1.10-fold greater than x, b is not at least about 1.10-fold greater than y, and/or c is not at least about 1.10-fold greater than z).

In some embodiments, residual dsRNA during and/or after transcription of RNA molecule(s) produced in accordance with technologies provided herein is increased at least about 1%, 2%, 3%, 4%, 5%, 6%, 7%, 8%, 9%, 10%, 11%, 12%, 13%, 14%, 15%, 16%, 17%, 18%, 19%, or 20% relative to an appropriate comparator (e.g., an otherwise comparable in vitro transcription reaction, for example utilizing a reaction mixture in which: d is not at least about 1.05-fold greater than v and/or e is not at least about 1.05-fold greater than w; a is not at least about 1.10-fold greater than x, b is not at least about 1.10-fold greater than y, c is not at least about 1.10-fold greater than z, and/or d is not at least about 1.05-fold greater than v and/or e is not at least about 1.05-fold greater than w; a is not at least about 1.10-fold greater than x, b is not at least about 1.10-fold greater than y, c is not at least about 1.10-fold greater than z, and/or d is at least about 1.05-fold greater than v and/or e is at least about 1.05-fold greater than w; and/or a is at least about 1.10-fold greater than x, b is at least about 1.10-fold greater than y, and/or c is at least about 1.10-fold greater than z, and/or d is not at least about 1.05-fold greater than v and/or e is not at least about 1.05-fold greater than w).

In some embodiments, capping of RNA molecule(s) produced in accordance with technologies provided herein is increased at least about 5%.

BRIEF DESCRIPTION OF THE DRAWING

FIG. 1 provides exemplary IVT reaction mixture components and conditions.

FIG. 6 shows additional exemplary studies demonstrating RNA integrity and percent capping as well as yield and residual CTP levels from exemplary IVT reactions utilizing IVT reaction mixtures comprising either −10%, +10%, +20%, or +50% CTP volume relative to a control (e.g., standard) IVT reaction mixture comprising +0% CTP volume. Light pink markers indicate controls from previous experiments that were assayed with this study.

FIG. 16 shows additional exemplary assessment of IVT reaction mixtures with varying levels of CTP (+10% CTP, +20% CTP, +50% CTP relative to +0% CTP) and characterization of yield, RNA integrity, dsRNA content, and residual DNA content.

FIG. 18 shows additional exemplary assessment of IVT reaction mixtures with varying levels of NTP (+50% CTP and +20% ATP, +50% CTP, +20% ATP relative to control). Yield, integrity, dsRNA content, and residual DNA content were characterized.

FIG. 20 shows exemplary assessment of yield, integrity, and residual dsRNA content of exemplary IVT reactions utilizing reaction mixtures comprising either +25% ATP and +7% CTP, −21% ATP and −37% CTP, +25% ATP, or +7% CTP relative to a reaction mixture comprising 10.8 mM ATP, 13.5 mM CTP, 9 mM GTP, and 9 mM UTP.

DEFINITIONS

Figure 2:
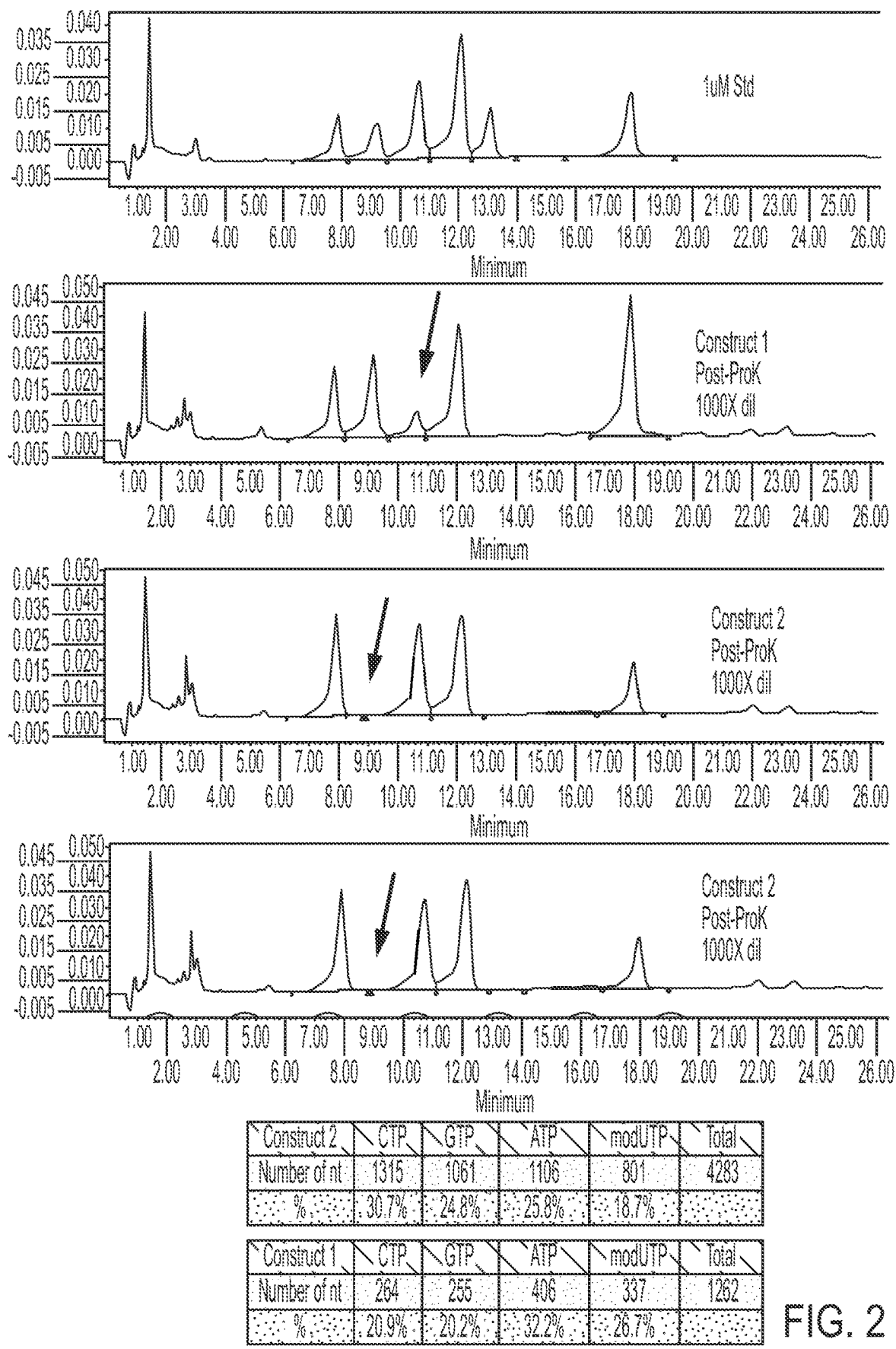
FIG. 2 shows residual nucleotide triphosphates (NTPs) following exemplary, large-scale IVT reactions (36.7 L) performed with two different constructs. Construct 1 is BNT162b1 and Construct 2 is BNT162b2.

About: The term "about", when used herein in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Administration: As used herein, the term "administration" typically refers to the administration of a composition to a subject or system. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc), enteral, intra-arterial, intradermal, intragastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (e.g., by intratracheal instillation), vaginal, vitreal, etc. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Agent: In general, the term "agent", as used herein, is used to refer to an entity (e.g., for example, a lipid, metal, nucleic acid, polypeptide, polysaccharide, small molecule, etc, or complex, combination, mixture or system [e.g., cell, tissue, organism] thereof), or phenomenon (e.g., heat, electric current or field, magnetic force or field, etc). In appropriate circumstances, as will be clear from context to those skilled in the art, the term may be utilized to refer to an entity that is or comprises a cell or organism, or a fraction, extract, or component thereof. Alternatively or additionally, as context will make clear, the term may be used to refer to a natural product in that it is found in and/or is obtained from nature. In some instances, again as will be clear from context, the term may be used to refer to one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents may be provided as collections or libraries, for example that may be screened to identify or characterize active agents within them. In some cases, the term "agent" may refer to a compound or entity that is or comprises a polymer; in some cases, the term may refer to a compound or entity that comprises one or more polymeric moieties. In some embodiments, the term "agent" may refer to a compound or entity that is not a polymer and/or is substantially free of any polymer and/or of one or more particular polymeric moieties. In some embodiments, the term may refer to a compound or entity that lacks or is substantially free of any polymeric moiety.

Allele: As used herein, the term "allele" refers to one of two or more existing genetic variants of a specific polymorphic genomic locus.

Amino acid: in its broadest sense, as used herein, the term "amino acid" refers to a compound and/or substance that can be, is, or has been incorporated into a polypeptide chain, e.g., through formation of one or more peptide bonds. In some embodiments, an amino acid has the general structure $H_2N-C(H)(R)-COOH$. In some embodiments, an amino acid is a naturally-occurring amino acid. In some embodiments, an amino acid is a non-natural amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, pegylation, glycosylation, phosphorylation, and/or substitution (e.g., of the amino group, the carboxylic acid group, one or more protons, and/or the hydroxyl group) as compared with the general structure. In some embodiments, such modification may, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" may be used to refer to a free amino acid; in some embodiments it may be used to refer to an amino acid residue of a polypeptide.

Analog: As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog is a substance that can be generated from the reference substance, e.g., by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance.

Animal: as used herein refers to any member of the animal kingdom. In some embodiments, "animal" refers to humans, of either sex and at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically engineered animal, and/or a clone.

Antigen: The term "antigen", as used herein, refers to an agent that elicits an immune response; and/or (ii) an agent that binds to a T cell receptor (e.g., when presented by an MHC molecule) or to an antibody. In some embodiments, an antigen elicits a humoral response (e.g., including production of antigen-specific antibodies); in some embodiments, an elicits a cellular response (e.g., involving T-cells whose receptors specifically interact with the antigen). In some embodiments, and antigen binds to an antibody and may or may not induce a particular physiological response in an organism. In general, an antigen may be or include any chemical entity such as, for example, a small molecule, a nucleic acid, a polypeptide, a carbohydrate, a lipid, a polymer (in some embodiments other than a biologic polymer [e.g., other than a nucleic acid or amino acid polymer] etc. In some embodiments, an antigen is or comprises a polypeptide. In some embodiments, an antigen is or comprises a glycan. Those of ordinary skill in the art will appreciate that, in general, an antigen may be provided in isolated or pure form, or alternatively may be provided in crude form (e.g., together with other materials, for example in an extract such as a cellular extract or other relatively crude preparation of an antigen-containing source). In some embodiments, antigens utilized in accordance with the present invention are provided in a crude form. In some embodiments, an antigen is a recombinant antigen.

Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell). Binding between two entities may be considered "specific" if, under the conditions assessed, the relevant entities are more likely to associate with one another than with other available binding partners.

Characteristic sequence element: As used herein, the phrase "characteristic sequence element" refers to a sequence element found in a polymer (e.g., in a polypeptide or nucleic acid) that represents a characteristic portion of that polymer. In some embodiments, presence of a characteristic sequence element correlates with presence or level of a particular activity or property of the polymer. In some embodiments, presence (or absence) of a characteristic sequence element defines a particular polymer as a member (or not a member) of a particular family or group of such polymers. A characteristic sequence element typically comprises at least two monomers (e.g., amino acids or nucleotides). In some embodiments, a characteristic sequence element includes at least 2, 3, 4, 5, 6, 7, 8, 9, 10, 11, 12, 13, 14, 15, 20, 25, 30, 35, 40, 45, 50, or more monomers (e.g., contiguously linked monomers). In some embodiments, a characteristic sequence element includes at least first and second stretches of contiguous monomers spaced apart by one or more spacer regions whose length may or may not vary across polymers that share the sequence element.

Comparable: As used herein, the term "comparable" refers to two or more agents, entities, situations, sets of conditions, etc., that may not be identical to one another but that are sufficiently similar to permit comparison there between so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Composition: Those skilled in the art will appreciate that the term "composition", as used herein, may be used to refer to a discrete physical entity that comprises one or more specified components. In general, unless otherwise specified, a composition may be of any form—e.g., gas, gel, liquid, solid, etc.

Comprising: A composition or method described herein as "comprising" one or more named elements or steps is open-ended, meaning that the named elements or steps are essential, but other elements or steps may be added within the scope of the composition or method. To avoid prolixity, it is also understood that any composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step.

Designed: As used herein, the term "designed" refers to an agent (i) whose structure is or was selected by the hand of man; (ii) that is produced by a process requiring the hand of man; and/or (iii) that is distinct from natural substances and other known agents.

Domain: The term "domain" as used herein refers to a section or portion of an entity. In some embodiments, a "domain" is associated with a particular structural and/or functional feature of the entity so that, when the domain is physically separated from the rest of its parent entity, it substantially or entirely retains the particular structural and/or functional feature. Alternatively or additionally, a domain may be or include a portion of an entity that, when separated from that (parent) entity and linked with a different (recipient) entity, substantially retains and/or imparts on the recipient entity one or more structural and/or functional features that characterized it in the parent entity. In some embodiments, a domain is a section or portion of a molecule (e.g., a small molecule, carbohydrate, lipid, nucleic acid, or polypeptide). In some embodiments, a domain is a section of a polypeptide; in some such embodiments, a domain is characterized by a particular structural element (e.g., a particular amino acid sequence or sequence motif, α-helix character, β-sheet character, coiled-coil character, random coil character, etc.), and/or by a particular functional feature (e.g., binding activity, enzymatic activity, folding activity, signaling activity, etc.).

Engineered: In general, the term "engineered" refers to the aspect of having been manipulated by the hand of man. For example, a polynucleotide is considered to be "engineered" when two or more sequences that are not linked together in that order in nature are manipulated by the hand of man to be directly linked to one another in the engineered polynucleotide and/or when a particular residue in a polynucleotide is non-naturally occurring and/or is caused through action of the hand of man to be linked with an entity or moiety with which it is not linked in nature. For example, in some embodiments of the present invention, an engineered polynucleotide comprises a regulatory sequence that is found in nature in operative association with a first coding sequence but not in operative association with a second coding sequence, is linked by the hand of man so that it is operatively associated with the second coding sequence. Comparably, a cell or organism is considered to be "engineered" if it has been subjected to a manipulation, so that its genetic, epigenetic, and/or phenotypic identity is altered relative to an appropriate reference cell such as otherwise identical cell that has not been so manipulated. In some embodiments, the manipulation is or comprises a genetic manipulation, so that its genetic information is altered (e.g., new genetic material not previously present has been introduced, for example by transformation, mating, somatic hybridization, transfection, transduction, or other mechanism, or previously present genetic material is altered or removed, for example by substitution or deletion mutation, or by mating protocols). In some embodiments, an engineered cell is one that has been manipulated so that it contains and/or expresses a particular agent of interest (e.g., a polypeptide (e.g., protein), a nucleic acid, and/or a particular form thereof) in an altered amount and/or according to altered timing relative to such an appropriate reference cell. As is common practice and is understood by those in the art, progeny of an engineered polynucleotide or cell are typically still referred to as "engineered" even though the actual manipulation was performed on a prior entity.

Epitope: as used herein, the term "epitope" refers to a moiety that is specifically recognized by an immunoglobulin (e.g., antibody or receptor) binding component. In some embodiments, an epitope is comprised of a plurality of chemical atoms or groups on an antigen. In some embodiments, such chemical atoms or groups are surface-exposed when the antigen adopts a relevant three-dimensional conformation. In some embodiments, such chemical atoms or groups are physically near to each other in space when the antigen adopts such a conformation. In some embodiments, at least some such chemical atoms or groups are physically separated from one another when the antigen adopts an alternative conformation (e.g., is linearized).

Expression: As used herein, the term "expression" of a nucleic acid sequence refers to the generation of any gene product from the nucleic acid sequence. In some embodiments, a gene product can be a transcript. In some embodiments, a gene product can be a polypeptide. In some embodiments, expression of a nucleic acid sequence involves one or more of the following: (1) production of an RNA template from a DNA sequence (e.g., by transcription); (2) processing of an RNA transcript (e.g., by splicing, editing, etc); (3) translation of an RNA into a polypeptide (e.g., protein); and/or (4) post-translational modification of a polypeptide (e.g., protein).

Fragment: A "fragment" of a material or entity as described herein has a structure that includes a discrete portion of the whole, but lacks one or more moieties found in the whole. In some embodiments, a fragment consists of such a discrete portion. In some embodiments, a fragment consists of or comprises a characteristic structural element or moiety found in the whole. In some embodiments, a polymer fragment comprises or consists of at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500 or more monomeric units (e.g., residues) as found in the whole polymer. In some embodiments, a polymer fragment comprises or consists of at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99% or more of the monomeric units (e.g., residues) found in the whole polymer. The whole material or entity may in some embodiments be referred to as the "parent" of the fragment.

Gene: As used herein, the term "gene" refers to a DNA sequence in a chromosome that codes for a product (e.g., an RNA product and/or a polypeptide product). In some embodiments, a gene includes coding sequence (i.e., sequence that encodes a particular product); in some embodiments, a gene includes non-coding sequence. In some particular embodiments, a gene may include both coding (e.g., exonic) and non-coding (e.g., intronic) sequences. In some embodiments, a gene may include one or more regulatory elements that, for example, may control or impact one or more aspects of gene expression (e.g., cell-type-specific expression, inducible expression, etc.).

Host: The term "host" is used herein to refer to a system (e.g., a cell, organism, etc) in which a polypeptide of interest is present. In some embodiments, a host is a system that is susceptible to infection with a particular infectious agent. In some embodiments, a host is a system that expresses a particular polypeptide of interest.

Host cell: as used herein, refers to a cell into which exogenous nucleic acid (recombinant or otherwise) has been introduced. Persons of skill upon reading this disclosure will understand that such terms refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. In some embodiments, host cells include prokaryotic and eukaryotic cells selected from any of the Kingdoms of life that are suitable for expressing an exogenous DNA (e.g., a recombinant nucleic acid sequence). Exemplary cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic such as, for example: CHO (e.g., CHO K1, DXB-1 1 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, W138, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3 A cell, HT1080 cell, myeloma cell, tumor cell, and a cell line derived from an aforementioned cell. In some embodiments, the cell comprises one or more viral genes.

Identity: As used herein, the term "identity" refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. Calculation of the percent identity of two nucleic acid or polypeptide sequences, for example, can be performed by aligning the two sequences for optimal comparison purposes (e.g., gaps can be introduced in one or both of a first and a second sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of a reference sequence. The nucleotides at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0). In some exemplary embodiments, nucleic acid sequence comparisons made with the ALIGN program use a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

"Improved," "increased" or "reduced": As used herein, these terms, or grammatically comparable comparative terms, indicate values that are relative to a comparable reference measurement. For example, in some embodiments, an assessed value achieved with an agent of interest may be "improved" relative to that obtained with a comparable reference agent. Alternatively or additionally, in some embodiments, an assessed value achieved in a subject or system of interest may be "improved" relative to that obtained in the same subject or system under different conditions (e.g., prior to or after an event such as administration of an agent of interest), or in a different, comparable subject (e.g., in a comparable subject or system that differs from the subject or system of interest in presence of one or more indicators of a particular disease, disorder or condition of interest, or in prior exposure to a condition or agent, etc). In some embodiments, comparative terms refer to statistically relevant differences (e.g., that are of a prevalence and/or magnitude sufficient to achieve statistical relevance). Those skilled in the art will be aware, or will readily be able to determine, in a given context, a degree and/or prevalence of difference that is required or sufficient to achieve such statistical significance.

In vitro: The term "in vitro" as used herein refers to events that occur in an artificial environment, e.g., in a test tube or reaction vessel, in cell culture, etc., rather than within a multi-cellular organism.

Linker: as used herein, is used to refer to that portion of a multi-element agent that connects different elements to one another. For example, those of ordinary skill in the art appreciate that a polypeptide whose structure includes two or more functional or organizational domains often includes a stretch of amino acids between such domains that links them to one another. In some embodiments, a polypeptide comprising a linker element has an overall structure of the general form S1-L-S2, wherein S1 and S2 may be the same or different and represent two domains associated with one another by the linker. In some embodiments, a polypeptide linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length. In some embodiments, a linker is characterized in that it tends not to adopt a rigid three-dimensional structure, but rather provides flexibility to the polypeptide. A variety of different linker elements that can appropriately be used when engineering polypeptides (e.g., fusion polypeptides) known in the art (see e.g., Holliger, P., et al. (1993) Proc. Natl. Acad. Sci. USA 90:6444-6448; Poljak, R. J., et al. (1994) Structure 2: 1 121-1123).

Moiety: Those skilled in the art will appreciate that a "moiety" is a defined chemical group or entity with a particular structure and/or or activity, as described herein.

Nucleic acid: As used herein, in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to an individual nucleic acid residue (e.g., a nucleotide and/or nucleoside); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present invention. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxy guanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or polypeptide (e.g., protein). In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is partly or wholly single stranded; in some embodiments, a nucleic acid is partly or wholly double stranded. In some embodiments a nucleic acid has a nucleotide sequence comprising at least one element that encodes, or is the complement of a sequence that encodes, a polypeptide. In some embodiments, a nucleic acid has enzymatic activity.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Polypeptide: As used herein refers to a polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may comprise or consist of natural amino acids, non-natural amino acids, or both. In some embodiments, a polypeptide may comprise or consist of only natural amino acids or only non-natural amino acids. In some embodiments, a polypeptide may comprise D-amino acids, L-amino acids, or both. In some embodiments, a polypeptide may comprise only D-amino acids. In some embodiments, a polypeptide may comprise only L-amino acids. In some embodiments, a polypeptide may include one or more pendant groups or other modifications, e.g., modifying or attached to one or more amino acid side chains, at the polypeptide's N-terminus, at the polypeptide's C-terminus, or any combination thereof. In some embodiments, such pendant groups or modifications may be selected from the group consisting of acetylation, amidation, lipidation, methylation, pegylation, etc., including combinations thereof. In some embodiments, a polypeptide may be cyclic, and/or may comprise a cyclic portion. In some embodiments, a polypeptide is not cyclic and/or does not comprise any cyclic portion. In some embodiments, a polypeptide is linear. In some embodiments, a polypeptide may be or comprise a stapled polypeptide. In some embodiments, the term "polypeptide" may be appended to a name of a reference polypeptide, activity, or structure; in such instances it is used herein to refer to polypeptides that share the relevant activity or structure and thus can be considered to be members of the same class or family of polypeptides. For each such class, the present specification provides and/or those skilled in the art will be aware of exemplary polypeptides within the class whose amino acid sequences and/or functions are known; in some embodiments, such exemplary polypeptides are reference polypeptides for the polypeptide class or family. In some embodiments, a member of a polypeptide class or family shows significant sequence homology or identity with, shares a common sequence motif (e.g., a characteristic sequence element) with, and/or shares a common activity (in some embodiments at a comparable level or within a designated range) with a reference polypeptide of the class; in some embodiments with all polypeptides within the class). For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (e.g., a conserved region that may in some embodiments be or comprise a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a relevant polypeptide may comprise or consist of a fragment of a parent polypeptide. In some embodiments, a useful polypeptide as may comprise or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide.

Predetermined: By predetermined is meant deliberately selected, for example as opposed to randomly occurring or achieved.

Prevent or prevention: as used herein when used in connection with the occurrence of a disease, disorder, and/or condition, refers to reducing the risk of developing the disease, disorder and/or condition and/or to delaying onset of one or more characteristics or symptoms of the disease, disorder or condition. Prevention may be considered complete when onset of a disease, disorder or condition has been delayed for a predefined period of time.

Pure: As used herein, an agent or entity is "pure" if it is substantially free of other components. For example, a preparation that contains more than about 90% of a particular agent or entity is typically considered to be a pure preparation. In some embodiments, an agent or entity is at least 91%, at least 92%, at least 93%, at least 94%, at least 95%, at least 96%, at least 97%, at least 98%, or at least 99% pure.

Reference: As used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Sample: As used herein, the term "sample" typically refers to an aliquot of material obtained or derived from a source of interest, as described herein. In some embodiments, a source of interest is a biological or environmental source. In some embodiments, a source of interest may be or comprise a cell or an organism, such as a microbe, a plant, or an animal (e.g., a human). In some embodiments, a source of interest is or comprises biological tissue or fluid. In some embodiments, a biological tissue or fluid may be or comprise amniotic fluid, aqueous humor, ascites, bile, bone marrow, blood, breast milk, cerebrospinal fluid, cerumen, chyle, chime, ejaculate, endolymph, exudate, feces, gastric acid, gastric juice, lymph, mucus, pericardial fluid, perilymph, peritoneal fluid, pleural fluid, pus, rheum, saliva, sebum, semen, serum, smegma, sputum, synovial fluid, sweat, tears, urine, vaginal secretions, vitreous humour, vomit, and/or combinations or component(s) thereof. In some embodiments, a biological fluid may be or comprise an intracellular fluid, an extracellular fluid, an intravascular fluid (blood plasma), an interstitial fluid, a lymphatic fluid, and/or a transcellular fluid. In some embodiments, a biological fluid may be or comprise a plant exudate. In some embodiments, a biological tissue or sample may be obtained, for example, by aspirate, biopsy (e.g., fine needle or tissue biopsy), swab (e.g., oral, nasal, skin, or vaginal swab), scraping, surgery, washing or lavage (e.g., broncheoalveolar, ductal, nasal, ocular, oral, uterine, vaginal, or other washing or lavage). In some embodiments, a biological sample is or comprises cells obtained from an individual. In some embodiments, a sample is a "primary sample" obtained directly from a source of interest by any appropriate means. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or polypeptides (e.g., proteins) extracted from a sample or obtained by subjecting a primary sample to one or more techniques such as amplification or reverse transcription of nucleic acid, isolation and/or purification of certain components, etc.

Subject: As used herein, the term "subject" refers an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Therapeutic agent: As used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

Treatment: As used herein, the term "treatment" (also "treat" or "treating") refers to administration of a therapy that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition. Thus, in some embodiments, treatment may be prophylactic; in some embodiments, treatment may be therapeutic.

Vaccination: As used herein, the term "vaccination" refers to the administration of a composition intended to generate an immune response, for example to a disease-associated (e.g., disease-causing) agent. In some embodiments, vaccination can be administered before, during, and/or after exposure to a disease-associated agent, and in certain embodiments, before, during, and/or shortly after exposure to the agent. In some embodiments, vaccination includes multiple administrations, appropriately spaced in time, of a vaccinating composition.

Variant: As used herein in the context of molecules, e.g., nucleic acids, polypeptides (e.g., proteins), or small molecules, the term "variant" refers to a molecule that shows significant structural identity with a reference molecule but differs structurally from the reference molecule, e.g., in the presence or absence or in the level of one or more chemical moieties as compared to the reference entity. In some embodiments, a variant also differs functionally from its reference molecule. In general, whether a particular molecule is properly considered to be a "variant" of a reference molecule is based on its degree of structural identity with the reference molecule. As will be appreciated by those skilled in the art, any biological or chemical reference molecule has certain characteristic structural elements. A variant, by definition, is a distinct molecule that shares one or more such characteristic structural elements but differs in at least one aspect from the reference molecule. To give but a few examples, a polypeptide may have a characteristic sequence element comprised of a plurality of amino acids having designated positions relative to one another in linear or three-dimensional space and/or contributing to a particular structural motif and/or biological function; a nucleic acid may have a characteristic sequence element comprised of a plurality of nucleotide residues having designated positions relative to on another in linear or three-dimensional space. In some embodiments, a variant polypeptide or nucleic acid may differ from a reference polypeptide or nucleic acid as a result of one or more differences in amino acid or nucleotide sequence and/or one or more differences in chemical moieties (e.g., carbohydrates, lipids, phosphate groups) that are covalently components of the polypeptide or nucleic acid (e.g., that are attached to the polypeptide or nucleic acid backbone). In some embodiments, a variant polypeptide or nucleic acid shows an overall sequence identity with a reference polypeptide or nucleic acid that is at least 85%, 86%, 87%, 88%, 89%, 90%, 91%, 92%, 93%, 94%, 95%, 96%, 97%, or 99%. In some embodiments, a variant polypeptide or nucleic acid does not share at least one characteristic sequence element with a reference polypeptide or nucleic acid. In some embodiments, a reference polypeptide or nucleic acid has one or more biological activities. In some embodiments, a variant polypeptide or nucleic acid shares one or more of the biological activities of the reference polypeptide or nucleic acid. In some embodiments, a variant polypeptide or nucleic acid lacks one or more of the biological activities of the reference polypeptide or nucleic acid. In some embodiments, a variant polypeptide or nucleic acid shows a reduced level of one or more biological activities as compared to the reference polypeptide or nucleic acid. In some embodiments, a polypeptide or nucleic acid of interest is considered to be a "variant" of a reference polypeptide or nucleic acid if it has an amino acid or nucleotide sequence that is identical to that of the reference but for a small number of sequence alterations at particular positions. Typically, fewer than about 20%, about 15%, about 10%, about 9%, about 8%, about 7%, about 6%, about 5%, about 4%, about 3%, or about 2% of the residues in a variant are substituted, inserted, or deleted, as compared to the reference. In some embodiments, a variant polypeptide or nucleic acid comprises about 10, about 9, about 8, about 7, about 6, about 5, about 4, about 3, about 2, or about 1 substituted residues as compared to a reference. Often, a variant polypeptide or nucleic acid comprises a very small number (e.g., fewer than about 5, about 4, about 3, about 2, or about 1) number of substituted, inserted, or deleted, functional residues (i.e., residues that participate in a particular biological activity) relative to the reference. In some embodiments, a variant polypeptide or nucleic acid comprises not more than about 5, about 4, about 3, about 2, or about 1 addition or deletion, and, in some embodiments, comprises no additions or deletions, as compared to the reference. In some embodiments, a variant polypeptide or nucleic acid comprises fewer than about 25, about 20, about 19, about 18, about 17, about 16, about 15, about 14, about 13, about 10, about 9, about 8, about 7, about 6, and commonly fewer than about 5, about 4, about 3, or about 2 additions or deletions as compared to the reference. In some embodiments, a reference polypeptide or nucleic acid is one found in nature. In some embodiments, a reference polypeptide or nucleic acid is a human polypeptide or nucleic acid.

Vector: as used herein, refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors." Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al., Molecular Cloning: A Laboratory Manual (2d ed., Cold Spring Harbor Laboratory Press, Cold Spring Harbor, N.Y. (1989)), which is incorporated herein by reference for any purpose.

Wild-type: As used herein, the term "wild-type" has its art-understood meaning that refers to an entity having a structure and/or activity as found in nature in a "normal" (as contrasted with mutant, diseased, altered, etc.) state or context. Those of ordinary skill in the art will appreciate that wild-type genes and polypeptides often exist in multiple different forms (e.g., alleles).

DETAILED DESCRIPTION OF CERTAIN EMBODIMENTS

RNA therapeutics have recently emerged as a relatively new and promising class of therapies for treatment and/or prevention of various diseases such as cancer, infectious diseases, and/or diseases or disorders associated with deficiency in certain polypeptides (e.g., proteins). Particularly given the promise of these technologies, and its adaptability to a wide variety of clinical contexts, including massively large scale (e.g., vaccination and/or treatment on a global scale, e.g., for communicable disease, e.g., influenza, coronavirus [e.g., SARS, MERS, etc.]), improvements to manufacturing technologies, especially those applicable to large-scale production, are particularly valuable.

Technologies provided herein are useful, among other things, to achieve particularly effective and/or efficient production, e.g., on a commercial scale and/or under commercial conditions, of compositions and/or preparations comprising RNA. For example, in various embodiments, provided technologies permit and/or facilitate achievement of requirements unique to pharmaceutical-grade (and/or scale) production such as, for example, batch size and/or rate of production and/or pre-determined quality control parameters.

The present disclosure, among other things, provides technologies for manufacturing RNA, e.g., therapeutic RNA such as therapeutic mRNA and/or compositions comprising the same, by IVT. In some embodiments, provided technologies are useful for manufacturing pharmaceutical grade RNA and/or RNA therapeutics. In some embodiments, provided technologies are useful for large scale manufacturing of RNA therapeutics, e.g., pharmaceutical-grade RNA therapeutics.

For example, in some such embodiments, technologies provided herein can be used to produce a batch throughput (e.g., a pharmaceutical-grade batch throughput) of at least 1,000 vials of RNA therapeutics (including, e.g., at least 2,000 vials, at least 5,000 vials, at least 10,000 vials, at least 20,000 vials, at least 30,000 vials, at least 40,000 vials, at least 50,000 vials, at least 60,000 vials, at least 70,000 vials, at least 80,000 vials, at least 90,000 vials, at least 100,000 vials, at least 200,000 vials, at least 300,000 vials, at least 400,000 vials, at least 500,000 vials, 600,000 vials, 700,000 vials, 800,000 vials, 900,000 vials, 1,000,000 vials or more).

For example, in some such embodiments, technologies provided herein can be used to produce a batch throughput (e.g., a pharmaceutical-grade batch throughput) of at least 50 L of RNA therapeutics (including e.g., at least 50 L, at least 60 L, at least 70 L, at least 80 L, at least 100 L, at least 110 L, at least 120 L, at least 130 L, at least 140 L, at least 150 L or more. In some embodiments, each vial can comprise a RNA in an amount of 0.01 mg to 5 mg (e.g., 0.01 mg, 0.02 mg, 0.03 mg, 0.04 mg, 0.05 mg, 0.06 mg, 0.07 mg, 0.08 mg, 0.09 mg, 0.1 mg, 0.15 mg, 0.2 mg, 0.25 mg, 0.3 mg, 0.35 mg, 0.4 mg, 0.45 mg, 0.5 mg).

Among other things, the present disclosure provides an insight that elevated cytidine triphosphate (CTP) and/or adenosine triphosphate (ATP) concentrations can provide certain benefits in IVT reactions, including for production of pharmaceutical-grade RNA compositions and/or preparations, and particularly for large-scale production, independently of the percent and/or molar ratio of nucleotides (e.g., nucleotide content) in the produced RNA.

Technologies described herein can be useful for manufacturing RNA compositions (e.g., RNA such as, e.g., mRNA and compositions comprising the same). In some embodiments, technologies described here can be useful for manufacturing mRNA compositions for treatment and/or prevention of a disease, disorder, or condition (e.g., cancer, infectious diseases, diseases associates with polypeptide (e.g., protein) deficiency, etc.). In some embodiments, technologies described herein can be useful for manufacturing mRNA compositions encoding a polypeptide and/or a plurality of polypeptides.

Compositions

In some embodiments, the present disclosure, among other things, provides methods of manufacturing compositions and/or preparations comprising RNA by in vitro transcription (IVT). In some embodiments, compositions and/or preparations comprise therapeutic RNA (e.g., mRNA). In some embodiments, methods of manufacturing compositions and/or preparations of the present disclosure is at a commercial scale, for example, at a mass batch throughput of at least of at least 0.01 g, 0.02 g, 0.03 g, 0.04 g, 0.05 g, 0.06 g, 0.07 g, 0.08 g, 0.09 g, 0.1 g, 0.5 g, 1 g, 2 g, 3 g, 4 g, 5 g, 6 g, 7 g, 8 g, 9 g, 10 g RNA (including, e.g., at least 15 g RNA, at least 20 g RNA, at least 25 g RNA, at least 30 g RNA, at least 35 g RNA, at least 40 g RNA, at least 45 g RNA, at least 50 g RNA, at least 55 g RNA, at least 60 g RNA, at least 70 g RNA, at least 80 g RNA, at least 90 g RNA, at least 100 g RNA, at least 150 g RNA, at least 200 g RNA, at least 300 g RNA, at least 400 g RNA, at least 500 g RNA or more). In some embodiments, such a method described herein can be used to produce a mass batch throughput of about 0.01 g to about 500 g RNA, about 0.01 g to about 10 g RNA, about 1 g to about 10 g RNA, about 10 g to about 500 g RNA, about 10 g to about 300 g RNA, about 10 g to about 200 g RNA or about 30 g to about 60 g RNA. In some embodiments, such a method described herein is useful for large scale manufacturing that produces a mass batch throughput of at least 1.5 g RNA per hour (including, e.g., at least 2 g RNA per hour, at least 2.5 g RNA per hour, at least 3 g RNA per hour, at least 3.5 g RNA per hour, at least 4 g RNA per hour, at least 4.5 g RNA per hour, at least 5 g RNA per hour, at least 5.5 g RNA per hour, at least 6 g RNA per hour, at least 6.5 g RNA per hour, at least 7 g RNA per hour, at least 7.5 g RNA per hour, at least 8 g RNA per hour, at least 8.5 g RNA per hour, at least 9 g RNA per hour, at least 10 g RNA per hour or higher). In some embodiments, large scale manufacture methods described herein can reach a capacity of 15 g RNA per hour to 20 g RNA per hour (e.g., about 17 g per hour).

RNAs

In some embodiments, an RNA amenable to technologies described herein is a single-stranded RNA. In some embodiments, an RNA as disclosed herein is a linear RNA. In some embodiments, a single-stranded RNA is a non-coding RNA in that its nucleotide sequence does not include an open reading frame (or complement thereof). In some embodiments, a single-stranded RNA has a nucleotide sequence that encodes (or is the complement of a sequence that encodes) a polypeptide or a plurality of polypeptides (e.g., epitopes) of the present disclosure.

In many embodiments, a relevant RNA is an mRNA.

In some embodiments, an RNA includes unmodified uridine residues; an RNA that includes only unmodified uridine residues may be referred to as a "uRNA". In some embodiments, an RNA includes one or more modified uridine residues; in some embodiments, such an RNA (e.g., an RNA including entirely modified uridine residues) is referred to as a "modRNA". In some embodiments, an RNA may be a self-amplifying RNA (saRNA). In some embodiments, an RNA may be a trans-amplifying RNA (see, for example, WO2017/162461).

In some embodiments, technologies described herein may be particularly useful for production of an RNA (e.g., a single stranded RNA) having a length of at least 500 ribonucleotides (such as, e.g., at least 600 ribonucleotides, at least 700 ribonucleotides, at least 800 ribonucleotides, at least 900 ribonucleotides, at least 1000 ribonucleotides, at least 1250 ribonucleotides, at least 1500 ribonucleotides, at least 1750 ribonucleotides, at least 2000 ribonucleotides, at least 2500 ribonucleotides, at least 3000 ribonucleotides, at least 3500 ribonucleotides, at least 4000 ribonucleotides, at least 4500 ribonucleotides, at least 5000 ribonucleotides, or longer). In some embodiments, technologies described herein may be particularly useful for synthesizing a single-stranded RNA having a length of about 800 ribonucleotides to 5000 ribonucleotides.

In some embodiments, a relevant RNA includes a polypeptide-encoding portion or a plurality of polypeptide-encoding portions. In some particular embodiments, such a portion or portions may encode a polypeptide or polypeptides that is or comprises an antigen (or an epitope thereof), a cytokine, an enzyme, etc. In some embodiments, an encoded polypeptide or polypeptides may be or include one or more neoantigens or neoepitopes associated with a tumor. In some embodiments, an encoded polypeptide or polypeptides may be or include one or more antigens (or epitopes thereof) of an infectious agent (e.g., a bacterium, fungus, virus, etc.). In certain embodiments, an encoded polypeptide may be a variant of a wild type polypeptide.

In some embodiments, a single-stranded RNA (e.g., mRNA) may comprise a secretion signal-encoding region (e.g., a secretion signal-encoding region that allows an encoded target entity or entities to be secreted upon translation by cells). In some embodiments, such a secretion signal-encoding region may be or comprise a non-human secretion signal. In some embodiments, such a secretion signal-encoding region may be or comprise a human secretion signal.

In some embodiments, a single-stranded RNA (e.g., mRNA) may comprise at least one non-coding sequence element (e.g., to enhance RNA stability and/or translation efficiency). Examples of non-coding sequence elements include but are not limited to a 3' untranslated region (UTR), a 5' UTR, a cap structure for co-transcriptional capping of mRNA, a poly adenine (polyA) tail, and any combinations thereof.

Formats

At least four formats useful for RNA pharmaceutical compositions (e.g., immunogenic compositions or vaccines) have been developed, namely non-modified uridine containing mRNA (uRNA), nucleosidemodified mRNA (modRNA), self-amplifying mRNA (saRNA), and trans-amplifying RNAs.

Features of a non-modified uridine platform may include, for example, one or more of intrinsic adjuvant effect, good tolerability and safety, and strong antibody and T cell responses.

Features of modified uridine (e.g., pseudouridine) platform may include reduced adjuvant effect, blunted immune innate immune sensor activating capacity and thus augmented antigen expression, good tolerability and safety, and strong antibody and CD4-T cell responses. As noted herein, the present disclosure provides an insight that such strong antibody and CD4 T cell responses may be particularly useful for vaccination.

Features of self-amplifying platform may include, for example, long duration of polypeptide (e.g., protein) expression, good tolerability and safety, higher likelihood for efficacy with very low vaccine dose.

In some embodiments, a self-amplifying platform (e.g., RNA) comprises two nucleic acid molecules, wherein one nucleic acid molecule encodes a replicase (e.g., a viral replicase) and the other nucleic acid molecule is capable of being replicated (e.g., a replicon) by said replicase in trans (trans-replication system). In some embodiments, a self-amplifying platform (e.g., RNA) comprises a plurality of nucleic acid molecules, wherein said nucleic acids encode a plurality of replicases and/or replicons.

In some embodiments, a trans-replication system comprises the presence of both nucleic acid molecules in a single host cell.

In some such embodiments, a nucleic acid encoding a replicase (e.g., a viral replicase) is not capable of self-replication in a target cell and/or target organism. In some such embodiments, a nucleic acid encoding a replicase (e.g., a viral replicase) lacks at least one conserved sequence element important for (−) strand synthesis based on a (+) strand template and/or for (+) strand synthesis based on a (−) strand template.

In some embodiments, a self-amplifying RNA comprises a 5'-cap. Without wishing to be bound by any one theory, it has been found that a 5'-cap is important for high level expression of a gene of interest in trans. In some embodiments, a 5'-cap drives expression of a replicase.

In some embodiments, a self-amplifying RNA does not comprise an Internal Ribosomal Entry Site (IRES) element. In some such embodiments, translation of a gene of interest and/or replicase is not driven by an IRES element. In some embodiments, an IRES element is substituted by a 5'-cap. In some such embodiments, substitution by a 5'-cap does not affect the sequence of a polypeptide encoded by an RNA.

In some embodiments, a self-amplifying platform does not require propagation of virus particles (e.g., is not associated with undesired virus-particle formation). In some embodiments, a self-amplifying platform is not capable of forming virus particles.

5'-Cap

In some embodiments, a polynucleotide (e.g., RNA) utilized in accordance with the present disclosure comprises a 5'-cap. RNA capping is well researched and is described, e.g., in Decroly E et al. (2012) Nature Reviews 10: 51-65; and in Ramanathan A. et al., (2016) Nucleic Acids Res; 44(16): 7511-7526, the entire contents of each of which is hereby incorporated by reference. In some embodiments, a 5'-cap structure which may be suitable in the context of the present invention is a cap0 (methylation of the first nucleobase, e.g. m7GpppN), cap1 (additional methylation of the ribose of the adjacent nucleotide of m7GpppN), cap2 (additional methylation of the ribose of the 2nd nucleotide downstream of the m7GpppN), cap3 (additional methylation of the ribose of the 3rd nucleotide downstream of the m7GpppN), cap4 (additional methylation of the ribose of the 4th nucleotide downstream of the m7GpppN), ARCA (anti-reverse cap analogue), modified ARCA (e.g. phosphothioate modified ARCA, e.g., beta-S-ARCA), inosine, N1-methyl-guanosine, 2'-fluoro-guanosine, 7-deaza-guanosine, 8-oxo-guanosine, 2-amino-guanosine, LNA-guanosine, and 2-azido-guanosine.

In some embodiments, a utilized 5' caps is a Cap-0 (also referred herein as "Cap0"), a Cap-1 (also referred herein as "Cap1"), or Cap-2 (also referred herein as "Cap2"). See, e.g., FIG. 1 of Ramanathan A et al., and FIG. 1 of Decroly E et al.

The term "5'-cap" as used herein refers to a structure found on the 5'-end of an RNA, e.g., mRNA, and generally includes a guanosine nucleotide connected to an RNA, e.g., mRNA, via a 5'- to 5'-triphosphate linkage (also referred to as Gppp or G(5')ppp(5')). In some embodiments, a guanosine nucleoside included in a 5' cap may be modified, for example, by methylation at one or more positions (e.g., at the 7-position) on a base (guanine), and/or by methylation at one or more positions of a ribose. In some embodiments, a guanosine nucleoside included in a 5' cap comprises a 3'O methylation at a ribose (3'OMeG). In some embodiments, a guanosine nucleoside included in a 5' cap comprises methylation at the 7-position of guanine (m7G). In some embodiments, a guanosine nucleoside included in a 5' cap comprises methylation at the 7-position of guanine and a 3' O methylation at a ribose (m7(3'OMeG)).

In some embodiments, providing an RNA with a 5'-cap disclosed herein or a 5'-cap analog may be achieved by in vitro transcription, in which a 5'-cap is co-transcriptionally expressed into an RNA strand, or may be attached to an RNA post-transcriptionally using capping enzymes. In some embodiments, co-transcriptional capping with a cap disclosed herein, e.g., with a cap1 or a cap1 analog, improves the capping efficiency of an RNA compared to co-transcriptional capping with an appropriate reference comparator. In some embodiments, improving capping efficiency can increase a translation efficiency and/or translation rate of an RNA, and/or increase expression of an encoded polypeptide.

In some embodiments, an RNA described herein comprises a 5'-cap or a 5' cap analog, e.g., a Cap0, a Cap1 or a Cap2. In some embodiments, a provided RNA does not have uncapped 5'-triphosphates. In some embodiments, an RNA may be capped with a 5'-cap analog. In some embodiments, an RNA described herein comprises a Cap0. In some embodiments, an RNA described herein comprises a Cap1, e.g., as described herein. In some embodiments, an RNA described herein comprises a Cap2. In some embodiments, alterations to polynucleotides generates a non-hydrolyzable cap structure which can, for example, prevent decapping and increase RNA half-life.

In some embodiments, a Cap0 structure comprises a guanosine nucleoside methylated at the 7-position of guanine (m7G). In some embodiments, a Cap0 structure is connected to an RNA via a 5'- to 5'-triphosphate linkage and is also referred to herein as m7Gppp or m7G(5')ppp(5').

In some embodiments, a Cap1 structure comprises a guanosine nucleoside methylated at the 7-position of guanine ($^{m7}G$ or $^{7m}G$) and a 2'O methylated first nucleotide in an RNA (2'OMeN$_1$ or N$_1^{2'OMe}$ or N$_1^{2'OMe}$). In some embodiments, a Cap1 structure is connected to an RNA via a 5'- to 5'-triphosphate linkage; in some embodiments, a Cap1 structure may be represented as $^{m7}$Gppp(N$_1^{2'OMe}$) or $^{m7}$G(5')ppp(5')(N$_1^{2'OMe}$) or $^{7m}$G(5')ppp(5')N$_1^{2'-OMe}$) In some embodiments, N$_1$ is chosen from A, C, G, or U. In some embodiments, N$_1$ is A. In some embodiments, N$_1$ is C. In some embodiments, N$_1$ is G. In some embodiments, N$_1$ is U.

Those skilled in the art will appreciate that methylation of one or more positions in a cap structure may impact or reflect mode of incorporation (e.g., co-transcriptional vs post-transcriptional), as presence of a methyl group (e.g., a 2'OMe group) at certain positions (e.g., N$_1$) may interfere with elongation, e.g., by a particular polymerase (e.g., T7), as underlies the ARCA technology.

In some embodiments, a $^{m7}$G(5')ppp(5')(N$_1^{2'OMe}$) Cap1 structure comprises a second nucleotide, N$_2$ which is a cap proximal A, G, C, or U at position +2. In some embodiments, such Cap1 structures are represented as ($^{m7}$G(5')ppp(5')(N$_1^{2'OMe}$)pN$_2$). In some embodiments, N$_2$ is A. In some embodiments, N$_2$ is C. In some embodiments, N$_2$ is G. In some embodiments, N$_2$ is U.

In some embodiments, a Cap1 structure is or comprises $^{m7}$G(5')ppp(5')(A$_1^{2'OMe}$)pG$_2$ wherein A$_1$ is a cap proximal A at position +1 and G$_2$ is a cap proximal G at position +2, and has the following structure:

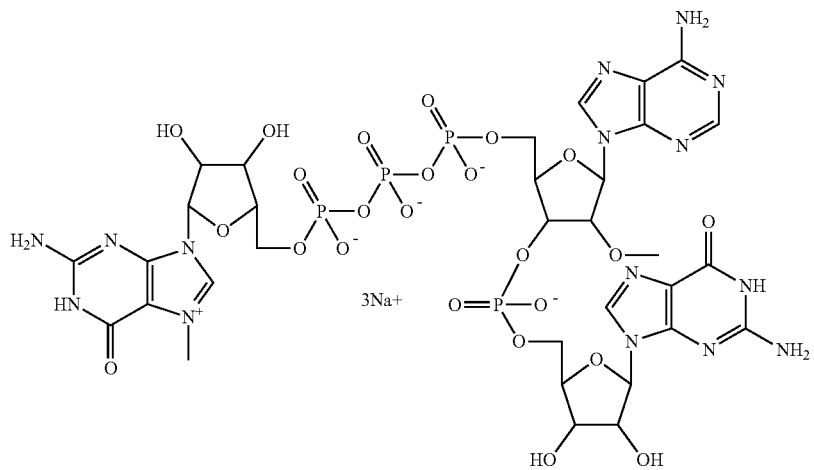 [SMILES: COC1C(OP(=O)(O)OCC2OC(n3cnc4c(=O)[nH]c(N)nc43)C(O)C2O)C(COP(=O)(O)OP(=O)(O)OP(=O)(O)OCC2OC(n3c[n+](C)c4c(=O)[nH]c(N)nc43)C(O)C2O)OC1n1cnc2c(N)ncnc21]

40

In some embodiments, a Cap1 structure is or comprises $^{m7}$G(5')ppp(5')(A$_1^{2'OMe}$)pU$_2$ wherein A$_1$ is a cap proximal A at position +1 and U$_2$ is a cap proximal U at position +2, and has the following structure:

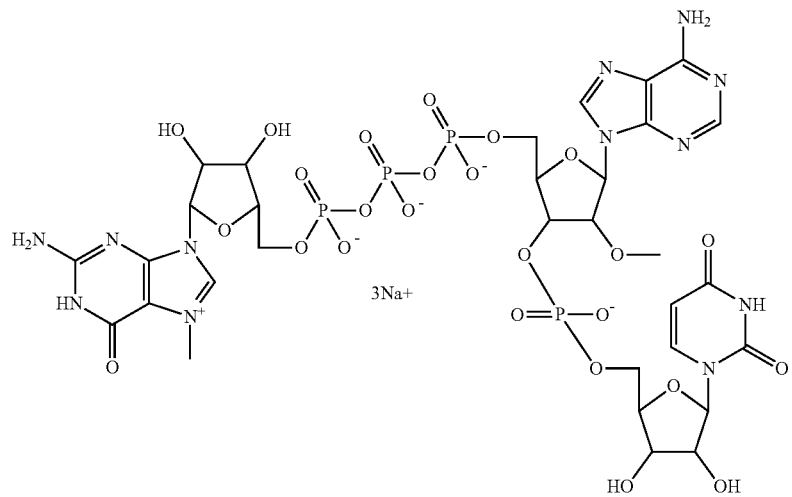 [SMILES: COC1C(OP(=O)(O)OCC2OC(n3ccc(=O)[nH]c3=O)C(O)C2O)C(COP(=O)(O)OP(=O)(O)OP(=O)(O)OCC2OC(n3c[n+](C)c4c(=O)[nH]c(N)nc43)C(O)C2O)OC1n1cnc2c(N)ncnc21]

In some embodiments, a Cap1 structure is or comprises $^{m7}G(5')ppp(5')(G_1{}^{2'OMe})pG_2$ wherein $G_1$ is a cap proximal G at position +1 and $G_2$ is a cap proximal G at position +2, and has the following structure:

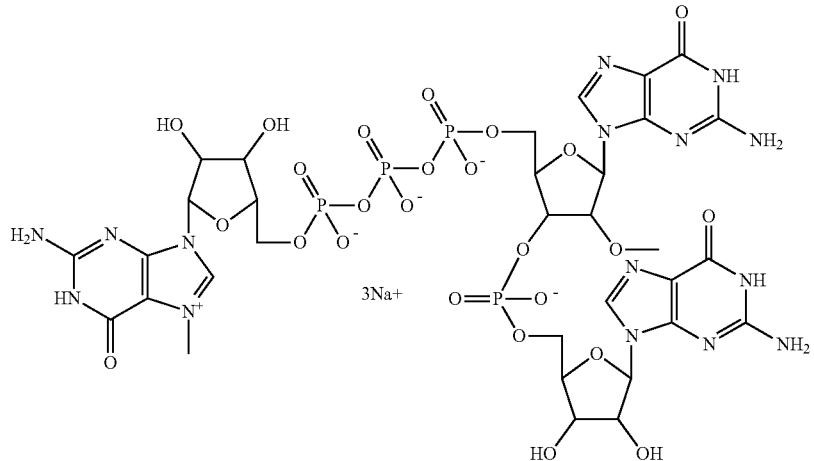 [SMILES: COC1C(OP(=O)(O)OCC2OC(n3cnc4c(=O)[nH]c(N)nc43)C(O)C2O)C(COP(=O)(O)OP(=O)(O)OP(=O)(O)OCC2OC(n3c[n+](C)c4c(=O)[nH]c(N)nc43)C(O)C2O)OC1n1cnc2c(=O)[nH]c(N)nc21]

In some embodiments, a Cap1 structure comprises a guanosine nucleoside methylated at the 7-position of guanine ($^{m7}G$) and one or more additional modifications, e.g., methylation on a ribose, and a 2'O methylated first nucleotide in an RNA. In some embodiments, a Cap1 structure comprises a guanosine nucleoside methylated at the 7-position of guanine and a 3'O methylation at a ribose (m7G3'OMe) or $^{7m}G^{3'OMe}$); and a 2'O methylated first nucleotide in an RNA ($N_1{}^{2'OMe}$). In some embodiments, a Cap1 structure is connected to an RNA via a 5'- to 5'-triphosphate linkage and is also referred to herein as (m7G3'OMe)ppp(2'OMeN$_1$) or $(^{m7}G^{3'OMe})(5')ppp(5')(^{2'OMe}N_1)$. In some embodiments, $N_1$ is chosen from A, C, G, or U. In some embodiments, $N_1$ is A. In some embodiments, $N_1$ is C. In some embodiments, $N_1$ is G. In some embodiments, $N_1$ is U.

In some embodiments, a $(^{m7}G^{3'OMe})(5')ppp(5')(N_1{}^{2'OMe})$ Cap1 structure comprises a second nucleotide, $N_2$ which is a cap proximal nucleotide at position 2 and is chosen from A, G, C, or U $(^{m7}G^{3'OMe})(5')ppp(5')(N_1{}^{2'OMe})pN_2)$. In some embodiments, $N_2$ is A. In some embodiments, $N_2$ is C. In some embodiments, $N_2$ is G. In some embodiments, $N_2$ is U.

In some embodiments, a Cap1 structure is or comprises $(^{m7}G^{3'OMe})(5')ppp(5')(A_1{}^{2'OMe})pG_2$ wherein $A_1$ is a cap proximal A at position +1 and $G_2$ is a cap proximal G at position +2, and has the following structure:

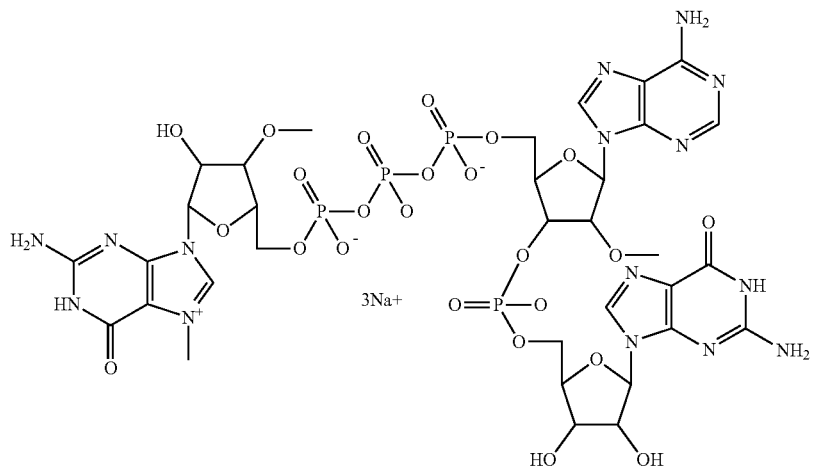 [SMILES: COC1C(COP(=O)(O)OP(=O)(O)OP(=O)(O)OCC2OC(n3cnc4c(N)ncnc43)C(OC)C2OP(=O)(O)OCC2OC(n3cnc4c(=O)[nH]c(N)nc43)C(O)C2O)OC(n2c[n+](C)c3c(=O)[nH]c(N)nc32)C1O]

In some embodiments, a Cap1 structure is or comprises $(^{m7}G^{3'OMe})(5')ppp(5')(G_1{}^{2'OMe})pG_2$ wherein $G_1$ is a cap proximal G at position +1 and $G_2$ is a cap proximal G at position +2, and has the following structure:

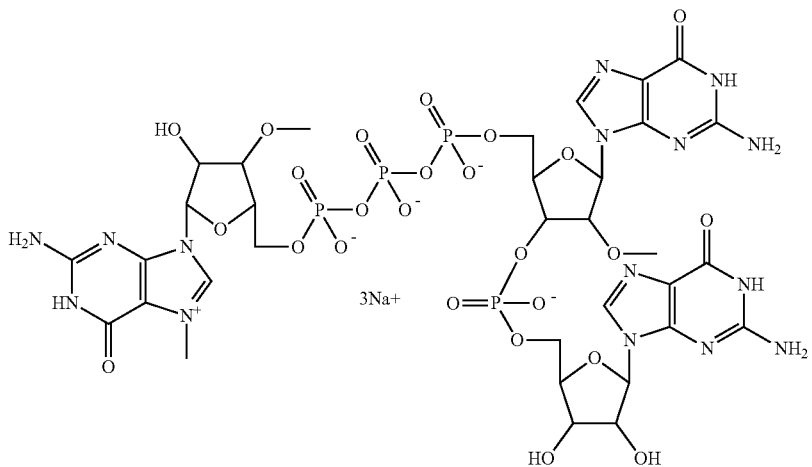 [SMILES: COC1C(COP(=O)(O)OP(=O)(O)OP(=O)(O)OCC2OC(n3cnc4c(=O)[nH]c(N)nc43)C(OC)C2OP(=O)(O)OCC2OC(n3cnc4c(=O)[nH]c(N)nc43)C(O)C2O)OC(n2c[n+](C)c3c(=O)[nH]c(N)nc32)C1O]

In some embodiments, a second nucleotide in a Cap1 structure can comprise one or more modifications, e.g., methylation. In some embodiments, a Cap1 structure comprising a second nucleotide comprising a 2'O methylation is a Cap2 structure.

In some embodiments, an RNA polynucleotide comprising a Cap1 structure has increased translation efficiency, increased translation rate and/or increased expression of an encoded payload relative to an appropriate reference comparator. In some embodiments, an RNA polynucleotide comprising a Cap1 structure having $(^{m7}G^{3'OMe})(5')ppp(5')(A_1^{2'OMe})pG_2$ wherein $A_1$ is a cap proximal nucleotide at position +1 and $G_2$ is a cap proximal nucleotide at position +2, has increased translation efficiency relative to an RNA polynucleotide comprising a Cap1 structure having $(^{m7}G^{3'OMe})(5')ppp(5')(G_1^{2'OMe})pG_2$ wherein $G_1$ is a cap proximal nucleotide at position 1 and $G_2$ is a cap proximal nucleotide at position 2. In some embodiments, increased translation efficiency is assessed upon administration of an RNA polynucleotide to a cell or an organism.

In some embodiments, a cap analog used in an RNA polynucleotide is $^{m7}G^{3'OMe}Gppp(m1^{2'-OMe})ApG$ (also sometimes referred to as m2$^{7,3'-OMe}$G(5')ppp(5')m$^{2'-OMe}$ApG or $(^{m7}G^{3'OMe})(5')ppp(5')(A^{2'OMe})pG$), which has the following structure:

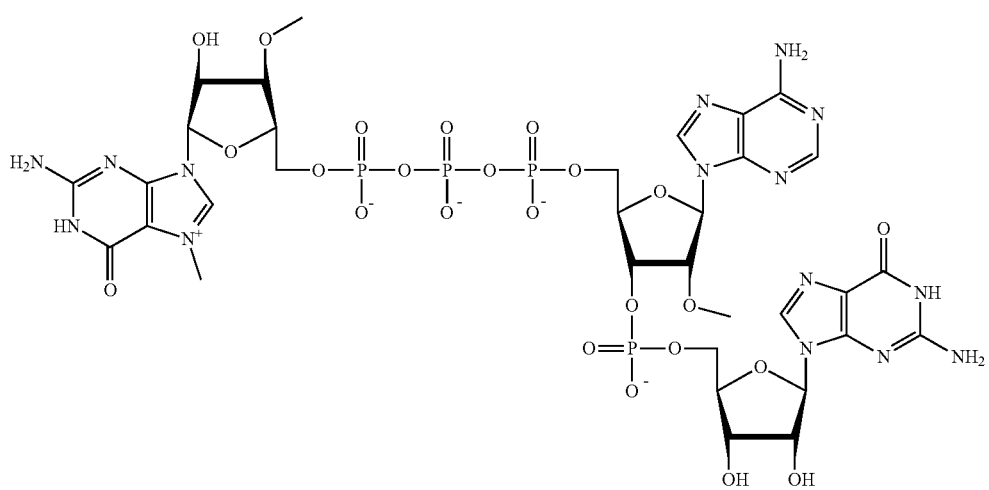

Below is an exemplary Cap1 RNA, which comprises RNA and m2$^{7,3'OMe}$G (5')ppp(5')m$^{2'-OMe}$ApG:
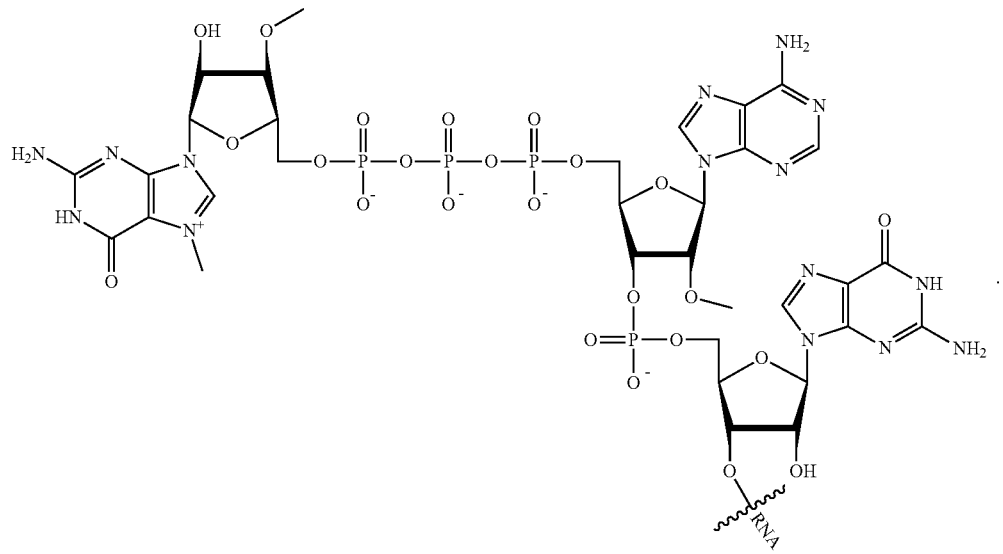
Below is another exemplary Cap1 RNA:
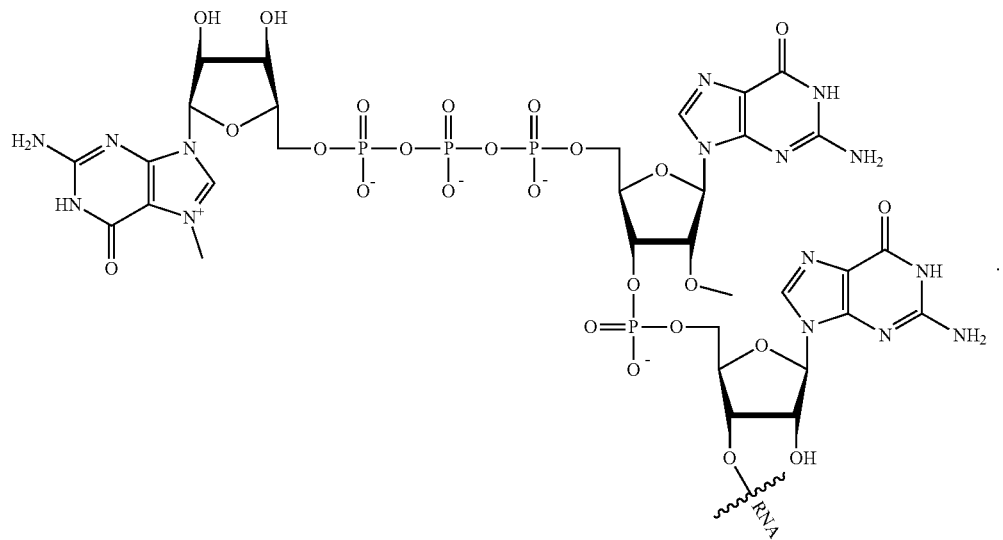
Below is an exemplary ARCA:
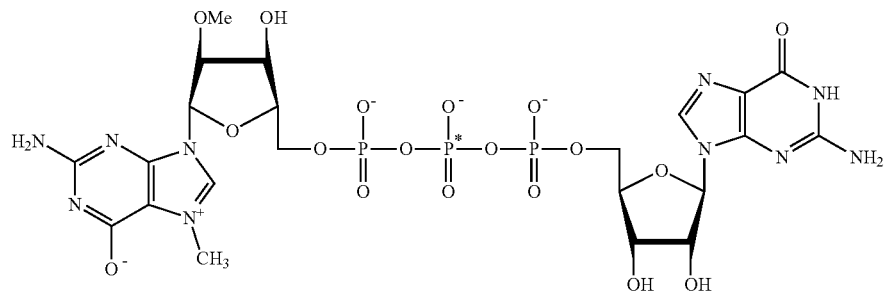

5'-UTR and Proximal Sequences

In some embodiments, a nucleic acid (e.g., DNA, RNA) utilized in accordance with the present disclosure comprises a 5'-UTR. In some embodiments, 5'-UTR may comprise a plurality of distinct sequence elements; in some embodiments, such plurality may be or comprise multiple copies of one or more particular sequence elements (e.g., as may be from a particular source or otherwise known as a functional or characteristic sequence element). In some embodiments, a 5' UTR comprises multiple different sequence elements.

The term "untranslated region" or "UTR" is commonly used in the art to a region in a DNA molecule which is transcribed but is not translated into an amino acid sequence, or to the corresponding region in an RNA polynucleotide, such as an mRNA molecule. An untranslated region (UTR) can be present 5' (upstream) of an open reading frame (5'-UTR) and/or 3' (downstream) of an open reading frame (3'-UTR). A 5'-UTR, if present, is located at the 5' end, upstream of the start codon of a polypeptide- (e.g., protein)-encoding region. A 5'-UTR is downstream of the 5'-cap (if present), e.g., directly adjacent to the 5'-cap.

In some embodiments of the disclosure, a 5' UTR is a heterologous 5' UTR, i.e., is a 5' UTR found in nature associated with a different ORF. In another embodiment, a 5' UTR is a synthetic 5' UTR, i.e., does not occur in nature. In some embodiments, aynthetic 5' UTR may be utilized, such as a 5' UTR whose sequence has been altered relative to a parental reference 5' UTR. Those skilled in the art will be aware of various 5' UTR sequence alterations that, for example, may have been reported to increase expression of an ORF with which the variant 5' UTR is associated.

To give but a few examples, in some embodiments, a utilized 5' UTRs may be or comprise a 5' UTR from a gene such as: α-globin or β-globin, such as Xenopus or human α-globin, β-globin, or oc-globin (e.g., as described, for example, in U.S. Pat. No. 8,278,063 and/or U.S. Pat. No. 9,012,219) genes, human cytochrome b-245 a polypeptide, hydroxysteroid (17b) dehydrogenase, Tobacco etch virus (e.g., as described, for example, in U.S. Pat. No. 8,278,063 and/or U.S. Pat. No. 9,012,219). CMV immediate-early 1 (IE1) gene (e.g., as described, for example, in US2014/0206753, WO2013/185069); HSD17B4, RPL32, ASAH1, ATP5A1, MP68, NDUFA4, NOSIP, RPL31, SLC7A3, TUBB4B, UBQLN2, PSMB3, RPS9, CASP1, COX6B1, NDUFA1, Rpl31, GNAS, ALB7. In some embodiments, a 5' UTR is or comprises a 5' UTR from an α-globin gene, or a variant thereof.

In some embodiments, embodiment utilized 5' UTR is a 5' UTR of a TOP gene, for example a 5' UTR of a TOP gene lacking the 5' TOP motif (the oligopyrimidine tract) (e.g., as described, for example, in WO/2015/101414, WO2015/101415, WO/2015/062738, WO2015/024667, WO2015/024667); a 5' UTR element of a ribosomal protein Large 32 (L32) gene (e.g., as described, for example, in WO/2015/101414, WO2015/101415, WO/2015/062738), a 5' UTR element of an hydroxysteroid (17-β) dehydrogenase 4 gene (HSD17B4) (e.g., as described, for example, in WO2015/024667), or a 5' UTR element of ATP5A1 (e.g., as described, for example, in WO2015/024667) can be used.

In some embodiments, an internal ribosome entry site (IRES) is used instead of or in addition to a 5' UTR.

In some embodiments, a 5' UTR utilized in accordance with the present disclosure is or comprises a sequence: gggaaauaag agagaaaaga agaguaagaa gaaauauaag accccggcgc cgccacc (SEQ ID NO: 21). In some embodiments, a 5' UTR utilized in accordance with the present disclosure is or comprises a sequence: gggaaauaag agagaaaaga agaguaagaa gaaauauaag agccacc (SEQ ID NO: 22). In some embodiments, a 5' UTR may be or comprise a sequence GGGAUCCUACC (SEQ ID NO: 23) (see, e.g., WO2014/144196). In some embodiments, a 5' UTR may be or comprise a sequence as set forth in one of SEQ ID NOs: 231-252, or 22848-22875 of WO2021/156267, or a fragment or a variant of any of the foregoing. In some embodiments, a 5' UTR may be or comprise a sequence as set forth in claim 9 of and/or of one or more of SEQ ID NOs: 1-20 of WO2019/077001 A1, or a fragment or variant of any of the foregoing. In some embodiments, a 5' UTR may be or comprise one set forth in WO2013/143700, for example one or more of SEQ ID NOs: 1-1363, SEQ ID NO: 1395, SEQ ID NO: 1421 and SEQ ID NO: 1422 of WO2013/143700, or a fragment or variant of any of the foregoing. In some embodiments, a 5'-UTR is or comprises a 5' UTR as described in WO2016/107877, for example in SEQ ID NOs: 25-30 or 319-382 of WO2016/107877, or fragments or variants of any of the foregoing. In some embodiments, a 5'-UTR is or comprises a 5' UTR as described in WO2017/036580 for example in SEQ ID NOs: 1-151 of WO2017/036580, or fragments or variants of any of the foregoing. In some embodiments, a 5' UTR is or comprises a 5'-UTR as described in WO2016/022914, for example in SEQ ID NOs: 3-19 of WO2016/022914, or fragments or variants of any of the foregoing In some embodiments, a 5' UTR may comprise a first polynucleotide fragment and a second polynucleotide fragment from the source and/or from different sources (see, for example, the 5' UTRs described in US Patent Application Publication No. 2010/0293625 and PCT/US2014/069155). In some embodiments, a 5' UTR utilized in accordance with the present disclosure comprises a cap proximal sequence, e.g., as disclosed herein. In some embodiments, a cap proximal sequence comprises a sequence adjacent to a 5' cap. In some embodiments, a cap proximal sequence comprises nucleotides in positions +1, +2, +3, +4, and/or +5 of an RNA polynucleotide.

In some embodiments, a Cap structure comprises one or more polynucleotides of a cap proximal sequence. In some embodiments, a Cap structure comprises an m7 Guanosine cap and nucleotide +1 (N1) of an RNA polynucleotide. In some embodiments, a Cap structure comprises an m7 Guanosine cap and nucleotide +2 (N2) of an RNA polynucleotide. In some embodiments, a Cap structure comprises an m7 Guanosine cap and nucleotides +1 and +2 (N1 and N2) of an RNA polynucleotide.

Those skilled in the art, reading the present disclosure, will appreciate that, in some embodiments, one or more residues of a cap proximal sequence (e.g., one or more of residues +1, +2, +3, +4, and/or +5) may be included in an RNA by virtue of having been included in a cap entity that (e.g., a Cap1 structure, etc.); alternatively, in some embodiments, at least some of the residues in a cap proximal sequence may be enzymatically added (e.g., by a polymerase such as a T7 polymerase). For example, in certain exemplified embodiments where a m2$^{7,3'\text{-}O}$Gppp(m1$^{2'\text{-}O}$)ApG cap is utilized, +1 and +2 are the (m1$^{2'\text{-}O}$)A and G residues of the cap, and +3, +4, and +5 are added by polymerase (e.g., T7 polymerase).

In some embodiments, a cap proximal sequence comprises N1 and N2 of a Cap structure, wherein N1 and N2 are any nucleotide, e.g., A, C, G or U. In some embodiments, N1 is A. In some embodiments, N1 is C. In some embodiments, N1 is G. In some embodiments, N1 is U. In some embodiments, N2 is A. In some embodiments, N2 is C. In some embodiments, N2 is G. In some embodiments, N2 is U.

In some embodiments, N1 is A and N2 is A. In some embodiments, N1 is A and N2 is C. In some embodiments, N1 is A and N2 is G. In some embodiments, N1 is A and N2 is U.

In some embodiments, N1 is C and N2 is A. In some embodiments, N1 is C and N2 is C. In some embodiments, N1 is C and N2 is G. In some embodiments, N1 is C and N2 is U.

In some embodiments, N1 is G and N2 is A. In some embodiments, N1 is G and N2 is C. In some embodiments, N1 is G and N2 is G. In some embodiments, N1 is G and N2 is U.

In some embodiments, N1 is U and N2 is A. In some embodiments, N1 is U and N2 is C. In some embodiments, N1 is U and N2 is G. In some embodiments, N1 is U and N2 is U.

In some embodiments, a cap proximal sequence comprises N1 and N2 of a Cap structure and N3, N4 and N5, wherein N1 to N5 correspond to positions +1, +2, +3, +4, and/or +5 of an RNA polynucleotide.

In some embodiments, N1, N2, N3, N4, or N5 are any nucleotide, e.g., A, C, G or U. In some embodiments, N1 is A and N2 is G. In some embodiments, N3 is A. In some embodiments, N4 is A. In some embodiments, N5 is A.

In some embodiments, N1, N2, N3, N4, or N5 are any nucleotide, e.g., A, C, G or U. In some embodiments, N1 is A and N2 is G. In some embodiments, N3 is A. In some embodiments, N4 is C. In some embodiments, N5 is A.

In some embodiments, N1, N2, N3, N4, or N5 are any nucleotide, e.g., A, C, G or U. In some embodiments, N1 is A and N2 is G. In some embodiments, N3 is A. In some embodiments, N4 is G. In some embodiments, N5 is A.

In some embodiments, N1, N2, N3, N4, or N5 are any nucleotide, e.g., A, C, G or U. In some embodiments, N1 is A and N2 is G. In some embodiments, N3 is A. In some embodiments, N4 is U. In some embodiments, N5 is A.

In some embodiments, N1, N2, N3, N4, or N5 are any nucleotide, e.g., A, C, G or U. In some embodiments, N1 is A and N2 is G. In some embodiments, N3 is A. In some embodiments, N4 is A. In some embodiments, N5 is G.

In some embodiments, N1, N2, N3, N4, or N5 are any nucleotide, e.g., A, C, G or U. In some embodiments, N1 is A and N2 is G. In some embodiments, N3 is A. In some embodiments, N4 is G. In some embodiments, N5 is G.

In some embodiments, N1, N2, N3, N4, or N5 are any nucleotide, e.g., A, C, G or U. In some embodiments, N1 is A and N2 is G. In some embodiments, N3 is A. In some embodiments, N4 is C. In some embodiments, N5 is G.

In some embodiments, N1, N2, N3, N4, or N5 are any nucleotide, e.g., A, C, G or U. In some embodiments, N1 is A and N2 is G. In some embodiments, N3 is A. In some embodiments, N4 is U. In some embodiments, N5 is G.

In some embodiments, N1, N2, N3, N4, or N5 are any nucleotide, e.g., A, C, G or U. In some embodiments, N1 is A and N2 is G. In some embodiments, N3 is A. In some embodiments, N4 is A. In some embodiments, N5 is C.

In some embodiments, N1, N2, N3, N4, or N5 are any nucleotide, e.g., A, C, G or U. In some embodiments, N1 is A and N2 is G. In some embodiments, N3 is A. In some embodiments, N4 is C. In some embodiments, N5 is C.

In some embodiments, N1, N2, N3, N4, or N5 are any nucleotide, e.g., A, C, G or U. In some embodiments, N1 is A and N2 is G. In some embodiments, N3 is A. In some embodiments, N4 is G. In some embodiments, N5 is C.

In some embodiments, N1, N2, N3, N4, or N5 are any nucleotide, e.g., A, C, G or U. In some embodiments, N1 is A and N2 is G. In some embodiments, N3 is A. In some embodiments, N4 is U. In some embodiments, N5 is C.

In some embodiments, N1, N2, N3, N4, or N5 are any nucleotide, e.g., A, C, G or U. In some embodiments, N1 is A and N2 is G. In some embodiments, N3 is A. In some embodiments, N4 is A. In some embodiments, N5 is U.

In some embodiments, N1, N2, N3, N4, or N5 are any nucleotide, e.g., A, C, G or U. In some embodiments, N1 is A and N2 is G. In some embodiments, N3 is A. In some embodiments, N4 is C. In some embodiments, N5 is U.

In some embodiments, N1, N2, N3, N4, or N5 are any nucleotide, e.g., A, C, G or U. In some embodiments, N1 is A and N2 is G. In some embodiments, N3 is A. In some embodiments, N4 is G. In some embodiments, N5 is U.

In some embodiments, N1, N2, N3, N4, or N5 are any nucleotide, e.g., A, C, G or U. In some embodiments, N1 is A and N2 is G. In some embodiments, N3 is A. In some embodiments, N4 is U. In some embodiments, N5 is U.

In some embodiments, N1, N2, N3, N4, or N5 are any nucleotide, e.g., A, C, G or U. In some embodiments, N1 is A and N2 is G. In some embodiments, N3 is C. In some embodiments, N4 is A. In some embodiments, N5 is A.

In some embodiments, N1, N2, N3, N4, or N5 are any nucleotide, e.g., A, C, G or U. In some embodiments, N1 is A and N2 is G. In some embodiments, N3 is C. In some embodiments, N4 is C. In some embodiments, N5 is A.

In some embodiments, N1, N2, N3, N4, or N5 are any nucleotide, e.g., A, C, G or U. In some embodiments, N1 is A and N2 is G. In some embodiments, N3 is C. In some embodiments, N4 is G. In some embodiments, N5 is A.

In some embodiments, N1, N2, N3, N4, or N5 are any nucleotide, e.g., A, C, G or U. In some embodiments, N1 is A and N2 is G. In some embodiments, N3 is C. In some embodiments, N4 is U. In some embodiments, N5 is A.

In some embodiments, N1, N2, N3, N4, or N5 are any nucleotide, e.g., A, C, G or U. In some embodiments, N1 is A and N2 is G. In some embodiments, N3 is C. In some embodiments, N4 is A. In some embodiments, N5 is G.

In some embodiments, N1, N2, N3, N4, or N5 are any nucleotide, e.g., A, C, G or U. In some embodiments, N1 is A and N2 is G. In some embodiments, N3 is C. In some embodiments, N4 is G. In some embodiments, N5 is G.

In some embodiments, N1, N2, N3, N4, or N5 are any nucleotide, e.g., A, C, G or U. In some embodiments, N1 is A and N2 is G. In some embodiments, N3 is C. In some embodiments, N4 is C. In some embodiments, N5 is G.

In some embodiments, N1, N2, N3, N4, or N5 are any nucleotide, e.g., A, C, G or U. In some embodiments, N1 is A and N2 is G. In some embodiments, N3 is C. In some embodiments, N4 is U. In some embodiments, N5 is G.

In some embodiments, N1, N2, N3, N4, or N5 are any nucleotide, e.g., A, C, G or U. In some embodiments, N1 is A and N2 is G. In some embodiments, N3 is C. In some embodiments, N4 is A. In some embodiments, N5 is C.

In some embodiments, N1, N2, N3, N4, or N5 are any nucleotide, e.g., A, C, G or U. In some embodiments, N1 is A and N2 is G. In some embodiments, N3 is C. In some embodiments, N4 is C. In some embodiments, N5 is C.

In some embodiments, N1, N2, N3, N4, or N5 are any nucleotide, e.g., A, C, G or U. In some embodiments, N1 is A and N2 is G. In some embodiments, N3 is C. In some embodiments, N4 is G. In some embodiments, N5 is C.

In some embodiments, N1, N2, N3, N4, or N5 are any nucleotide, e.g., A, C, G or U. In some embodiments, N1 is A and N2 is G. In some embodiments, N3 is C. In some embodiments, N4 is U. In some embodiments, N5 is C.

In some embodiments, N1, N2, N3, N4, or N5 are any nucleotide, e.g., A, C, G or U. In some embodiments, N1 is A and N2 is G. In some embodiments, N3 is C. In some embodiments, N4 is A. In some embodiments, N5 is U.

In some embodiments, N1, N2, N3, N4, or N5 are any nucleotide, e.g., A, C, G or U. In some embodiments, N1 is A and N2 is G. In some embodiments, N3 is C. In some embodiments, N4 is C. In some embodiments, N5 is U.

In some embodiments, N1, N2, N3, N4, or N5 are any nucleotide, e.g., A, C, G or U. In some embodiments, N1 is A and N2 is G. In some embodiments, N3 is C. In some embodiments, N4 is G. In some embodiments, N5 is U.

In some embodiments, N1, N2, N3, N4, or N5 are any nucleotide, e.g., A, C, G or U. In some embodiments, N1 is A and N2 is G. In some embodiments, N3 is C. In some embodiments, N4 is U. In some embodiments, N5 is U.

In some embodiments, N1, N2, N3, N4, or N5 are any nucleotide, e.g., A, C, G or U. In some embodiments, N1 is A and N2 is G. In some embodiments, N3 is G. In some embodiments, N4 is A. In some embodiments, N5 is A.

In some embodiments, N1, N2, N3, N4, or N5 are any nucleotide, e.g., A, C, G or U. In some embodiments, N1 is A and N2 is G. In some embodiments, N3 is G. In some embodiments, N4 is C. In some embodiments, N5 is A.

In some embodiments, N1, N2, N3, N4, or N5 are any nucleotide, e.g., A, C, G or U. In some embodiments, N1 is A and N2 is G. In some embodiments, N3 is G. In some embodiments, N4 is G. In some embodiments, N5 is A.

In some embodiments, N1, N2, N3, N4, or N5 are any nucleotide, e.g., A, C, G or U. In some embodiments, N1 is A and N2 is G. In some embodiments, N3 is G. In some embodiments, N4 is U. In some embodiments, N5 is A.

In some embodiments, N1, N2, N3, N4, or N5 are any nucleotide, e.g., A, C, G or U. In some embodiments, N1 is A and N2 is G. In some embodiments, N3 is G. In some embodiments, N4 is A. In some embodiments, N5 is G.

In some embodiments, N1, N2, N3, N4, or N5 are any nucleotide, e.g., A, C, G or U. In some embodiments, N1 is A and N2 is G. In some embodiments, N3 is G. In some embodiments, N4 is G. In some embodiments, N5 is G.

In some embodiments, N1, N2, N3, N4, or N5 are any nucleotide, e.g., A, C, G or U. In some embodiments, N1 is A and N2 is G. In some embodiments, N3 is G. In some embodiments, N4 is C. In some embodiments, N5 is G.

In some embodiments, N1, N2, N3, N4, or N5 are any nucleotide, e.g., A, C, G or U. In some embodiments, N1 is A and N2 is G. In some embodiments, N3 is G. In some embodiments, N4 is U. In some embodiments, N5 is G.

In some embodiments, N1, N2, N3, N4, or N5 are any nucleotide, e.g., A, C, G or U. In some embodiments, N1 is A and N2 is G. In some embodiments, N3 is G. In some embodiments, N4 is A. In some embodiments, N5 is C.

In some embodiments, N1, N2, N3, N4, or N5 are any nucleotide, e.g., A, C, G or U. In some embodiments, N1 is A and N2 is G. In some embodiments, N3 is G. In some embodiments, N4 is C. In some embodiments, N5 is C.

In some embodiments, N1, N2, N3, N4, or N5 are any nucleotide, e.g., A, C, G or U. In some embodiments, N1 is A and N2 is G. In some embodiments, N3 is G. In some embodiments, N4 is G. In some embodiments, N5 is C.

In some embodiments, N1, N2, N3, N4, or N5 are any nucleotide, e.g., A, C, G or U. In some embodiments, N1 is A and N2 is G. In some embodiments, N3 is G. In some embodiments, N4 is U. In some embodiments, N5 is C.

In some embodiments, N1, N2, N3, N4, or N5 are any nucleotide, e.g., A, C, G or U. In some embodiments, N1 is A and N2 is G. In some embodiments, N3 is G. In some embodiments, N4 is A. In some embodiments, N5 is U.

In some embodiments, N1, N2, N3, N4, or N5 are any nucleotide, e.g., A, C, G or U. In some embodiments, N1 is A and N2 is G. In some embodiments, N3 is G. In some embodiments, N4 is C. In some embodiments, N5 is U.

In some embodiments, N1, N2, N3, N4, or N5 are any nucleotide, e.g., A, C, G or U. In some embodiments, N1 is A and N2 is G. In some embodiments, N3 is G. In some embodiments, N4 is G. In some embodiments, N5 is U.

In some embodiments, N1, N2, N3, N4, or N5 are any nucleotide, e.g., A, C, G or U. In some embodiments, N1 is A and N2 is G. In some embodiments, N3 is G. In some embodiments, N4 is U. In some embodiments, N5 is U.

In some embodiments, N1, N2, N3, N4, or N5 are any nucleotide, e.g., A, C, G or U. In some embodiments, N1 is A and N2 is G. In some embodiments, N3 is U. In some embodiments, N4 is A. In some embodiments, N5 is A.

In some embodiments, N1, N2, N3, N4, or N5 are any nucleotide, e.g., A, C, G or U. In some embodiments, N1 is A and N2 is G. In some embodiments, N3 is U. In some embodiments, N4 is C. In some embodiments, N5 is A.

In some embodiments, N1, N2, N3, N4, or N5 are any nucleotide, e.g., A, C, G or U. In some embodiments, N1 is A and N2 is G. In some embodiments, N3 is U. In some embodiments, N4 is G. In some embodiments, N5 is A.

In some embodiments, N1, N2, N3, N4, or N5 are any nucleotide, e.g., A, C, G or U. In some embodiments, N1 is A and N2 is G. In some embodiments, N3 is U. In some embodiments, N4 is U. In some embodiments, N5 is A.

In some embodiments, N1, N2, N3, N4, or N5 are any nucleotide, e.g., A, C, G or U. In some embodiments, N1 is A and N2 is G. In some embodiments, N3 is U. In some embodiments, N4 is A. In some embodiments, N5 is G.

In some embodiments, N1, N2, N3, N4, or N5 are any nucleotide, e.g., A, C, G or U. In some embodiments, N1 is A and N2 is G. In some embodiments, N3 is U. In some embodiments, N4 is G. In some embodiments, N5 is G.

In some embodiments, N1, N2, N3, N4, or N5 are any nucleotide, e.g., A, C, G or U. In some embodiments, N1 is A and N2 is G. In some embodiments, N3 is U. In some embodiments, N4 is C. In some embodiments, N5 is G.

In some embodiments, N1, N2, N3, N4, or N5 are any nucleotide, e.g., A, C, G or U. In some embodiments, N1 is A and N2 is G. In some embodiments, N3 is U. In some embodiments, N4 is U. In some embodiments, N5 is G.

In some embodiments, N1, N2, N3, N4, or N5 are any nucleotide, e.g., A, C, G or U. In some embodiments, N1 is A and N2 is G. In some embodiments, N3 is U. In some embodiments, N4 is A. In some embodiments, N5 is C.

In some embodiments, N1, N2, N3, N4, or N5 are any nucleotide, e.g., A, C, G or U. In some embodiments, N1 is A and N2 is G. In some embodiments, N3 is U. In some embodiments, N4 is C. In some embodiments, N5 is C.

In some embodiments, N1, N2, N3, N4, or N5 are any nucleotide, e.g., A, C, G or U. In some embodiments, N1 is A and N2 is G. In some embodiments, N3 is U. In some embodiments, N4 is G. In some embodiments, N5 is C.

In some embodiments, N1, N2, N3, N4, or N5 are any nucleotide, e.g., A, C, G or U. In some embodiments, N1 is A and N2 is G. In some embodiments, N3 is U. In some embodiments, N4 is U. In some embodiments, N5 is C.

In some embodiments, N1, N2, N3, N4, or N5 are any nucleotide, e.g., A, C, G or U. In some embodiments, N1 is A and N2 is G. In some embodiments, N3 is U. In some embodiments, N4 is A. In some embodiments, N5 is U.

In some embodiments, N1, N2, N3, N4, or N5 are any nucleotide, e.g., A, C, G or U. In some embodiments, N1 is A and N2 is G. In some embodiments, N3 is U. In some embodiments, N4 is C. In some embodiments, N5 is U.

In some embodiments, N1, N2, N3, N4, or N5 are any nucleotide, e.g., A, C, G or U. In some embodiments, N1 is A and N2 is G. In some embodiments, N3 is U. In some embodiments, N4 is G. In some embodiments, N5 is U.

In some embodiments, N1, N2, N3, N4, or N5 are any nucleotide, e.g., A, C, G or U. In some embodiments, N1 is A and N2 is G. In some embodiments, N3 is U. In some embodiments, N4 is U. In some embodiments, N5 is U.

In some embodiments, a 5' UTR disclosed herein comprises a cap proximal sequence, e.g., as disclosed herein. In some embodiments, a cap proximal sequence comprises a sequence adjacent to a 5' cap. In some embodiments, a cap proximal sequence comprises nucleotides in positions +1, +2, +3, +4, and/or +5 of an RNA polynucleotide.

In some embodiments, a Cap structure comprises one or more polynucleotides of a cap proximal sequence. In some embodiments, a Cap structure comprises an m7 Guanosine cap and nucleotide +1 (N1) of an RNA polynucleotide. In some embodiments, a Cap structure comprises an m7 Guanosine cap and nucleotide +2 (N2) of an RNA polynucleotide. In some embodiments, a Cap structure comprises an m7 Guanosine cap and nucleotides +1 and +2 (N1 and N2) of an RNA polynucleotide.

In some embodiments, N1 and N2 are each independently chosen from: A, C, G, or U. In some embodiments, N1 is A. In some embodiments, N1 is C. In some embodiments, N1 is G. In some embodiments, N1 is U. In some embodiments, N2 is A. In some embodiments, N2 is C. In some embodiments, N2 is G. In some embodiments, N2 is U.

In some embodiments, N1 and N2 are each independently chosen from: A, C, G, or U. In some embodiments, N1 is A. In some embodiments, N1 is C. In some embodiments, N1 is G. In some embodiments, N1 is U. In some embodiments, N2 is A. In some embodiments, N2 is C. In some embodiments, N2 is G. In some embodiments, N2 is U.

In some embodiments, N1 is A and N2 is A. In some embodiments, N1 is A and N2 is C. In some embodiments, N1 is A and N2 is G. In some embodiments, N1 is A and N2 is U.

In some embodiments, N1 is C and N2 is A. In some embodiments, N1 is C and N2 is C. In some embodiments, N1 is C and N2 is G. In some embodiments, N1 is C and N2 is U.

In some embodiments, N1 is G and N2 is A. In some embodiments, N1 is G and N2 is C. In some embodiments, N1 is G and N2 is G. In some embodiments, N1 is G and N2 is U.

In some embodiments, N1 is U and N2 is A. In some embodiments, N1 is U and N2 is C. In some embodiments, N1 is U and N2 is G. In some embodiments, N1 is U and N2 is U.

In some embodiments, a cap proximal sequence comprises N1 and N2 of a Cap structure, and a sequence comprising: A3A4X5. In some embodiments, N1 and N2 are each independently chosen from: A, C, G, or U. In some embodiments, N1 is A and N2 is G. In some embodiments, X5 is chosen from A, C, G or U. In some embodiments, X5 is A. In some embodiments, X5 is C. In some embodiments, X5 is G. In some embodiments, X5 is U.

In some embodiments, a cap proximal sequence comprises N1 and N2 of a Cap structure, and a sequence comprising: C3A4X5. In some embodiments, N1 and N2 are each independently chosen from: A, C, G, or U. In some embodiments, N1 is A and N2 is G. In some embodiments, X5 is chosen from A, C, G or U. In some embodiments, X5 is A. In some embodiments, X5 is C. In some embodiments, X5 is G. In some embodiments, X5 is U.

In some embodiments, a cap proximal sequence comprises N1 and N2 of a Cap structure, and a sequence comprising X3Y4X5. In some embodiments, N1 and N2 are each independently chosen from: A, C, G, or U. In some embodiments, N1 is A and N2 is G. In some embodiments, X3 and X5 is each independently chosen from A, C, G or U. In some embodiments, X3 and/or X5 is A. In some embodiments, X3 and/or X5 is C. In some embodiments, X3 and/or X5 is G. In some embodiments, X3 and/or X5 is U. In some embodiments, Y4 is not C. In some embodiments, Y4 is A. In some embodiments, Y4 is G. In some embodiments, Y4 is U.

In some embodiments, a cap proximal sequence comprises N1 and N2 of a Cap structure, and a sequence comprising X3Y4X5. In some embodiments, N1 and N2 are each independently chosen from: A, C, G, or U. In some embodiments, N1 is A and N2 is G. In some embodiments, X3 and X5 is each independently chosen from A, C, G or U. In some embodiments, X3 and/or X5 is A. In some embodiments, X3 and/or X5 is C. In some embodiments, X3 and/or X5 is G. In some embodiments, X3 and/or X5 is U. In some embodiments, Y4 is not G. In some embodiments, Y4 is A. In some embodiments, Y4 is C. In some embodiments, Y4 is U.

In some embodiments, a cap proximal sequence comprises N1 and N2 of a Cap structure, and a sequence comprising A3C4A5. In some embodiments, N1 and N2 are each independently chosen from: A, C, G, or U. In some embodiments, N1 is A and N2 is G.

In some embodiments, a cap proximal sequence comprises N1 and N2 of a Cap structure, and a sequence comprising A3U4G5. In some embodiments, N1 and N2 are each independently chosen from: A, C, G, or U. In some embodiments, N1 is A and N2 is G.

In some embodiments, a Cap structure comprises one or more polynucleotides of a cap proximal sequence. In some embodiments, a Cap structure comprises an m7 Guanosine cap and nucleotide +1 (N1) of an RNA polynucleotide. In some embodiments, a Cap structure comprises an m7 Guanosine cap and nucleotide +2 (N2) of an RNA polynucleotide. In some embodiments, a Cap structure comprises an m7 Guanosine cap and nucleotides +1 and +2 (N1 and N2) of an RNA polynucleotide.

In some embodiments, N1 and N2 are any nucleotide, e.g., A, C, G, or U. In some embodiments, N1 is A. In some embodiments, N1 is C. In some embodiments, N1 is G. In some embodiments, N1 is U. In some embodiments, N2 is A. In some embodiments, N2 is C. In some embodiments, N2 is G. In some embodiments, N2 is U.

In some embodiments, N1 and N2 are any nucleotide, e.g., A, C, G, or U. In some embodiments, N1 is A. In some embodiments, N1 is C. In some embodiments, N1 is G. In some embodiments, N1 is U. In some embodiments, N2 is A. In some embodiments, N2 is C. In some embodiments, N2 is G. In some embodiments, N2 is U.

In some embodiments, N1 is A and N2 is A. In some embodiments, N1 is A and N2 is C. In some embodiments, N1 is A and N2 is G. In some embodiments, N1 is A and N2 is U.

In some embodiments, N1 is C and N2 is A. In some embodiments, N1 is C and N2 is C. In some embodiments, N1 is C and N2 is G. In some embodiments, N1 is C and N2 is U.

In some embodiments, N1 is G and N2 is A. In some embodiments, N1 is G and N2 is C. In some embodiments, N1 is G and N2 is G. In some embodiments, N1 is G and N2 is U.

In some embodiments, N1 is U and N2 is A. In some embodiments, N1 is U and N2 is C. In some embodiments, N1 is U and N2 is G. In some embodiments, N1 is U and N2 is U.

In some embodiments, a cap proximal sequence comprises N1 and N2 of a Cap structure, and a sequence comprising: A3A4X5. In some embodiments, N1 and N2 are any nucleotide, e.g., A, C, G, or U. In some embodiments, N1 is A and N2 is G. In some embodiments, X5 is chosen from A, C, G or U. In some embodiments, X5 is A. In some embodiments, X5 is C. In some embodiments, X5 is G. In some embodiments, X5 is U.

In some embodiments, a cap proximal sequence comprises N1 and N2 of a Cap structure, and a sequence comprising: C3A4X5. In some embodiments, N1 and N2 are any nucleotide, e.g., A, C, G, or U. In some embodiments, N1 is A and N2 is G. In some embodiments, X5 is any nucleotide, e.g., A, C, G or U. In some embodiments, X5 is A. In some embodiments, X5 is C. In some embodiments, X5 is G. In some embodiments, X5 is U.

In some embodiments, a cap proximal sequence comprises N1 and N2 of a Cap structure, and a sequence comprising X3Y4X5. In some embodiments, N1 and N2 are any nucleotide, e.g., A, C, G, or U. In some embodiments, N1 is A and N2 is G. In some embodiments, X3 and X5 is any nucleotide, e.g., A, C, G or U. In some embodiments, X3 and/or X5 is A. In some embodiments, X3 and/or X5 is C. In some embodiments, X3 and/or X5 is G. In some embodiments, X3 and/or X5 is U. In some embodiments, Y4 is not C. In some embodiments, Y4 is A. In some embodiments, Y4 is G. In some embodiments, Y4 is U.

In some embodiments, a cap proximal sequence comprises N1 and N2 of a Cap structure, and a sequence comprising X3Y4X5. In some embodiments, N1 and N2 are any nucleotide, e.g., A, C, G, or U. In some embodiments, N1 is A and N2 is G. In some embodiments, X3 and X5 is any nucleotide, e.g., A, C, G or U. In some embodiments, X3 and/or X5 is A. In some embodiments, X3 and/or X5 is C. In some embodiments, X3 and/or X5 is G. In some embodiments, X3 and/or X5 is U. In some embodiments, Y4 is not G. In some embodiments, Y4 is A. In some embodiments, Y4 is C. In some embodiments, Y4 is U.

In some embodiments, a cap proximal sequence comprises N1 and N2 of a Cap structure, and a sequence comprising A3C4A5. In some embodiments, N1 and N2 are any nucleotide, e.g., A, C, G, or U. In some embodiments, N1 is A and N2 is G.

In some embodiments, a cap proximal sequence comprises N1 and N2 of a Cap structure, and a sequence comprising A3U4G5. In some embodiments, N1 and N2 are any nucleotide, e.g., A, C, G, or U. In some embodiments, N1 is A and N2 is G.

Exemplary 5' UTRs include a human alpha globin (hAg) 5'UTR or a fragment thereof, a TEV 5' UTR or a fragment thereof, a HSP70 5' UTR or a fragment thereof, or a c-Jun 5' UTR or a fragment thereof.

In some embodiments, an RNA disclosed herein comprises a hAg 5' UTR or a fragment thereof. 3' UTR In some embodiments, an RNA as described herein comprises a 3'-UTR. A "3'-untranslated region" or "3'-UTR" or "3'-UTR element" will be recognized and understood by the person of ordinary skill in the art. As is known in the art, a 3' UTR typically is a part of a nucleic acid molecule that is located 3' (i.e. downstream) of a coding sequence and is not translated into protein. In some embodiments, a 3'-UTR may located between a coding sequence and an (optional) terminal poly(A) sequence. In some embodiments, a 3'-UTR may comprise elements for controlling gene expression, such a what may be referred to as regulatory elements. Such regulatory elements may be or comprise, e.g., ribosomal binding sites, miRNA binding sites etc.

A 3'-UTR, if present, is located at the 3' end, downstream of the termination codon of a polypeptide- (e.g., protein-) encoding region, but the term "3'-UTR" does preferably not include the poly(A) sequence. Thus, the 3'-UTR is upstream of the poly(A) sequence (if present), e.g. directly adjacent to the poly(A) sequence.

In some embodiments, an RNA disclosed herein comprises a 3' UTR comprising an F element and/or an I element. In some embodiments, a 3' UTR or a proximal sequence thereto comprises a restriction site. In some embodiments, a restriction site is a BamHI site. In some embodiments, a restriction site is a XhoI site.

In some embodiments, an RNA construct comprises an F element. In some embodiments, a F element sequence is a 3'-UTR of amino-terminal enhancer of split (AES).

In some embodiments, an RNA disclosed herein comprises a 3' UTR having 99%, 98%, 97%, 96%, 95%, 90%, 85%, or 80% identity to a 3' UTR with the sequence comprising: CUGGUACUGCAUGCACGCAAUGC-UAGCUGCCCCUUUCCCGUCCUGGGUACCCCGA GUCUCCCCCGACCUCGGGUCCCAGGUAUGCUCC-CACCUCCACCUGCCCCACUCACC ACCUCUGC-UAGUUCCAGACACCUCCCAAGCACGCAGCAAUG-CAGCUCAAAACGCU UAGCCUAGCCACACCCC-CACGGGAAACAGCAGUGAUUAACCUUUAGCAA-UAAACG AAAGUUUAACUAAGCUAUACUAACCC-CAGGGUUGGUCAAUUUCGUGCCAGCCACA CC (SEQ ID NO: 20). In some embodiments, an RNA disclosed herein comprises a 3' UTR provided in SEQ ID NO: 60.

In some embodiments, a 3'UTR is an FI element as described in WO2017/060314.

To give but a few examples, in some embodiments, a utilized 3'UTR may be or comprise a 3'UTR from a gene such as globin UTRs, including *Xenopus* β-globin UTRs and human β-globin UTRs are known in the art (see, for example, U.S. Pat. Nos. 8,278,063, 9,012,219, US2011/0086907). In some embodiments, a modified β-globin construct with enhanced stability in some cell types may be utilized; such a construct has been reported as having been made by cloning two sequential human β-globin 3'UTRs head to tail (US2012/0195936, WO2014/071963). In addition α2-globin, α1-globin, UTRs and variants thereof are also known in the art (WO2015/101415, WO2015/024667). Exemplary 3' UTRs described in the mRNA constructs in the non-patent literature include those from CYBA (Ferizi et al., 2015) and albumin (Thess et al., 2015). In some embodiments, exemplary 3' UTRs include that of bovine or human growth hormone (wild type or modified) (WO2013/185069, US2014/0206753, WO2014152774), rabbit R globin and hepatitis B virus (HBV), α-globin 3' UTR and Viral VEEV 3' UTR sequences are also known in the art. In some embodiments, the sequence UUUGAAUU (WO2014/144196) is used. In some embodiments, 3' UTRs of human and/or mouse ribosomal protein are used. In some embodiments, examples include rps9 3'UTR (WO2015/101414), FIG. 4 (WO2015/101415), and human albumin 7 (WO2015/101415). In some embodiments, a nucleic acid comprises at least one heterologous 3'-UTR, wherein the at least one heterologous 3'-UTR comprises a nucleic acid sequence derived from a 3'-UTR of a gene selected from PSMB3, ALB7, alpha-globin (referred to as "muag"), CASP1, COX6B1, GNAS, NDUFA1 and RPS9, or from a homolog, a fragment or variant of any one of these genes.

In some embodiments, a utilized 3'UTR may be as exemplified, for example, in published PCT application WO2019/077001 A1, in particular, claim 9 of WO2019/077001 A1. In some embodiments, a 3' UTR may be or comprise one of SEQ ID Nos: 23-34 of WO2019/077001 A1, or a fragment or variant thereof). In some embodiments, a 3' UTR utilized in accordance with the present disclosure comprises a sequence: ugauaauagg cuggagccuc ggucuuugaa uaaagucuga guggggge (SEQ ID NO: 24). In some embodiments, a 3' UTR of the present disclosure comprises a sequence: ugauaauagg cuggagccuc gguggccaug cuucuugecc cuugggccuc cccccagece cuccuccccu uccugcacce guacccccgu gguc-uuugaa uaaagucuga guggggge (SEQ ID NO: 25). In some embodiments, a nucleic acid may comprise a 3'-UTR as described in WO2016/107877 In some embodiments, suitable 3'-UTRs are SEQ ID NOs: 1-24 and SEQ ID NOs: 49-318 of WO2016/107877, or fragments or variants of these sequences. In some embodiments, a 3'-UTR as described in WO2017/036580 may be utilized. In some embodiments, suitable 3'-UTRs are SEQ ID NOs: 152-204 of WO2017/036580, or fragments or variants of these sequences. In some embodiments a 3'-UTR as described in WO2016/022914 is utilized. In some embodiments, a 3'-UTRs is or comprises a sequence according to SEQ ID NOs: 20-36 of WO2016/022914, or fragments or variants of these sequences.

PolyA

In some embodiments, a polynucleotide (e.g., DNA, RNA) disclosed herein comprises a polyadenylate (PolyA) sequence, e.g., as described herein. In some embodiments, a PolyA sequence is situated downstream of a 3'-UTR, e.g., adjacent to a 3'-UTR.

As used herein, the term "poly(A) sequence" or "poly-A tail" refers to an uninterrupted or interrupted sequence of adenylate residues which is typically located at the 3'-end of an RNA polynucleotide. Poly(A) sequences are known to those of skill in the art and may follow the 3'-UTR in the RNAs described herein. An uninterrupted poly(A) sequence is characterized by consecutive adenylate residues. In nature, an uninterrupted poly(A) sequence is typical. In some embodiments, polynucleotides disclosed herein comprise an uninterrupted Poly(A) sequence. In some embodiments, polynucleotides disclosed herein comprise interrupted Poly(A) sequence. In some embodiments, RNAs disclosed herein can have a poly(A) sequence attached to the free 3'-end of the RNA by a template-independent RNA polymerase after transcription or a poly(A) sequence encoded by DNA and transcribed by a template-dependent RNA polymerase.

It has been demonstrated that a poly(A) sequence of about 120 A nucleotides has a beneficial influence on the levels of RNA in transfected eukaryotic cells, as well as on the levels of polypeptide (e.g., protein) that is translated from an open reading frame that is present upstream (5') of the poly(A) sequence (Holtkamp et al., 2006, Blood, vol. 108, pp. 4009-4017).

In some embodiments, a poly(A) sequence in accordance with the present disclosure is not limited to a particular length; in some embodiments, a poly(A) sequence is any length. In some embodiments, a poly(A) sequence comprises, essentially consists of, or consists of at least 10, at least 20, at least 30, at least 40, at least 80, or at least 100 and up to 1000, up to 500, up to 400, up to 300, up to 200, or up to 150 A nucleotides, and, in particular, about 120 A nucleotides. In this context, "essentially consists of" means that most nucleotides in the poly(A) sequence, typically at least 75%, at least 80%, at least 85%, at least 90%, at least 95%, at least 96%, at least 97%, at least 98%, or at least 99% by number of nucleotides in the poly(A) sequence are A nucleotides, but permits that remaining nucleotides are nucleotides other than A nucleotides, such as U nucleotides (uridylate), G nucleotides (guanylate), or C nucleotides (cytidylate). In this context, "consists of" means that all nucleotides in the poly(A) sequence, i.e., 100% by number of nucleotides in the poly(A) sequence, are A nucleotides. The term "A nucleotide" or "A" refers to adenylate.

In some embodiments, a poly(A) sequence is attached during RNA transcription, e.g., during preparation of in vitro transcribed RNA, based on a DNA template comprising repeated dT nucleotides (deoxythymidylate) in the strand complementary to the coding strand. The DNA sequence encoding a poly(A) sequence (coding strand) is referred to as poly(A) cassette.

In some embodiments, the poly(A) cassette present in the coding strand of DNA essentially consists of dA nucleotides, but is interrupted by a random sequence of the four nucleotides (dA, dC, dG, and dT). Such random sequence may be 5 to 50, 10 to 30, or 10 to 20 nucleotides in length. Such a cassette is disclosed in WO 2016/005324 A1, hereby incorporated by reference. Any poly(A) cassette disclosed in WO 2016/005324 A1 may be used in accordance with the present disclosure. A poly(A) cassette that essentially consists of dA nucleotides, but is interrupted by a random sequence having an equal distribution of the four nucleotides (dA, dC, dG, dT) and having a length of e.g., 5 to 50 nucleotides shows, on DNA level, constant propagation of plasmid DNA in *E. coli* and is still associated, on RNA level, with the beneficial properties with respect to supporting RNA stability and translational efficiency is encompassed. In some embodiments, the poly(A) sequence contained in an RNA polynucleotide described herein essentially consists of A nucleotides, but is interrupted by a random sequence of the four nucleotides (A, C, G, U). Such random sequence may be 5 to 50, 10 to 30, or 10 to 20 nucleotides in length.

In some embodiments, no nucleotides other than A nucleotides flank a poly(A) sequence at its 3'-end, i.e., the poly(A) sequence is not masked or followed at its 3'-end by a nucleotide other than A.

In some embodiments, the poly(A) sequence may comprise at least 20, at least 30, at least 40, at least 80, or at least 100 and up to 500, up to 400, up to 300, up to 200, or up to 150 nucleotides. In some embodiments, the poly(A) sequence may essentially consist of at least 20, at least 30, at least 40, at least 80, or at least 100 and up to 500, up to 400, up to 300, up to 200, or up to 150 nucleotides. In some embodiments, the poly(A) sequence may consist of at least 20, at least 30, at least 40, at least 80, or at least 100 and up to 500, up to 400, up to 300, up to 200, or up to 150 nucleotides. In some embodiments, the poly(A) sequence comprises at least 100 nucleotides. In some embodiments, the poly(A) sequence comprises about 150 nucleotides. In some embodiments, the poly(A) sequence comprises about 120 nucleotides.

In some embodiments, a poly A tail comprises a specific number of Adenosines, such as about 50 or more, about 60 or more, about 70 or more, about 80 or more, about 90 or more, about 100 or more, about 120, or about 150 or about 200. In some embodiments a poly A tail of a string construct may comprise 200 A residues or less. In some embodiments, a poly A tail of a string construct may comprise about 200 A residues. In some embodiments, a poly A tail of a string construct may comprise 180 A residues or less. In some embodiments, a poly A tail of a string construct may comprise about 180 A residues. In some embodiments, a poly A tail may comprise 150 residues or less.

In some embodiments, the poly(A) sequence may comprise about 10 to about 500 adenosine nucleotides, about 10 to about 200 adenosine nucleotides, about 40 to about 200 adenosine nucleotides, or about 40 to about 150 adenosine nucleotides. In some embodiments, the length of the poly(A) sequence may be at least about or even more than about 10, 50, 64, 75, 100, 200, 300, 400, or 500 adenosine nucleotides.

In some embodiments, the nucleic acid comprises at least one poly(A) sequence comprising about 30 to about 200 adenosine nucleotides. In some embodiments, the poly(A) sequence comprises about 64 adenosine nucleotides (A64). In some embodiments, the poly(A) sequence comprises about 100 adenosine nucleotides (A100). In some embodiments, the poly(A) sequence comprises about 150 adenosine nucleotides.

In some embodiments, the nucleic acid comprises at least one poly(A) sequence comprising about 100 adenosine nucleotides, wherein the poly(A) sequence is interrupted by non-adenosine nucleotides, preferably by 10 non adenosine nucleotides (A30-N10-A70).

Open Reading Frames

In some embodiments, an RNA produced in accordance with technologies provided herein comprises an Open Reading Frame (ORF), e.g., encoding a polypeptide of interest or encoding a plurality of polypeptides of interest. In some embodiments, an RNA produced in accordance with technologies provided herein comprises a plurality of ORFs (e.g., encoding a plurality of polypeptides). In some embodiments, an RNA produced in accordance with technologies herein comprises a single ORF that encodes a plurality of polypeptides. In some such embodiments, polypeptides are or comprise antigens or epitopes thereof (e.g., relevant antigens).

To give but some examples, in some embodiments, an encoded polypeptide may be or comprise an antigen or epitope thereof, so that, when expressed in a subject to which a provided RNA is administered, an immune response (e.g., characterized by antibodies and/or T cells specifically directed to the antigen or one or more epitopes thereof); in some such embodiments, an encoded polypeptide may be polyepitopic, for example including multiple polypeptide elements, each of which includes at least one epitope, linked to one another and optionally separated by linkers. As is understood in the art, in some embodiments, a polyepitopic construct may include individual epitopes found in different portions of the same protein in nature. Alternatively or additionally, in some embodiments, a polyepitopic construct may include individual epitopes found in different proteins in nature. Those skilled in the art will be aware of a variety of considerations relevant to selection of desirable polyepitopic constructs, and/or antigens and/or epitopes for inclusion therein, useful in accordance with the present disclosure (see, for example, WO2014082729, WO2012159754, WO2017173321, WO2014180659, WO20161283762, WO2017194610, WO2011143656, WO2015103037, Nielsen J S, et al. J Immunol Methods. 2010 Aug. 31; 360(1-2):149-56, "Polyepitope Vaccine Technology." Polyepitope Vaccine Technology—Creative Biolabs, www.creative-biolabs.cor/vaccine/polyepitope-vaccine-technology.htm., Li. L. et al. Genome Med 13, 56 (2021), Cafri G. et al. Journal of Clinical Investigation 130, 5976-5988 (2020), Khairkhah N. et al (2020) PLOS ONE 15(10: e0240577).

In some embodiments, a relevant antigen may be or comprise an infectious antigen (i.e., an antigen associated with an infectious agent such as an infectious virus, a bacterium, a fungus, etc.) and/or a cancer antigen (e.g., an antigen associated with a class of tumors or a specific tumor; in some embodiments, a cancer-associated antigen may be or comprise a neoantigen or neoepitope), or epitope thereof.

Alternatively or additionally, in some embodiments, an ORF may encode, for example, an antibody or portion (e.g., antigen-binding portion) thereof, an enzyme, a cytokine, a therapeutic protein, etc. (see, for example, WO2017186928, WO2017191274, U.S. Ser. No. 10/669,322, Dammes et al Trens Pharmacol Sci 4:755, 2020-10-01, Wang et al Nature Reviews Drug Discovery 19, 441-442 (2020), Damase et al Front. Bioeng. Biotechnol., 18 Mar. 2021).

In some embodiments, an ORF for use in accordance with the present disclosure encodes a polypeptide that includes a signal sequence, e.g., that is functional in mammalian cells.

In some embodiments, a utilized signal sequence is "intrinsic" in that it is, in nature, it is associated with (e.g., linked to) the encoded polypeptide.

In some embodiments, a utilized signal sequence is heterologous to the encoded polypeptide—e.g., is not naturally part of a polypeptide (e.g., protein) whose sequences are included in the encoded polypeptide.

In some embodiments, signal peptides are sequences, which are typically characterized by a length of about 15 to 30 amino acids.

In many embodiments, signal peptides are positioned at the N-terminus of an encoded polypeptide as described herein, without being limited thereto. In some embodiments, signal peptides preferably allow the transport of the polypeptide encoded by RNAs of the present disclosure with which they are associated into a defined cellular compartment, preferably the cell surface, the endoplasmic reticulum (ER) or the endosomal-lysosomal compartment.

In some embodiments, a signal sequence is selected from an S1S2 signal peptide (aa 1-19), an immunoglobulin secretory signal peptide (aa 1-22), an HSV-1 gD signal peptide (MGGAAARLGAVILFVVIVGLHGVRSKY (SEQ ID NO: 1)), an HSV-2 gD signal peptide (MGRLTSGVGTAALLVVAVGLRVVCA (SEQ ID NO: 2)); a human SPARC signal peptide, a human insulin isoform 1 signal peptide, a human albumin signal peptide, etc. Those skilled in the art will be aware of other secretory signal peptides such as, for example, as disclosed in WO2017/081082 (e.g., SEQ ID NOs: 1-1115 and 1728, or fragments variants thereof) and WO2019008001.

In some embodiments, an RNAsequence encodes an epitope that may comprise or otherwise be linked to a signal sequence (e.g., secretory sequence), such as those listed in Table 1, or at least a sequence having 1, 2, 3, 4, or 5 amino acid differences relative thereto. In some embodiments, a signal sequence such as MFVFLVLLPLVSSQCVNLT (SEQ ID NO: 4), or at least a sequence having 1, 2, 3, 4, or at the most 5 amino acid differences relative thereto is utilized. In some embodiments, a sequence such as MFVFLVLLPLVSSQCVNLT (SEQ ID NO: 4), or a sequence having 1, 2, 3, 4, or at the most 5 amino acid differences relative thereto, is utilized.

In some embodiments, a signal sequence is selected from those included in the Table 1 below and/or those encoded by the sequences in Table 2 below:

TABLE 1

Exemplary signal sequences

| SEQ ID NO: | Signal | Sequence (Amino Acid) |
|---|---|---|
| 1 | HSV-1 gD SP | MGGAAARLGAVILFVVIVGLHGVRSKY |
| 2 | HSV-2 gD SP | MGRLTSGVGTAALLVVAVGLRVVCA |
| 3 | HSV-2 | MGRLTSGVGTAALLVVAVGLRVVCAKYA |
| 4 | SARS-CoV-2-S | MFVFLVLLPLVSSQCVNLT |
| 5 | human Ig heavy chain signal peptide (huSec) | MDWIWRILFLVGAATGAHSQM |
| 6 | HuIgGk signal peptide | METPAQLLFLLLLWLPDTTG |
| 7 | IgE heavy chain epsilon-1 signal peptide | MDWTWILFLVAAATRVHS |
| 8 | Japanese encephalitis PRM signal sequence | MLGSNSGQRVVFTILLLLVAPAYS |
| 9 | VSVg protein signal sequence | MKCLLYLAFLFIGVNCA |
| 10 | | MDWTWILFLVAAATRVHS |
| 11 | | ETPAQLLFLLLLWLPDTTG |
| 12 | | MLGSNSGQRVVFTILLLLVAPAYS |
| 13 | | MKCLLYLAFLFIGVNCA |
| 14 | | MWLVSLAIVTACAGA |
| 15 | | MFVFLVLLPLVSSQC |

TABLE 2

Exemplary nucleotide sequences encoding signal sequences

| SEQ ID NO: | Signal | Sequence (Nucleotide) |
|---|---|---|
| 16 | HSV-1 gD SP wild-type | ATGGGGGGGCTGCCGCCAGGTTGGGGGCCGTGATTTTGT TTGTCGTCATAGTGGGCCTCCATGGGGTCCGCAGCAAATA T |
| 17 | HSV-1 gD SP optimized nucleotide sequence | ATGggaggagccGCCGCCagactgggaGCCGTGatcctgttcgtggtgatcGT GggactgCATggagtgagaAGCaagtac |
| 18 | SARS-CoV-2-S | ATGTTTGTGTTTCTTGTGCTGCTGCCTCTTGTGTCTTCTCAG TGTGTGAATTTGACA |
| 19 | human Ig heavy chain signal peptide (huSec) | ATGGATTGGATTTGGAGAATCCTGTTCCTCGTGGGAGCCG CTACAGGAGCCCACTCCCAGATG | heterologous multimerization element comprises a dimerization, trimerization or tetramerization element.

In some embodiments, a multimerization element is one described in WO2017/081082 (e.g., SEQ ID NOs: 1116-1167, or fragments or variants thereof).

Exemplary trimerization and tetramerization elements include, but are not limited to, engineered leucine zippers, fibritin foldon domain from enterobacteria phage T4, GCN4pII, GCN4-pII, and p53.

In some embodiments, a provided encoded polypeptide(s) is able to form a trimeric complex. For example, a utilized encoded polypeptide(s) may comprise a domain allowing formation of a multimeric complex, such as for example particular a trimeric complex of an amino acid sequence comprising an encoded polypeptide(s) as described herein. In some embodiments, a domain allowing formation of a multimeric complex comprises a trimerization domain, for example, a trimerization domain as described herein.

In some embodiments, an encoded polypeptide(s) can be modified by addition of a T4-fibritin-derived "foldon" trimerization domain, for example, to increase its immunogenicity.

In some embodiments, an RNAas described herein encodes a membrane association element (e.g., a heterologous membrane association element), such as a transmembrane domain.

A transmembrane domain can be N-terminal, C-terminal, or internal to an encoded polypeptide. A coding sequence of a transmembrane element is typically placed in frame (i.e., in the same reading frame), 5', 3', or internal to coding sequences of sequences (e.g., sequences encoding polypeptide(s)) with which it is to be linked.

In some embodiments, a transmembrane domain comprises or is a transmembrane domain of Hemagglutinin (HA) of Influenza virus, Env of HIV-1, equine infectious anaemia virus (EIAV), murine leukaemia virus (MLV), mouse mammary tumor virus, G protein of vesicular stomatitis virus (VSV), Rabies virus, or a seven transmembrane domain receptor.

Codon Optimization

In some embodiments, an ORF encoding polypeptide of the disclosure is codon optimized. Codon optimization In some embodiments, an RNAutilized as described herein encodes a multimerization element (e.g., a heterologous multimerization element). In some embodiments, a methods are known in the art. For example, an ORF of any one or more of the sequences provided herein may be codon optimized. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove polypeptide trafficking sequences; remove/add post translation modification sites in encoded polypeptide (e.g., glycosylation sites); add, remove or shuffle protein domains; insert or delete restriction sites; modify ribosome binding sites and mRNA degradation sites; adjust translational rates to allow the various domains of the polypeptide to fold properly; or reduce or eliminate problem secondary structures within the polynucleotide. Codon optimization tools, algorithms and services are known in the art—non limiting examples include services from GeneArt (Life Technologies), DNA2.0 (Menlo Park CA) and/or proprietary methods. In some embodiments, the open reading frame (ORF) sequence is optimized using optimization algorithms.

In some embodiments, a codon optimized sequence shares less than 95% sequence identity to a naturally-occurring or wild-type sequence ORF (e.g., a naturally-occurring or wild-type mRNA sequence encoding a polypeptide). In some embodiments, a codon optimized sequence shares less than 90% sequence identity to a naturally-occurring or wild-type sequence (e.g., a naturally-occurring or wild-type mRNA sequence encoding a polypeptide). In some embodiments, a codon optimized sequence shares less than 85% sequence identity to a naturally-occurring or wild-type sequence (e.g., a naturally-occurring or wild-type mRNA sequence encoding a polypeptide). In some embodiments, a codon optimized sequence shares less than 80% sequence identity to a naturally-occurring or wild-type sequence (e.g., a naturally-occurring or wild-type mRNA sequence encoding a polypeptide). In some embodiments, a codon optimized sequence shares less than 75% sequence identity to a naturally-occurring or wild-type sequence (e.g., a naturally-occurring or wild-type mRNA sequence encoding a polypeptide).

In some embodiments, a codon optimized sequence shares between 65% and 85% (e.g., between about 67% and about 85% or between about 67% and about 80%) sequence identity to a naturally-occurring or wild-type sequence (e.g., a naturally-occurring or wild-type mRNA sequence encoding a polypeptide). In some embodiments, a codon optimized sequence shares between 65% and 75% or about 80% sequence identity to a naturally-occurring or wild-type sequence (e.g., a naturally-occurring or wild-type mRNA sequence encoding a polypeptide).

In some embodiments, a codon-optimized sequence encodes polypeptide (e.g., an antigen) that is as immunogenic as, or more immunogenic than (e.g., at least 10%, at least 20%, at least 30%, at least 40%, at least 50%, at least 100%, or at least 200% more), than a polypeptide encoded by a non-codon-optimized sequence.

In some embodiments, when transfected into mammalian host cells, the modified mRNAs have a stability of between 12-18 hours, or greater than 18 hours, e.g., 24, 36, 48, 60, 72, or greater than 72 hours and are capable of being expressed by the mammalian host cells.

In some embodiments, a codon optimized RNA may be one in which the levels of G/C are enhanced and/or A/U are enhanced. In some embodiments, the G/C-content of nucleic acid molecules (e.g., mRNA) may influence the stability of the RNA. RNA having an increased amount of guanine (G) and/or cytosine (C) residues may be functionally more stable than RNA containing a large amount of adenine (A) and thymine (T) or uracil (U) nucleotides. As an example, WO02/098443 discloses a pharmaceutical composition containing an mRNA stabilized by sequence modifications in the translated region. In some embodiments, due to the degeneracy of the genetic code, the modifications work by substituting existing codons for those that promote, for example greater RNA stability, without changing the resulting amino acid. In some embodiments, the approach is limited to coding regions of the RNA.

Nucleotide Content

In some embodiments, an RNA and/or ORF as described herein comprises a particular composition of nucleotide triphosphates; in some embodiments, an RNA and/or ORF as described herein is not limited to comprise any particular composition of nucleotide triphosphates.

In some embodiments, an ORF and/or RNA molecule comprises a molar ratio of x total cytidine and/or one or more functional cytidine analog(s) to total guanosine and/or one or more functional guanosine analog(s). In some embodiments, an ORF and/or RNA molecule comprises a molar ratio y of total cytidine and/or one or more functional cytidine analog(s) to total uridine and/or one or more functional uridine analog(s). In some embodiments, an ORF and/or RNA molecule comprises a molar ratio z of total cytidine and/or one or more functional cytidine analog(s) to total adenosine and/or one or more functional adenosine analog(s). In some such embodiments, the molar ratio of x is 0.01, 0.02, 0.03, 0.04, 0.05, 0.06, 0.07, 0.08, 0.09, 0.1, 0.2, 0.3, 0.4, 0.5, 0.6 0.7, 0.8, 0.9, 1.0, 1.1, 1.2, 1.3, 1.4. 1.5, 1.6, 1.7, 1.8, 1.9, 2.0, 2.1, 2.2, 2.3, 2.4, 2.5, 2.6, 2.7, 2.8, 2.9 or 3.0. In some such embodiments, the molar ratio of y is 0.01, 0.02, 0.03, 0.04, 0.05, 0.06, 0.07, 0.08, 0.09, 0.1, 0.2, 0.3, 0.4, 0.5, 0.6 0.7, 0.8, 0.9, 1.0, 1.1, 1.2, 1.3, 1.4. 1.5, 1.6, 1.7, 1.8, 1.9, 2.0, 2.1, 2.2, 2.3, 2.4, 2.5, 2.6, 2.7, 2.8, 2.9 or 3.0. In some such embodiments, the molar ratio of y is 0.01, 0.02, 0.03, 0.04, 0.05, 0.06, 0.07, 0.08, 0.09, 0.1, 0.2, 0.3, 0.4, 0.5, 0.6 0.7, 0.8, 0.9, 1.0, 1.1, 1.2, 1.3, 1.4. 1.5, 1.6, 1.7, 1.8, 1.9, 2.0, 2.1, 2.2, 2.3, 2.4, 2.5, 2.6, 2.7, 2.8, 2.9 or 3.0. In some such embodiments, the molar ratio of z is 0.01, 0.02, 0.03, 0.04, 0.05, 0.06, 0.07, 0.08, 0.09, 0.1, 0.2, 0.3, 0.4, 0.5, 0.6 0.7, 0.8, 0.9, 1.0, 1.1, 1.2, 1.3, 1.4. 1.5, 1.6, 1.7, 1.8, 1.9, 2.0, 2.1, 2.2, 2.3, 2.4, 2.5, 2.6, 2.7, 2.8, 2.9 or 3.0.

In some embodiments, the relevant molar ratio in an RNA and/or ORF is different than that in the corresponding ratio in the reaction mixture.

In some embodiments, an ORF and/or RNA molecule comprises a nucleotide content of 15%, 20%, 25%, 30%, 35%, 40% or more ATP and/or one or more functional ATP analog(s). In some embodiments, an ORF and/or RNA molecule comprises a nucleotide content of 15%, 20%, 25%, 30%, 35%, 40% or more CTP and/or one or more functional CTP analog(s). In some embodiments, an ORF and/or RNA molecule comprises a nucleotide content of 15%, 20%, 25%, 30%, 35%, 40% or more GTP and/or one or more functional GTP analog(s). In some embodiments, an ORF and/or RNA molecule comprises a nucleotide content of 15%, 20%, 25%, 30%, 35%, 40% or more UTP and/or one or more functional UTP analog(s).

In some embodiments, an ORF and/or RNA molecule comprises a molar ratio v of total adenosine and/or one or more functional adenosine analog(s) to total guanosine and/or one or more functional guanosine analog(s). In some embodiments, an ORF and/or RNA molecule comprises a molar ratio w of total adenosine and/or one or more functional adenosine analog(s) to total uridine and/or one or more functional uridine analog(s). In some embodiments, an ORF and/or RNA molecule comprises a molar ratio q of total adenosine and/or one or more functional adenosine analog(s) to total cytidine and/or one or more functional cytidine analog(s). In some such embodiments, the molar ratio of v is 0.01, 0.02, 0.03, 0.04, 0.05, 0.06, 0.07, 0.08, 0.09, 0.1, 0.2, 0.3, 0.4, 0.5, 0.6 0.7, 0.8, 0.9, 1.0, 1.1, 1.2, 1.3, 1.4. 1.5, 1.6, 1.7, 1.8, 1.9, 2.0, 2.1, 2.2, 2.3, 2.4, 2.5, 2.6, 2.7, 2.8, 2.9 or 3.0. In some such embodiments, the molar ratio of w is 0.01, 0.02, 0.03, 0.04, 0.05, 0.06, 0.07, 0.08, 0.09, 0.1, 0.2, 0.3, 0.4, 0.5, 0.6 0.7, 0.8, 0.9, 1.0, 1.1, 1.2, 1.3, 1.4. 1.5, 1.6, 1.7, 1.8, 1.9, 2.0, 2.1, 2.2, 2.3, 2.4, 2.5, 2.6, 2.7, 2.8, 2.9 or 3.0. In some such embodiments, the molar ratio of q is 0.01, 0.02, 0.03, 0.04, 0.05, 0.06, 0.07, 0.08, 0.09, 0.1, 0.2, 0.3, 0.4, 0.5, 0.6 0.7, 0.8, 0.9, 1.0, 1.1, 1.2, 1.3, 1.4. 1.5, 1.6, 1.7, 1.8, 1.9, 2.0, 2.1, 2.2, 2.3, 2.4, 2.5, 2.6, 2.7, 2.8, 2.9 or 3.0.

Production

In some embodiments, technologies provided by the present disclosure achieve production of RNA compositions and/or preparations (e.g., pharmaceutical-grade RNA preparations including large batch preparations) by synthesizing RNA by IVT, e.g., in a bioreactor. In some embodiments, a composition and/or preparation comprising produced RNA comprises RNA at a particular concentration of at least 1 mg/mL (including, e.g., at least 1.5 mg/mL, at least 2 mg/mL, at least 2.5 mg/mL, at least 3 mg/mL, at least 3.5 mg/mL, at least 4 mg/mL, at least 4.5 mg/mL, at least 5 mg/mL, at least 6 mg/mL or higher). In some embodiments, produced RNA may be present at a concentration of 1.5 mg/mL to 5 mg/mL or 2 mg/mL to 4 mg/mL.

In some embodiments, RNA (e.g., therapeutic mRNA) is synthesized from a DNA template by IVT, e.g., in the presence of appropriate reagents comprising, e.g., at least one RNA-polymerase and appropriate nucleotide triphosphates or variants thereof (e.g., modified ribonucleotide triphosphates), e.g., in a bioreactor. In some embodiments, a bioreactor that is useful for IVT is large enough for an IVT reaction volume of at least 1 liter, including, e.g., at least 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 25, 30, 35, 40, 50 liters or more. In some embodiments, a bioreactor that is particularly useful for commercial scale IVT is large enough for an IVT reaction volume of at least 20 liters, including e.g., at least 25, 30, 40, 45, 50 liters, or more.

Exemplary Starting Materials

DNA Templates

One of ordinary skill in the art will understand that a nucleic acid template (e.g., DNA template) is used to direct synthesis of RNA (e.g., single-stranded RNA, e.g., therapeutic RNA). In some embodiments, a DNA template is a linear DNA molecule. In some embodiments, a DNA template is a circular DNA molecule. DNA can be obtained or generated using methods known in the art, including, e.g., gene synthesis, recombinant DNA technology, or a combination thereof. In some embodiments, a DNA template comprises a nucleotide sequence coding for a transcribed region of interest (e.g., coding for a RNA described herein) and a promoter sequence that is recognized by an RNA polymerase selected for use in IVT. In some embodiments, a DNA template comprises a nucleotide sequence coding for a plurality of transcribed regions of interest and a promoter sequence or sequences that are recognized by an RNA polymerase selected for use in IVT. Various RNA polymerases are known in the art, including, e.g., DNA dependent RNA polymerases (e.g., a T7 RNA polymerase, a T3 RNA polymerase, a SP6 RNA polymerase, a N4 virion RNA polymerase, or a variant or functional domain thereof). One of ordinary sill in the art will readily understand that an RNA polymerase utilized herein may be a recombinant RNA polymerase and/or a purified RNA polymerase, i.e., not as a part of a cell extract, which contains other components in addition to RNA polymerase(s), and/or may be a variant of a wild polymerase (e.g., sharing one or more characteristic sequence elements—e.g., sufficient to confer polymerization activity—with such wild-type polymerase, and/or sharing at least about 50%, 60%, 70%, 80%, 85%, 90%, 95%<96%, 97%, 98%, 99% or more sequence identity with such wild type polymerase). In some embodiments, a utilized polymerase is a commercially available polymerase (e.g., from a source such as ThermoFisher, New England Biolabs). One of ordinary skill in the art will recognize an appropriate promoter sequence for the selected RNA polymerase. In some embodiments, a DNA template comprises a promoter sequence for T7 RNA polymerase.

In some embodiments, a DNA template comprises a nucleotide sequence coding for an RNA described herein (e.g., comprising a nucleotide sequence coding for a polypeptide of interest and optionally comprising one or more nucleotide sequences coding for characteristic elements of an RNA described herein, including, e.g., polyA tail, 3' UTR, and/or 5' UTR, etc.). In some embodiments, such a coding sequence may be generated by gene synthesis. In some embodiments, such a coding sequence may be inserted into a vector by any appropriate cloning method known in the art (e.g., cold fusion cloning, Gibson assembly, etc.).

In some embodiments, a DNA template may further comprise one or more of a recognition sequence for an appropriate restriction endonuclease (e.g., utilized for linearization), an appropriate resistance gene, and/or an appropriate origin of replication. In some embodiments, a DNA template may further comprise a recognition sequence for an appropriate restriction endonuclease (e.g., utilized for linearization such as, e.g., but not limited to a Class II restriction endonuclease), an appropriate resistance gene (e.g., but not limited to a kanamycin resistance gene), and an appropriate origin of replication.

In some embodiments, a DNA template may be amplified via polymerase chain reaction (PCR) from a plasmid DNA. In some embodiments, a plasmid DNA may be obtained, e.g., from bacterial cells (e.g., *Escherichia coli* (*E. coli*)) followed by an endotoxin and animal product-free plasmid isolation procedure.

In some embodiments, a DNA template may be a linearized plasmid DNA (pDNA) template in the absence of PCR-based amplification. In some such embodiments, a cell bank or a cell stock for a pDNA of interest (e.g., as described herein) may be stablished. For example, in some embodiments, such a cell bank or a cell stock may comprise a frozen stock of bacterial cells (e.g., *E. coli* cells, such as DH10B *E. coli* cells) that are genetically engineered to comprise a pDNA template of interest (e.g., as described herein) with predetermined specifications. In some embodiments, a pDNA contains a promoter sequence (e.g. T7 RNA polymerase). In some embodiments, a pDNA contains a recognition sequence for an endonuclease (e.g., for linearization). In some embodiments, a pDNA contains a resistance gene. In some embodiments, a pDNA contains an origin of replication. In some embodiments, a pDNA contains one or more of a promoter sequence, a recognition sequence for an endonuclease, a resistance gene, and/or an origin of replication.

In some embodiments, a DNA template (e.g., a linear DNA template) concentration (g/L IVT starting volume) is at least about 0.05, 0.06, 0.07, 0.08, 0.09, 0.10, 0.11, 0.12, 0.13, 0.14, 0.15 g/L. In some embodiments, a DNA template (e.g., a linear DNA template) starting concentration is about 0.01-0.15, 0.02-0.14, 0.03-0.13, 0.04-0.12, 0.05-0.11, 0.06-0.11, 0.07-0.11, 0.08-0.11-0.09-0.11 g/L.

Ribonucleotides

Ribonucleotides for use in in vitro transcription may include at least two or more (e.g., at least three or more, at least four or more, at least five or more, at least six or more) different types of ribonucleotides, each type having a different nucleoside. Ribonucleotides for use in in vitro transcription can include unmodified and/or modified ribonucleotides. Unmodified ribonucleotides include the purine bases adenine (A) and guanine (G), and the pyrimidine bases cytosine (C) and uracil (U). In some embodiments, all four types of unmodified ribonucleotides may be used for in vitro transcription.

In some embodiments, at least one type of ribonucleotide included in in vitro transcription is a modified ribonucleotide. Modified ribonucleotides may include one or more modifications including, but not limited to, for example, (a) end modifications, e.g., 5' end modifications (e.g., phosphorylation, dephosphorylation, conjugation, inverted linkages, etc.), 3' end modifications (e.g., conjugation, inverted linkages, etc.), (b) base modifications, e.g., replacement with modified bases, stabilizing bases, destabilizing bases, or bases that base pair with an expanded repertoire of partners, or conjugated bases, (c) sugar modifications (e.g., at the 2' position or 4' position) or replacement of the sugar, and (d) internucleoside linkage modifications, including modification or replacement of the phosphodiester linkages. To the extent that such modifications interfere with translation (e.g., results in a reduction of 50% or more in translation relative to the absence of the modification—e.g., as characterized using a rabbit reticulocyte in vitro translation assay), such modified ribonucleotides, in some embodiments, are not desirable for use in systems and methods described herein.

In some embodiments, a modified ribonucleotide may have at least one nucleoside ("base") modification or substitution. Various nucleoside modifications or substitutions are known in the art; one of skill in the art will appreciate that modified nucleosides include, for example, but not limited to synthetic and natural nucleobases such as inosine, xanthine, hypoxanthine, nubularine, isoguanisine, tubercidine, 2-(halo)adenine, 2-(alkyl)adenine, 2-(propyl)adenine, 2-(amino)adenine, 2-(aminoalkyll)adenine, 2-(aminopropyl)adenine, 2-(methylthio)-N6-(isopentenyl)adenine, 6-(alkyl)adenine, 6-(methyl)adenine, 7-(deaza)adenine, 8-(alkenyl)adenine, 8-(alkyl)adenine, 8-(alkynyl)adenine, 8-(amino)adenine, 8-(halo)adenine, 8-(hydroxyl)adenine, 8-(thioalkyl)adenine, 8-(thiol)adenine, N6-(isopentyl)adenine, N6-(methyl) adenine, N6, N6-(dimethyl)adenine, 2-(alkyl)guanine, 2-(propyl)guanine, 6-(alkyl)guanine, 6-(methyl)guanine, 7-(alkyl)guanine, 7-(methyl)guanine, 7-(deaza)guanine, 8-(alkyl)guanine, 8-(alkenyl)guanine, 8-(alkynyl)guanine, 8-(amino)guanine, 8-(halo)guanine, 8-(hydroxyl)guanine, 8-(thioalkyl)guanine, 8-(thiol)guanine, N-(methyl)guanine, 2-(thio)cytosine, 3-(deaza)-5-(aza)cytosine, 3-(alkyl)cytosine, 3-(methyl)cytosine, 5-(alkyl)cytosine, 5-(alkynyl)cytosine, 5-(halo)cytosine, 5-(methyl)cytosine, 5-(propynyl)cytosine, 5-(propynyl)cytosine, 5-(trifluoromethyl)cytosine, 6-(azo)cytosine, N4-(acetyl)cytosine, 3-(3 amino-3 carboxypropyl)uracil, 2-(thio)uracil, 5-(methyl)-2-(thio)uracil, 5-(methylaminomethyl)-2 (thio)uracil, 4-(thio)uracil, 5-(methyl)-4 (thio)uracil, 5-(methylaminomethyl)-4 (thio)uracil, 5-(methyl)-2,4-(dithio)uracil, 5-(methylaminomethyl)-2,4 (dithio)uracil, 5-(2-aminopropyl)uracil, 5-(alkyl)uracil, 5-(alkynyl)uracil, 5-(allylamino)uracil, 5-(aminoallyl)uracil, 5-(aminoalkyl) uracil, 5-(guanidiniumalkyl)uracil, 5-(1,3-diazole-lalkyl) uracil, 5-(cyanoalkyl)uracil, 5-(dialkylaminoalkyl)uracil, 5-(dimethylaminoalkyl)uracil, 5-(halo)uracil, 5-(methoxy) uracil, uracil-5-oxyacetic acid, 5-(methoxycarbonylmethyl)-2-(thio)uracil, 5-(methoxycarbonyl-methyl)uracil, 5-(propynyl)uracil, 5-(propynyl)uracil, 5-(trifluoromethyl)uracil, 6-(azo)uracil, dihydrouracil, N3-(methyl)uracil, 5-uracil (i.e., pseudouracil), 2-(thio)pseudouracil, 4-(thio)pseudouracil, 2,4-(dithio)psuedouracil, 5-(alkyl)pseudouracil, 5-(methyl)pseudouracil, 5-(alkyl)-2-(thio)pseudouracil, 5-(methyl)-2-(thio)pseudouracil, 5-(alkyl)-4 (thio)pseudouracil, 5-(methyl)-4 (thio)pseudouracil, 5-(alkyl)-2,4 (dithio) pseudouracil, 5-(methyl)-2,4 (dithio)pseudouracil, 1-substituted pseudouracil (e.g., 1-methyl-pseudouridine), C-5 propynyl-uridine, 2-aminoadenosine, C5-bromouridine, C5-fluorouridine, C5-iodouridine, C5-propynyl-uridine, 1-substituted-2(thio)-pseudouracil, 1-substituted 4 (thio) pseudouracil, 1-substituted 2,4-(dithio)pseudouracil, 1-(aminocarbonylethylenyl)-pseudouracil, 1-(aminocarbonylethylenyl)-2(thio)-pseudouracil, 1 (aminocarbonylethylenyl)-4 (thio)pseudouracil, 1-(aminocarbonylethylenyl)-2,4-(dithio)pseudouracil, 1-(aminoalkylaminocarbonylethylenyl)-pseudouracil, 1 (aminoalkylamino-carbonylethylenyl)-2(thio)-pseudouracil, 1-(arninoalkylaminocarbonylethylenyl)-4 (thio)pseudouracil, 1-(arninoalkylaminocarbonylethylenyl)-2,4-(dithio)pseudouracil, 1,3-(diaza)-2-(oxo)-phenoxazin-1-yl, 1-(aza)-2-(thio)-3-(aza)-phenoxazin-1-yl, 1,3-(diaza)-2-(oxo)-phenthiazin-lyl, 1-(aza)-2-(thio)-3-(aza)-phenthiazin-1-yl, 7-substituted 1,3-(diaza)-2-(oxo)-phenoxazin-lyl, 7-substituted 1-(aza)-2-(thio)-3-(aza)-phenoxazin-1-yl, 7-substituted 1,3-(diaza)-2-(oxo)-phenthiazin-1-yl, 7-substituted 1-(aza)-2-(thio)-3-(aza)-phenthiazin-1-yl, 7-(aminoalkylhydroxy)-1,3-(diaza)-2-(oxo)-phenoxazin-1-yl, 7-(aminoalkylhydroxy)-1-(aza)-2-(thio)-3-(aza)-phenoxazin-1-yl, 7-(aminoalkylhydroxy)-1,3-(diaza)-2-(oxo)-phenthiazin-1-yl, 7-(aminoalkylhydroxy)-1-(aza)-2-(thio)-3-(aza)-phenthiazin-1-yl, 7-(guanidiniumalkylhydroxy)-1,3-(diaza)-2-(oxo)-phenoxazin-1-yl, 7-(guanidiniumalkylhydroxy)-1-(aza)-2-(thio)-3-(aza)-phenoxazin-1-yl, 7-(guanidiniumalkylhydroxy)-1,3-(diaza)-2-(oxo)-phenthiazin-1-yl, 7-(guanidiniumalkylhydroxy)-1-(aza)-2-(thio)-3-(aza)-phenthiazin-1-yl, 1,3,5-(triaza)-2,6-(dioxa)-naphthalene, inosine, xanthine, hypoxanthine, nubularine, tubercidine, isoguanisine, inosinyl, 2-aza-inosinyl, 7-deazainosinyl, nitroimidazolyl, nitropyrazolyl, nitrobenzimidazolyl, nitroindazolyl, aminoindolyl, pyrrolopyrimidinyl, 3-(methyl)isocarbostyrilyl, 5-(methyl)isocarbostyrilyl, 3-(methyl)-7-(propynyl)isocarbostyrilyl, 7-(aza)indolyl, 6-(methyl)-7-(aza)indolyl, imidizopyridinyl, 9-(methyl)-imidizopyridinyl, pyrrolopyrizinyl, isocarbostyrilyl, 7-(propynyl)isocarbostyrilyl, propynyl-7-(aza)indolyl, 2,4,5-(trimethyl)phenyl, 4-(methyl)indolyl, 4,6-(dimethyl)indolyl, phenyl, napthalenyl, anthracenyl, phenanthracenyl, pyrenyl, stilbenyl, tetracenyl, pentacenyl, difluorotolyl, 4-(fluoro)-6-(methyl)benzimidazole, 4-(methyl)benzimidazole, 6-(azo) thymine, 2-pyridinone, 5 nitroindole, 3 nitropyrrole, 6-(aza) pyrimidine, 2 (amino)purine, 2,6-(diamino)purine, 5 substituted pyrimidines, N2-substituted purines, N6-substituted purines, 06-substituted purines, substituted 1,2,4-triazoles, pyrrolo-pyrimidin-2-on-3-yl, 6-phenyl-pyrrolo-pyrimidin-2-on-3-yl, para-substituted-6-phenyl-pyrrolo-pyrimidin-2-on-3-yl, ortho-substituted-6-phenyl-pyrrolo-pyrimidin-2-on-3-yl, bis-ortho-substituted-6-phenylpyrrolo-pyrimidin-2-on-3-yl, para-(aminoalkylhydroxy)-6-phenyl-pyrrolo-pyrimidin-2-on-3-yl, ortho-(aminoalkylhydroxy)-6- phenyl-pyrrolo-pyrimidin-2-on-3-yl, bis-ortho-(aminoalkyl-hydroxy)-6-phenyl-pyrrolo-pyrimidin-2-on-3-yl, pyridopyrimidin-3-yl, 2-oxo-7-amino-pyridopyrimidin-3-yl, 2-oxo-pyridopyrimidine-3-yl, or any O-alkylated or N alkylated derivatives thereof.

In some embodiments, a modified nucleotide utilized in IVT systems and/or methods described herein may disrupt binding of an RNA to one or more mammalian (e.g., human) endogenous RNA sensors (e.g., innate immune RNA sensors), including, e.g., but not limited to toll-like receptor (TLR)3, TLR7, TLR8, retinoic acid-inducible gene I (RIG-I), melanoma differentiation-associated gene 5 (MDA5), protein kinase R (PKR), 2'-5' oligoadenylate synthetase (OAS), and laboratory of genetics and physiology 2 (LGP2), and combinations thereof. In some embodiments, such modified ribonucleotides may include modifications as described in U.S. Pat. No. 9,334,328, the contents of which are incorporated herein by reference in their entireties for the purposes described herein. Modified nucleosides are typically desirable to be translatable in a host cell (e.g., presence of a modified nucleoside does not prevent translation of an RNA sequence into a respective polypeptide sequence). Effects of modified nucleotides on translation can be assayed, by one of ordinary skill in the art using, for example, a rabbit reticulocyte lysate translation assay.

In some embodiments, a modified ribonucleotide may include a modified internucleoside linkage. Various such modified internucleoside linkages are known in the art; one of skill in the art will appreciate that non-limiting examples of modified internucleoside linkages that may be used in technologies provided herein include phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included. Modified internucleoside linkages that do not include a phosphorus atom therein may have internucleoside linkages that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

In some embodiments, a modified ribonucleotide may include one or more substituted sugar moieties. Various such modified sugar moieties are known in the art; one of skill in the art will appreciate that, in some embodiments, a sugar moiety of a ribonucleotide may include one of the following at the 2' position: H (deoxyribose); OH (ribose); F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted. In some embodiments, a sugar moiety of a ribonucleotide may include a 2' methoxy-ethoxy (2'-O—CH2CH2OCH3, also known as 2'-O-(2-methoxyethyl) or 2'-MOE), 2'-dimethylaminooxyethoxy, i.e., a O(CH2)2ON(CH3)2 group, also known as 2'-DMAOE, and 2'-dimethylaminoethoxyethoxy (also known in the art as 2'O-dimethylaminoethoxyethyl or 2'-DMAEOE), i.e., 2'-O—CH2-OCH2-N(CH2)2; 2'-methoxy (2'-OCH3), 2'-aminopropoxy (2'-OCH2CH2CH2NH2) and 2'-fluoro (2'-F). Similar modifications can also be made at other positions, for example, at the 3' position of the sugar on the 3' terminal nucleotide or in 2'-5' linked nucleotides and the 5' position of 5' terminal nucleotide.

In some embodiments, a mixture of ribonucleotides that are useful for an in vitro transcription reaction may comprise ATP, CTP, GTP, and N1-methylpseudouridine-5' triphosphate (m1ΨTP).

Those skilled in the art are aware that many standard in vitro transcription reactions utilize a reaction mixture in which the ribonucleotides (i.e., ATP, CTP, GTP, and UTP are utilized in 1:1:1:1 ratios (i.e., in which the molar amount of ATP or ATP analogs (considered together) is equal to that of CTP or CTP analogs (considered together) in the reaction mixture, etc. In some embodiments, a standard or control IVT reaction utilizes a reaction mixture in which each ribonucleotide (e.g., ATP, CTP, GTP, and UTP) is present at a concentration of 9 mM.

In some embodiments, the ratio of ATP, CTP, GTP, UTP (including one or more NTP analog(s)) in a reaction mixture for use in an IVT reaction is optimized to improve yield and/or integrity and/or reduce production of aberrant products (e.g., dsRNA). In some embodiments, a molar ratio a of total CTP and/or one or more functional CTP analog(s) to total GTP and/or one or more functional analog(s) is 0.5, 0.8, 0.9, 1.0, 1.1, 1.2, 1.3, 1.4, 1.5, 1.6, 1.7, 1.8, 1.9, 2.0, or higher. In some embodiments, a is at least 1.20, 1.25, 1.30, 1.35, 1.40, 1.45, 1.50, 1.55, 1.60, 1.65, 1.70, 1.75, 1.80, 1.85, 1.90 or more. In some embodiments, a is at least 1.5. In some embodiments, a, is at least about at least about 1.10-fold, 1.15-fold, 1.20-fold, 1.25-fold, 1.30-fold, 1.35-fold, 1.40-fold, 1.45-fold, 1.50-fold, 1.55-fold, 1.60-fold, 1.65-fold, 1.70-fold, or 1.75-fold greater than x, wherein x is a molar ratio of total cytidine and/or one or more functional cytidine analog(s) to total guanosine and/or one or more functional guanosine analog(s). In some embodiments, a is at least about 1.15-fold greater than x. In some embodiments, a is at least about 1.20-fold greater than x.

In some embodiments, a molar ratio b of total CTP and/or one or more functional analog(s) to total UTP and/or one or more functional UTP analog(s) is 0.5, 0.8, 0.9, 1.0, 1.1, 1.2, 1.3, 1.4, 1.5, 1.6, 1.7, 1.8, 1.9, 2.0, or higher. In some embodiments, b is at least 1.30, 1.35, 1.40, 1.45, 1.50, 1.55, 1.60, 1.65, 1.70, 1.75, 1.80, 1.85, 1.90 or more. In some embodiments, b is at least 1.5. In some embodiments, b is at least about 1.10-fold, 1.15-fold, 1.20-fold, 1.25-fold, 1.30-fold, 1.35-fold, 1.40-fold, 1.45-fold, 1.50-fold, 1.55-fold, 1.60-fold, 1.65-fold, 1.70-fold, or 1.75-fold greater than y, wherein y is a molar ratio of total cytidine and/or one or more functional cytidine analog(s) to total uridine and/or one or more functional uridine analog(s). In some embodiments, b is at least about 1.15-fold greater than y. In some embodiments, b is at least about 1.20-fold greater than y.

In some embodiments, a molar ratio c of total CTP and/or one or more functional analog(s) to total adenosine triphosphate (ATP) and/or one or more functional ATP analog(s) is 0.5, 0.8, 0.9, 1.0, 1.1, 1.2, 1.3, 1.4, 1.5, 1.6, 1.7, 1.8, 1.9, 2.0, or higher. In some embodiments, c is at least 1.10, 1.15, 1.20, 1.25, 1.30, 1.35, 1.40, 1.45, or 1.50. In some embodiments, c is at least 1.25. In some embodiments, c is at least about 1.10-fold, 1.15-fold, 1.20-fold, 1.25-fold, 1.30-fold, 1.35-fold, 1.40-fold, 1.45-fold, 1.50-fold, 1.55-fold, 1.60-fold, 1.65-fold, 1.70-fold, or 1.75-fold greater than z, wherein z is a molar ratio of total cytidine and/or one or more functional cytidine analog(s) to total adenosine and/or one or more functional adenosine analog(s). In some embodiments, c is at least about 1.15-fold greater than z. In some embodiments, c is at least about 1.20-fold greater than z.

In some embodiments, a is at least 1.25 and/or a is at least about 1.10-fold greater than x. In some embodiments, b is at least 1.25 and/or b is at least about 1.10-fold greater than y. In some embodiments, c is at least 1.10 and/or c is at least about 1.10-fold greater than z.

In some embodiments, starting CTP and/or one or more functional CTP analog(s) volume (ml/L starting IVT volume) is at least about 85, 90, 95, 100, 105, 110, 115, 120, 125, 130, 135, 140, 145, 150 ml/L or higher. In some embodiments, starting CTP and/or one or more functional CTP analog(s) volume is about 80-150, 85-145, or 90-140 ml/L.

In some embodiments, starting ATP and/or one or more functional ATP analog(s) volume (ml/L starting IVT volume) is at least about 85, 90, 95, 100, 105, 110, 115, 120, 125, 130, 135, 140, 145, 150 ml/L or higher. In some embodiments, starting ATP and/or one or more functional ATP analog(s) volume is about 80-150, 85-145, 85-140, or 85-135 ml/L.

In some embodiments, starting GTP and/or one or more functional GTP analog(s) volume (ml/L starting IVT volume) is at least about 1, 2, 3, 4, 5, 6, 7, 8, 9, 10 ml/L or higher. In some embodiments, starting GTP and/or one or more functional GTP analog(s) volume is about 1-10, 2-9, 3-8, 4-7, 4-6, or 4-5 ml/L.

In some embodiments, starting UTP and/or one or more functional UTP analog(s) volume (ml/L starting IVT volume) is at least about 1, 2, 3, 4, 5, 6, 7, 8, 9, 10 ml/L or higher. In some embodiments, starting UTP and/or one or more functional UTP analog(s) volume is about 1-10, 2-9, 3-8, 4-7, 4-6, or 4-5 ml/L.

In some embodiments, the ratio of ATP, CTP, GTP, and m1'TP in a reaction mixture for use in an in vitro transcription in accordance with the present disclosure is independent of that present in the transcript being generated.

5' Cap

In some embodiments, an RNA produced by technologies described herein may comprise a cap at its 5' end. Those skilled in the art will appreciate that addition of a 5' cap to an RNA (e.g., mRNA) can facilitate recognition and attachment of the RNA to a ribosome to initiate translation and enhances translation efficiency. Those skilled in the art will also appreciate that a 5' cap can also protect an RNA product from 5' exonuclease mediated degradation and thus increases half-life. Methods for capping are known in the art; one of ordinary skill in the art will appreciate that in some embodiments, capping may be performed after in vitro transcription in the presence of a capping system (e.g., an enzyme based capping system such as, e.g., capping enzymes of vaccinia virus). In some embodiments, a capped RNA may be obtained by in vitro capping of RNA that has a 5' triphosphate group or RNA that has a 5' diphosphate group with a capping enzyme system (including, e.g., but not limited to vaccinia capping enzyme system or *Saccharomyces cerevisiae* capping enzyme system). In some embodiments, a capping agent may be introduced into an in vitro transcription reaction mixture (e.g., ones as described herein), along with a plurality of ribonucleotides such that a cap is incorporated into an RNA during transcription (also known as co-transcriptional capping). While it may be desirable to include, in some embodiments, a 5' cap in an RNA, an RNA, in some embodiments, may not have a 5' cap.

In some embodiments, a 5' capping agent can be added to an in vitro transcription reaction mixture. In some embodiments, a 5' capping agent may comprise a modified nucleotide, for example, a modified guanine nucleotide. In some embodiments, a 5' capping agent may comprise, for example, a methyl group or groups, glyceryl, inverted deoxy abasic moiety, 4'5' methylene nucleotide, 1-(beta-D-erythrofuranosyl) nucleotide, 4' thio nucleotide, carbocyclic nucleotide, 1,5-anhydrohexitol nucleotide, L-nucleotides, alphanucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3'phosphorothioate, phosphorodithioate, or bridging or non-bridging methylphosphonate moiety, inosine, N1-methyl-guanosine, 2'-fluoro-guanosine, 7'deaza-guanosine, 8-oxo-guanosine, 2-aminoguanosine, LNA-guanosine, 2-azido-guanosine. In some embodiments, a 5' capping agent may be or comprise a dinucleotide cap analog (including, e.g., a m7GpppG cap analog or an N7-methyl, 2'-O-methyl-GpppG anti-reverse cap analog (ARCA) cap analog or an N7-methyl, 3'-O-methyl-GpppG ARCA cap analog). In some embodiments, a 5' capping agent comprises a 5' N7-Methyl-3'-O-Methylguanosine structure, e.g., Clean-Cap® Reagents (Trilink BioTechnologies). In some embodiments, a 5'-capping agent is added in excess to a particular ribonucleotide or ribonucleotides (e.g., GTP, ATP, UTP, CTP, or modified version thereof) to enable incorporation of the 5'-cap as the first addition to the RNA transcript.

Polymerases

Various RNA polymerases that are suitable for transcription reactions are known in the art, including, but not limited to, RNA polymerases. In some embodiments, a RNA polymerase is a T7 RNA polymerase, T3 RNA polymerase, SP6 RNA polymerase, N4 virion RNA polymerase, or a variant or functional domain thereof). Naturally catalysed RNA-dependent RNA polymerases are typically encoded by all RNA viruses except retroviruses. Typical representatives of viruses encoding a RNA-dependent RNA polymerase are alphaviruses. A skilled person will understand that an RNA polymerase utilized herein may be a recombinant RNA polymerase, and/or a purified RNA polymerase, i.e., not as part of a cell extract, which contains other components in addition to the RNA polymerases. In some embodiments, an RNA polymerase that is useful for commercial-scale transcription is a T7 RNA polymerase. In some embodiments, an inorganic pyrophosphatase may be added to improve the yield of transcription reaction (e.g., in some embodiments catalysed by T7 RNA polymerase).

Exemplary In Vitro Transcription Reactions

One of ordinary skill in the art will be aware of components typically included in an IVT reaction mixture. For example, an IVT reaction mixture typically includes a nucleic acid template (e.g., DNA template, e.g., as described herein), ribonucleotides (e.g., as described herein), an RNA polymerase (e.g., a DNA dependent RNA polymerases).

In some embodiments, a reaction mixture comprises the nucleic acid template at a concentration of 0.05-2 µg/µL (including, e.g., 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 µg/µL). In some embodiments, a reaction mixture comprises an RNA polymerase volume (ml/L starting IVT volume) of about 70, 71, 72, 73, 74, 75, 76, 77, 78, 79, 80, 81, 82, 83, 84, 85, 86, 87, 88, 89, 90 ml/L. In some embodiments, a reaction mixture comprises an RNA polymerase volume of about 70-90, 72-88, 72-90, or 70-88 ml/L.

In some embodiments, an IVT reaction mixture further comprises one or more of a reaction buffer, an RNase inhibitor, a pyrophosphatase, one or more salts, a reducing agent, and/or spermidine.

In some embodiments, an IVT reaction mixture further comprises a reaction buffer. In some embodiments, a reaction buffer comprises HEPES, Tris-HCl, or PBS. In some embodiments, the reaction mixture comprises the reaction buffer at a concentration of 20-60 mM. In some embodiments, the reaction buffer has a pH of 7-9 (including, e.g., 7.0 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, and 9.0).

In some embodiments, an IVT reaction mixture may further comprise an RNAse inhibitor. In some such embodiments, the RNAse inhibitor is at a concentration of 0.01-0.1 U/µL (including, e.g., 0.01, 0.02, 0.03, 0.04, 0.05, 0.06, 0.07, 0.08, 0.09, or 0.10 U/µL). In some embodiments, one unit (U) of an RNAse inhibitor inhibits activity of 5 ng of RNAse (e.g., RNAse A) by at least 50% (including, e.g., at least 60%, at least 70%, at least 80%, at least 90%, at least 99% or more).

In some embodiments, an IVT reaction mixture may further comprise a pyrophosphatase (e.g., an inorganic pyrophosphatase). In some embodiments, an IVT reaction mixture comprises pyrophosphatase (e.g., an inorganic pyrophosphatase) at a concentration of 0.01-0.2 mU/µL. In some embodiments, an IVT reaction mixture comprises pyrophosphatase (e.g., an inorganic pyrophosphatase) at a concentration of 0.01, 0.05, 0.1, 0.15, or 0.20 mU/µL. In some embodiments, an IVT reaction mixture comprises a pyrophosphatase volume (ml/L starting IVT volume) of about 0.80, 0.85, 0.90, 0.95, 1.0, 1.05, 1.10 ml/L. In some embodiments, an IVT reaction mixture comprises a pyrophosphatase volume of 0.80-1.10, 0.80-1.05, 0.85-1.10, 0.85-1.05, 0.90-1.10, 0.90-1.05, 0.95-1.10, or 0.95-1.05 ml/L.

In some embodiments, an IVT reaction mixture may further comprise one or more salts (e.g., monovalent salts and/or divalent salts). In some embodiments, the reaction mixture comprises the one or more salts at a concentration of 20-60 mM. In some embodiments, one or more salts comprises one or more magnesium salts and/or one or more calcium salts. In some embodiments, the one or more magnesium salts comprises magnesium acetate or magnesium chloride.

In some embodiments, an IVT reaction mixture may further comprise a reducing agent (e.g., dithiothreitol, 2-mercaptoethanol, etc.). In some such embodiments, the reaction mixture comprises the reducing agent at a concentration of 5-15 mM.

In some embodiments, an IVT reaction mixture may further comprise sperimidine. In some such embodiments, the reaction mixture comprises the sperimidine at a concentration of 0.5-3 mM.

In some embodiments, certain reaction mixture components are added in a specific order. In some embodiments, a portion of the total CTP and/or more or functional CTP analog(s) is added to the reaction mixture before transcription begins and/or at a start of transcription and a remaining portion of the total CTP and/or one or more functional CTP analog(s) is added to the reaction mixture after the start of transcription. In some embodiments, all of the total CTP and/or one or more functional CTP analog(s) is added to the reaction mixture before transcription begins and/or at a start of transcription. In some embodiments, a portion of the total GTP and/or one or more functional GTP analog(s) is added to the reaction mixture before transcription begins and/or at a start of transcription and a remaining portion of the total GTP and/or one or more functional GTP analog(s) is added to the reaction mixture after the start of transcription. In some embodiments, all of the total GTP and/or one or more functional GTP analog(s) is added to the reaction mixture before transcription begins and/or at a start of transcription. In some embodiments, a portion of the total UTP and/or one or more functional UTP analog(s) is added to the reaction mixture before transcription begins and/or at a start of transcription and a remaining portion of the total UTP and/or one or more functional UTP analog(s) is added to the reaction mixture after the start of transcription. In some embodiments, all of the total UTP and/or one or more functional UTP analog(s) is added to the reaction mixture before transcription begins and/or at a start of transcription. In some embodiments, a portion of the total ATP and/or one or more functional ATP analog(s) is added to the reaction mixture before transcription begins and/or at a start of transcription and a remaining portion of the total ATP and/or one or more functional ATP analog(s) is added to the reaction mixture after the start of transcription. In some embodiments, all of the total ATP and/or one or more functional ATP analog(s) is added to the reaction mixture before transcription begins and/or at a start of transcription. In some embodiments, a portion of the total of a plurality of nucleotides (e.g., ATP, CTP, GTP, and/or UTP and/or one or more functional analog(s) thereof) is added to the reaction mixture before transcription begins and/or at a start of transcription and a remaining portion is added to the reaction mixture after the start of transcription. In some embodiments, all of the total of a plurality of nucleotides (e.g., ATP, CTP, GTP, and/or UTP and/or one or more functional analog(s) thereof) is added to the reaction mixture before transcription begins and/or at a start of transcription.

In some embodiments, GTP and/or UTP and/or one or more functional analog(s) thereof are limited (e.g., maintained at a sufficiently low concentration) during an IVT reaction. In some such embodiments, GTP and/or UTP and/or one or more functional analog(s) thereof are kept at a sufficiently low concentration by using, for example, a fed-batch approach. Without wishing to be bound by any one theory, cap analogs can directly compete with GTP for incorporation as initial nucleotide (start nucleotide), and is incorporated as readily as any other nucleotide (WO2006/004648). To favor the incorporation of the cap analog, a molar excess of the cap analog over GTP is typically used (e.g. at a 4:1 ratio) and the GTP concentration is reduced compared to the other ribonucleoside triphosphates (e.g., ATP, CTP and/or UTP or analogs thereof). Under these conditions GTP usually becomes the limiting factor for the synthesis of RNA molecules. Consequently, a high proportion of the other NTPs (usually between 40 to 70%) are not used for RNA synthesis but wasted. With this approach, the RNA yield is typically limited to about 1 mg/ml (WO2006/004648).

To compensate for the limited yield resulting from the low GTP concentrations, yields of capped RNA have been increased by supplementing the reaction with the competing nucleotide (GTP, or ATP in case A-cap is used) in such a way that a ratio between 1:1 and 1:50 GTP to cap analog is maintained. With this approach, it has been reported that amount of capped RNA produced per reaction could be doubled (WO2006/004648).

Without wishing to be bound by any one theory, RNA molecules synthesized by T7 RNA polymerase during run-off transcription of linearized DNA templates can be longer than the coded PNA (Triana-Alonso et al., 1995, JBC; 270(11): 6298-6307). After leaving the DNA template, the RNA polymerase can bind a transcript to the template site and the 3-end of the transcript to the product site and extend it, if the 3-end is not part of a stable secondary structure (self-complementary 3' extension). This effect seems to be especially sensitive to the UTP concentration and a reduction exclusively of the UTP concentration leads to faithful transcription. However, lowering the UTP concentration can also affect the RNA yield. Especially if RNA contains a poly(A) tail, as is common in RNAs such as mRNAs, an excess of unincorporated UTP in the transcription reaction can result in RNA-template dependent incorporation of uridine nucleotides opposite of the poly-A-sequence, resulting in double-stranded RNA molecules which can activate the innate immune response and decrease polypeptide synthesis (Kariko et al., 2011, Nucleic Acids Res.; 39(21): e142).

In vitro transcription reactions are, in some embodiments, performed as batch reactions in which all components are combined and then incubated to allow the synthesis of RNA molecules until the reaction terminates. Fed-batch reactions were developed to increase the efficiency of the in vitro transcription reaction (Kern et al., 1997. Biotechnol. Prog. 13, 747-756; Kern et al., 1999. Biotechnol. Prog. 15, 174-184). In some embodiments, in a fed-batch system all components are combined, but then additional amounts of some of the reagents are added over time (e.g. NTPs and magnesium) to maintain constant reaction conditions.

In some embodiments, total GTP and/or one or more functional analog(s) thereof is added to an IVT reaction mixture (e.g., by fed-batch) throughout the duration of an IVT reaction. In some such embodiments, total GTP and/or one or more functional analog(s) thereof bolus volume (ml/L starting IVT volume) is added at about 150, 155, 160, 165, 170, 175, 180, 185, or 190 ml/L. In some such embodiments, total GTP and/or one or more functional analog(s) thereof bolus volume (ml/L starting IVT volume) is added at about 150, 155, 160, 165, 170, 175, 180, 185, or 190 ml/L. In some such embodiments, total GTP and/or one or more functional analog(s) thereof bolus volume is added at a range of about 140-200, 145-195, or 150-190 ml/L.

In some embodiments, total UTP and/or one or more functional analog(s) thereof is added to an IVT reaction mixture (e.g., by fed-batch) throughout the duration of an IVT reaction. In some such embodiments, total UTP and/or one or more functional analog(s) thereof bolus volume (ml/L starting IVT volume) is added at about 150, 155, 160, 165, 170, 175, 180, 185, or 190 ml/L. In some such embodiments, total UTP and/or one or more functional analog(s) thereof bolus volume (ml/L starting IVT volume) is added at about 150, 155, 160, 165, 170, 175, 180, 185, or 190 ml/L. In some such embodiments, total UTP and/or one or more functional analog(s) thereof bolus volume is added at a range of about 140-200, 145-195, or 150-190 ml/L. In some embodiments, GTP and/or UTP are limited and either or both of CTP and/or ATP are elevated (e.g., as discussed elsewhere herein) in an initial IVT reaction mixture and/or at one or more time points during the IVT reaction.

Exemplary In Vitro Transcription Reaction Conditions

In some embodiments, an IVT reaction is conducted, e.g., in a bioreactor described herein (selected for a certain IVT reaction volume, e.g., as described herein) for a period of time. In some embodiments, the period of time is at least 20 minutes, including, e.g., at least 25 minutes, at least 30 minutes, at least 40 minutes, at least 55 minutes, at least 60 minutes, at least 75 minutes, at least 90 minutes, at least 105 minutes, at least 120 minutes, at least 135 minutes, at least 150 minutes, at least 165 minutes, or at least 180 minutes. In some embodiments, the period of time is 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, or 180 minutes. In some embodiments, the period of time is about 1.5-3 hours. In some embodiments, the period of time is about 25-30 minutes.

In some embodiments, an IVT reaction is conducted, e.g., in a bioreactor described herein for a period of time (e.g., as described herein) at a temperature at which a selected RNA polymerase is functionally active. While typical phage RNA polymerases (e.g., T7 polymerases that carry out IVT reactions are usually not activate at elevated temperatures (e.g., above 45° C.), thermostable RNA polymerase (e.g., thermostable variants of T7 RNA polymerases such as ones described in U.S. Ser. No. 10/519,431, the contents of which are incorporated by reference for purposes described herein) can show increased stability at elevated temperatures. In some embodiments, IVT reaction is performed at a temperature of about 25° C. or higher, including, e.g., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., or 45° C. In some embodiments, in vitro transcription is performed at a temperature of about 45° C. or higher, including, e.g., 46° C., 47° C., 48° C., 49° C., 50° C., 51° C., 52° C., 53° C., 54° C., 55° C. or higher.

In some embodiments, an IVT reaction is conducted, e.g., in a bioreactor described herein at a pH of about 6, 6.1, 6.2, 6.3, 6.4, 6.5, 6.6, 6.7, 6.8, 6.9, 7.0 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9. In some embodiments, a suitable pH for an in vitro transcription may be about 7.0-9.0.

In some embodiments, in vitro transcription reactions performed in accordance with the present disclosure (e.g., in a bioreactor as described herein) may be performed as continuous feed reactions; in some embodiments, they may be performed as batch-fed reactions. In some embodiments, one or more nucleotides may be added to an in vitro transcription reaction in a step-wise manner (e.g. at least 5, 6, 7, 8, 9, 10, 11, 12, 13, 14, 15, or more bolus feeds). In some embodiments, an agitation rate is selected such that a particular blend time to enable rapid mixing of bolus additions to ensure optimal availability of modified nucleotide solution and one or more other nucleotide solutions during RNA synthesis is achieved.

Bioreactor

In some embodiments, an IVT reaction is conducted in, (i.e., using) a bioreactor described herein.

The term "bioreactor" or "transcription reactor" as used herein refers to a vessel such as a chamber or test tube or column, wherein a transcription reaction is carried out under specific conditions such as described herein. Bioreactors for transcription are known in the art (see WO 1995/08626 and EP 3 155 129). A bioreactor typically is configured such that reaction components are delivered by a feed line to the reactor core and RNA products are removed by passing through an ultrafiltration membrane (see EP 3 155 129 and van de Merbel, (1999), J. Chromatogr. A 856(1-2): 55-82) to the exit stream. A bioreactor useful in methods of the present invention may comprise a reaction module for carrying out transcription reactions, a capture module for temporarily capturing the transcribed RNA molecules, and a control module for controlling the infeed of components of the reaction mixture into the reaction module, wherein the reaction module may comprise a filtration membrane for separating nucleotides from the reaction mixture, and the control of the infeed of components of the reaction mixture by the control module may be based on a measured concentration of separated nucleotides. The bioreactor may be thermally regulated to maintain accurately a specific temperature such as the temperature of the transcription reaction as described herein, e.g., usually between 4° C. and 40° C. The bioreactor may comprise an inflow feet and an exit port. The bioreactor may allow for stirring the reaction mixture during the transcription reaction, e.g., at variable rates of stirring. Stirring may be continuous or discontinuous such as in intervals.

A bioreactor for use according to the invention may be of a size, for example, of 0.2 liter or more, such as 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10, 15, 20, 25, 30, 35, 40, 45, 50 liters or more, or any volume in between. The internal conditions of the bioreactor, including, but not limited to pH and temperature, are typically controlled during a transcription reaction as described herein. A bioreactor can be composed of any material that is suitable for in vitro transcription under the conditions as described herein, including glass, plastic or metal.

In some embodiments, a bioreactor may be equipped with a pump for supplementing the reaction mixture. In some embodiments, a programmable pump may be used for supplementation. In some embodiments, a programmable syringe pump may be used, for example, to automatically perform step-wise addition of one or more reaction mixture components. Alternatively or additionally, in some embodiments, a monitor (e.g., a sensor) may be utilized to detect level(s) of one or more components; in some such embodiments, a monitor may communicate automatically with a pump, for example so that additional feeds may be released upon detection of a reduced amount of such component(s).

Methods of Controlling Nucleotide Level

In some embodiments, in vitro transcription reactions performed in accordance with the present disclosure (e.g., in a bioreactor as described herein) may be performed as continuous feed reactions; in some embodiments, they may be performed as batch-fed reactions. In some embodiments, one or more nucleotides may be added to an in vitro transcription reaction in a step-wise manner (e.g. at least 5, 6, 7, 8, 9, 10, 11, 12, 13, 14, 15, or more bolus feeds). In some embodiments, an agitation rate is selected such that a particular blend time to enable rapid mixing of bolus additions to ensure optimal availability of modified nucleotide solution and one or more other nucleotide solutions during RNA synthesis is achieved.

Exemplary Processing

In some embodiments, RNA produced by IVT as described herein undergoes one or more processing steps (e.g., purification).

Purification of the nucleic acids described herein may include, but is not limited to, nucleic acid clean-up, quality assurance and quality control. Clean-up may be performed by methods known in the arts such as, but not limited to, residual protein digestion and/or DNA digestion by, for example Proteinase K and DNaseI, AGENCOURT® beads (Beckman Coulter Genomics, Danvers, MA), poly-T beads, LNA™ oligo-T capture probes (EXIQON® Inc, Vedbaek, Denmark) or HPLC based purification methods such as, but not limited to, strong anion exchange HPLC, weak anion exchange HPLC, reverse phase HPLC (RP-HPLC), and hydrophobic interaction HPLC (HIC-HPLC). The term "purified" when used in relation to a nucleic acid such as a "purified nucleic acid" refers to one that is separated from at least one contaminant. A "contaminant" is any substance that makes another unfit, impure or inferior. Thus, a purified nucleic acid (e.g., DNA and RNA) is present in a form or setting different from that in which it is found in nature, or a form or setting different from that which existed prior to subjecting it to a treatment or purification method.

Characterization

In some embodiments, RNA can be assessed by one or more quality control parameters. In some embodiments, quality control parameters may be assessed and/or monitored at any time during production process of RNAs and/or compositions comprising the same. For example, in some embodiments, RNA quality control parameters, including one or more of RNA integrity, RNA concentration, residual dsRNA, and/or capping may be assessed and/or monitored during and/or after each or certain steps of an RNA manufacturing progress, e.g., after IVT and/or each purification step.

In some embodiments, one or more quality control parameters may be utilized during manufacture or other preparation or use of RNAs (e.g., as a release test).

In some embodiments, one or more quality control parameters may be assessed to determine whether RNAs described herein meet or exceed acceptance criteria (e.g., for subsequent formulation and/or release for distribution). In some embodiments, such quality control parameters may include, but are not limited to RNA integrity, RNA concentration, residual dsRNA, and/or capping.

Certain methods for assessing RNA quality are known in the art; for example, one of skill in the art will recognize that in some embodiments, one or more analytical tests can be used for RNA quality assessment. Examples of such certain analytical tests may include, but are not limited to, gel electrophoresis (e.g., agarose gel electrophoresis, capillary gel electrophoresis), UV absorption, and/or PCR assay.

RNA Integrity

In some embodiments, RNA integrity is assessed and/or monitored (e.g., determined at one or more points over time). In some embodiments, RNA integrity can be assessed and/or monitored by agarose gel electrophoresis. In some embodiments, RNA integrity can be assessed and/or monitored by capillary gel electrophoresis. In some embodiments, RNA integrity can be quantitatively determined using capillary electrophoresis. In some embodiments, RNA solution must give rise to a single peak at the expected retention time consistent with the expected lengths as compared to the retention times of a standard ladder. In some embodiments, quantification of the main RNA peak is calculated in relation to signal intensities in the electropherogram where degradation products are detectable.

In some embodiments, RNA integrity of RNA molecule(s) produced in accordance with technologies provided herein is at least about 40%, 45%, 50%, 55%, 60%, 65%, 70%, 75%, 80%, 85%, 90%, 95%, or higher relative to an appropriate comparator (e.g., an otherwise comparable in vitro transcription reaction). In some embodiments, RNA integrity of RNA molecule(s) produced in accordance with technologies provided herein is increased at least about 1%, 2%, 3%, 4%, 5%, 6%, 7%, 8%, 9%, 10%, 11%, 12%, 13%, 14%, 15%, 16%, 17%, 18%, 19%, or 20% relative to an appropriate comparator (e.g., an otherwise comparable in vitro transcription reaction, for example utilizing a reaction mixture in which a is not at least 1.25, b is not at least 1.25, and/or c is not at least 1.10). In some embodiments, RNA integrity of RNA molecule(s) produced in accordance with the present disclosure is increased at least about 1%, 2%, 3%, 4%, 5%, 6%, 7%, 8%, 9%, 10%, 11%, 12%, 13%, 14%, 15%, 16%, 17%, 18%, 19%, or 20% relative to an appropriate comparator (e.g., an otherwise comparable in vitro transcription reaction, for example utilizing a reaction mixture in which: d is not at least 1.10 and/or e is not at least 1.10; a is not at least 1.25, b is not at least 1.25, c is not at least 1.10, and/or d is not at least 1.10 and/or e is not at least 1.10; a is not at least 1.25, b is not at least 1.25, c is not at least 1.10, and/or d is at least 1.10 and/or e is at least 1.10; and/or a is at least 1.25, b is at least 1.25, and/or c is at least 1.10, and/or d is not at least 1.10 and/or e is not at least 1.10). In some embodiments, RNA integrity of RNA molecule(s) produced in accordance with technologies provided herein is increased at least about 1%, 2%, 3%, 4%, 5%, 6%, 7%, 8%, 9%, 10%, 11%, 12%, 13%, 14%, 15%, 16%, 17%, 18%, 19%, or 20% relative to an appropriate comparator (e.g., RNA produced by an IVT reaction not disclosed in the herein). In some embodiments, RNA integrity of RNA molecule(s) produced in accordance with technologies provided herein is increased at least about 1%, 2%, 3%, 4%, 5%, 6%, 7%, 8%, 9%, 10%, 11%, 12%, 13%, 14%, 15%, 16%, 17%, 18%, 19%, or 20% relative to an appropriate comparator (e.g., an otherwise comparable in vitro transcription reaction, for example utilizing a reaction mixture in which a is not at least about 1.10-fold greater than x, b is not at least about 1.10-fold greater than y, and/or c is not at least about 1.10-fold greater than z). In some embodiments, RNA integrity of RNA molecule(s) produced in accordance with the present disclosure is increased at least about 1%, 2%, 3%, 4%, 5%, 6%, 7%, 8%, 9%, 10%, 11%, 12%, 13%, 14%, 15%, 16%, 17%, 18%, 19%, or 20% relative to an appropriate comparator (e.g., an otherwise comparable in vitro transcription reaction, for example utilizing a reaction mixture in which: d is not at least about 1.05-fold greater than v and/or e is not at least about 1.05-fold greater than w; a is not at least about 1.10-fold greater than x, b is not at least about 1.10-fold greater than y, c is not at least about 1.10-fold greater than z, and/or d is not at least about 1.05-fold greater than v and/or e is not at least about 1.05-fold greater than w; a is not at least about 1.10-fold greater than x, b is not at least about 1.10-fold greater than y, c is not at least about 1.10-fold greater than z, and/or d is at least about 1.05-fold greater than v and/or e is at least about 1.05-fold greater than w; and/or a is at least about 1.10-fold greater than x, b is at least about 1.10-fold greater than y, and/or c is at least about 1.10-fold greater than z, and/or d is not at least about 1.05-fold greater than v and/or e is not at least about 1.05-fold greater than w).

In some embodiments, RNA integrity is increased at least about 5% relative to an appropriate comparator. In some embodiments, RNA integrity is increased at least about 8% relative to an appropriate comparator.

RNA Concentration

In some embodiments, RNA concentration (e.g., RNA molecules produced in accordance with technologies provided herein) is assessed and/or monitored (e.g., determined at one or more points over time, for example in or after an IVT reaction). In some embodiments, RNA concentration is determined using UV absorption spectrophotometry. In some embodiments, RNA concentration is determined according to the method described within Ph. Eur. 2.2.25. In some embodiments, desirable particular RNA concentration is achieved at a particular batch scale. In some particular embodiments, a high RNA concentration is achieved in a large-scale manufacturing process.

In some embodiments, an achieved RNA concentration (e.g., of an RNA produced by an IVT reaction as described herein) may be at least 1 mg/mL (including, e.g., at least 1.5 mg/mL, at least 2 mg/mL, at least 2.5 mg/mL, at least 3 mg/mL, at least 3.5 mg/mL, at least 4 mg/mL, at least 4.5 mg/mL, at least 5 mg/mL, at least 6 mg/mL, or higher). In some embodiments, an RNA concentration may be 1.5 mg/mL to 5 mg/mL or 2 mg/mL to 4 mg/mL or 2.0-2.5 mg/mL.

In some embodiments, the concentration of RNA molecules produced in accordance with technologies provided herein (e.g., in an IVT reaction as described herein) is at least about 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 11 mg/mL, 12 mg/mL, 13 mg/mL, 14, mg/mL, or 15 mg/mL. In some embodiments, the concentration of RNA molecule(s) produced in accordance with technologies provided herein is at least about 10%, 11%, 12%, 13%, 14%, 15%, 16%, 17%, 18%, 19%, 20%, 21%, 22%, 23%, 24%, 25%, 26%, 27%, 28%, 29%, or 30% relative to an appropriate comparator (e.g., an otherwise comparable in vitro transcription reaction, for example utilizing a reaction mixture in which a is not at least 1.25, b is not at least 1.25, and/or c is not at least 1.10). In some embodiments, the concentration of RNA molecules produced in accordance with technologies of the present disclosure is increased at least about 1%, 2%, 3%, 4%, 5%, 6%, 7%, 8%, 9%, 10%, 11%, 12%, 13%, 14%, 15%, 16%, 17%, 18%, 19%, or 20% relative to an appropriate comparator (e.g., an otherwise comparable in vitro transcription reaction, for example utilizing a reaction mixture in which: d is not at least 1.10 and/or e is not at least 1.10; a is not at least 1.25, b is not at least 1.25, c is not at least 1.10, and/or d is not at least 1.10 and/or e is not at least 1.10; a is not at least 1.25, b is not at least 1.25, c is not at least 1.10, and/or d is at least 1.10 and/or e is at least 1.10; and/or a is at least 1.25, b is at least 1.25, and/or c is at least 1.10, and/or d is not at least 1.10 and/or e is not at least 1.10). In some embodiments, the concentration of RNA molecules produced in accordance with technologies provided herein is increased at least about 10%, 11%, 12%, 13%, 14%, 15%, 16%, 17%, 18%, 19%, 20%, 21%, 22%, 23%, 24%, 25%, 26%, 27%, 28%, 29%, or 30% relative to an appropriate comparator (e.g., an otherwise comparable in vitro transcription reaction, for example utilizing a reaction mixture in which a is not at least about 1.10-fold greater than x, b is not at least about 1.10-fold greater than y, and/or c is not at least about 1.10-fold greater than z). In some embodiments, the concentration of RNA molecules produced in accordance with technologies provided herein is increased at least about 1%, 2%, 3%, 4%, 5%, 6%, 7%, 8%, 9%, 10%, 11%, 12%, 13%, 14%, 15%, 16%, 17%, 18%, 19%, or 20% relative to an appropriate comparator (e.g., an otherwise comparable in vitro transcription reaction, for example utilizing a reaction mixture in which: d is not at least about 1.05-fold greater than v and/or e is not at least about 1.05-fold greater than w; a is not at least about 1.10-fold greater than x, b is not at least about 1.10-fold greater than y, c is not at least about 1.10-fold greater than z, and/or d is not at least about 1.05-fold greater than v and/or e is not at least about 1.05-fold greater than w; a is not at least about 1.10-fold greater than x, b is not at least about 1.10-fold greater than y, c is not at least about 1.10-fold greater than z, and/or d is at least about 1.05-fold greater than v and/or e is at least about 1.05-fold greater than w; and/or a is at least about 1.10-fold greater than x, b is at least about 1.10-fold greater than y, and/or c is at least about 1.10-fold greater than z, and/or d is not at least about 1.05-fold greater than v and/or e is not at least about 1.05-fold greater than w). In some embodiments, the concentration of RNA molecules produced in accordance with technologies provided herein is increased at least about 20% (including, e.g., at least about 30%, 40%, 50%, 60%, 70%, 80%, 90%, 99% or more) relative to an appropriate comparator.

Residual Double-Stranded RNA

Among other things, the present disclosure provides insights that provided technologies may provide certain benefits such as, for example, reduced level of dsRNA. In some embodiments, low dsRNA levels are particularly useful in preparations of therapeutic RNAs. Alternatively or additionally, ability to reduce dsRNA may be particularly beneficial in large scale (e.g., commercial scale as described herein) RNA manufacturing.

In some embodiments, residual dsRNA (dsRNA) can be assessed and/or monitored using, for example, polymerase chain reaction (PCR), absorbance, fluorescent dyes, and/or gel electrophoresis. In some embodiments, dsRNA is assessed and/or monitored using quantitative PCR.

In some particular embodiments, for example, dsRNA is assessed and/or monitored by evaluating RNA samples and a dsRNA reference (2000 pg dsRNA/µg RNA, 1500 pg dsRNA/µg RNA, 1000 pg dsRNA/µg RNA, 500 pg dsRNA/µg RNA, or lower) representing the upper limit of accepted residual dsRNA content) are immobilized on a positively charged nylon membrane and incubated with a dsRNA specific monoclonal antibody. After incubation with horseradish peroxidase (HRP)-conjugated secondary, enhanced chemiluminescence (ECL) substrate is added to the membrane and chemiluminescence is detected by a bioimager system. Signal intensities are quantified by densitometry and values of the RNA samples are compared to the signal intensity of the dsRNA reference. Results are reported as complies with the specified upper limit. In some embodiments, the dsRNA-specific monoclonal antibody is mouse IgG clone J2. In some embodiments, HRP-conjugated secondary is an anti-mouse IgG secondary.

In some embodiments, residual dsRNA during and/or after transcription of RNA molecules produced in accordance with technologies provided herein is at least about 25 pg dsRNA/µg RNA, 50 pg dsRNA/µg RNA, 75 pg dsRNA/µg RNA, 100 pg dsRNA/µg RNA, 125 pg dsRNA/µg RNA, 150 pg dsRNA/µg RNA, 175 pg dsRNA/µg RNA, 200 pg dsRNA/µg RNA, 225 pg dsRNA/µg RNA, 250 pg dsRNA/µg RNA, 275 pg dsRNA/µg RNA, or 300 pg dsRNA/µg RNA. In some embodiments, residual dsRNA during and/or after transcription of RNA molecule(s) produced in accordance with technologies provided herein is decreased at least about 60%, 61%, 62%, 63%, 64%, 65%, 66%, 67%, 68%, 69%, 70%, 71%, 72%, 73%, 74%, 75%, 76%, 77%, 78%, 79%, or 80% relative to an appropriate comparator (e.g., an otherwise comparable in vitro transcription reaction, for example utilizing a reaction mixture in which a is not at least 1.25, b is not at least 1.25, and/or c is not at least 1.10). In some embodiments, residual dsRNA during and/or after transcription of RNA molecule(s) produced in accordance with technologies provided herein is increased at least about 1%, 2%, 3%, 4%, 5%, 6%, 7%, 8%, 9%, 10%, 11%, 12%, 13%, 14%, 15%, 16%, 17%, 18%, 19%, or 20% relative to an appropriate comparator (e.g., an otherwise comparable in vitro transcription reaction, for example utilizing a reaction mixture in which: d is not at least 1.10 and/or e is not at least 1.10; a is not at least 1.25, b is not at least 1.25, c is not at least 1.10, and/or d is not at least 1.10 and/or e is not at least 1.10; a is not at least 1.25, b is not at least 1.25, c is not at least 1.10, and/or d is at least 1.10 and/or e is at least 1.10; and/or a is at least 1.25, b is at least 1.25, and/or c is at least 1.10, and/or d is not at least 1.10 and/or e is not at least 1.10). In some embodiments, residual dsRNA during and/or after transcription of RNA molecule(s) produced in accordance with technologies provided herein is decreased at least about 60%, 61%, 62%, 63%, 64%, 65%, 66%, 67%, 68%, 69%, 70%, 71%, 72%, 73%, 74%, 75%, 76%, 77%, 78%, 79%, or 80% relative to an appropriate comparator (e.g., an otherwise comparable in vitro transcription reaction, for example utilizing a reaction mixture in which a is not at least about 1.10-fold greater than x, b is not at least about 1.10-fold greater than y, and/or c is not at least about 1.10-fold greater than z). In some embodiments, residual dsRNA during and/or after transcription of RNA molecules produced in accordance with technologies provided herein is increased at least about 1%, 2%, 3%, 4%, 5%, 6%, 7%, 8%, 9%, 10%, 11%, 12%, 13%, 14%, 15%, 16%, 17%, 18%, 19%, or 20% relative to an appropriate comparator (e.g., an otherwise comparable in vitro transcription reaction, for example utilizing a reaction mixture in which: d is not at least about 1.05-fold greater than v and/or e is not at least about 1.05-fold greater than w; a is not at least about 1.10-fold greater than x, b is not at least about 1.10-fold greater than y, c is not at least about 1.10-fold greater than z, and/or d is not at least about 1.05-fold greater than v and/or e is not at least about 1.05-fold greater than w; a is not at least about 1.10-fold greater than x, b is not at least about 1.10-fold greater than y, c is not at least about 1.10-fold greater than z, and/or d is at least about 1.05-fold greater than v and/or e is at least about 1.05-fold greater than w; and/or a is at least about 1.10-fold greater than x, b is at least about 1.10-fold greater than y, and/or c is at least about 1.10-fold greater than z, and/or d is not at least about 1.05-fold greater than v and/or e is not at least about 1.05-fold greater than w). In some embodiments, residual dsRNA concentration is decreased at least about 70% including, e.g., at least about 60%, 50%, 40%, 30%, 20%, 10% or less). In some embodiments, residual dsRNA during and/or after transcription of RNA molecule(s) produced in accordance with technologies provided herein is increased at least about 1%, 2%, 3%, 4%, 5%, 6%, 7%, 8%, 9%, 10%, 11%, 12%, 13%, 14%, 15%, 16%, 17%, 18%, 19%, or 20% relative to an appropriate comparator (e.g., an otherwise comparable in vitro transcription reaction, for example utilizing a reaction mixture in which: d is not at least 1.10 and/or e is not at least 1.10; a is not at least 1.25, b is not at least 1.25, c is not at least 1.10, and/or d is not at least 1.10 and/or e is not at least 1.10; a is not at least 1.25, b is not at least 1.25, c is not at least 1.10, and/or d is at least 1.10 and/or e is at least 1.10; and/or a is at least 1.25, b is at least 1.25, and/or c is at least 1.10, and/or d is not at least 1.10 and/or e is not at least 1.10). In some embodiments, residual dsRNA during and/or after transcription of RNA molecule(s) produced in accordance with technologies provided herein is increased at least about 1%, 2%, 3%, 4%, 5%, 6%, 7%, 8%, 9%, 10%, 11%, 12%, 13%, 14%, 15%, 16%, 17%, 18%, 19%, or 20% relative to an appropriate comparator (e.g., an otherwise comparable in vitro transcription reaction, for example utilizing a reaction mixture in which: d is not at least about 1.05-fold greater than v and/or e is not at least about 1.05-fold greater than w; a is not at least about 1.10-fold greater than x, b is not at least about 1.10-fold greater than y, c is not at least about 1.10-fold greater than z, and/or d is not at least about 1.05-fold greater than v and/or e is not at least about 1.05-fold greater than w; a is not at least about 1.10-fold greater than x, b is not at least about 1.10-fold greater than y, c is not at least about 1.10-fold greater than z, and/or d is at least about 1.05-fold greater than v and/or e is at least about 1.05-fold greater than w; and/or a is at least about 1.10-fold greater than x, b is at least about 1.10-fold greater than y, and/or c is at least about 1.10-fold greater than z, and/or d is not at least about 1.05-fold greater than v and/or e is not at least about 1.05-fold greater than w).

The present disclosure documents, among other things, that technologies provided herein can achieve reduced levels of dsRNA in IVT reactions. In some embodiments, IVT reactions utilizing reactions mixtures comprising elevated levels of ATP lead to decreased levels of dsRNA (e.g., relative to an appropriate comparator, e.g., an IVT reaction utilizing a standard reaction mixture as described herein). In some embodiments, IVT reactions utilizing reactions mixtures comprising elevated levels of CTP lead to decreased levels of dsRNA (e.g., relative to an appropriate comparator, e.g., an IVT reaction utilizing a standard reaction mixture as described herein). In some embodiments, IVT reactions utilizing reactions mixtures comprising elevated levels of CTP and/or ATP lead to decreased levels of dsRNA (e.g., relative to an appropriate comparator, e.g., an IVT reaction utilizing a standard reaction mixture as described herein).

In particular embodiments, the present disclosure documents that provided technologies (e.g., elevated CTP and/or ATP levels, and in particular elevated ATP levels in reaction mixtures) can achieve reduced dsRNA levels. Furthermore, the present disclosure documents that such benefits can be achieved in production of various RNA transcripts, with different C and/or A content. Thus, in some such embodiments, technologies provided herein achieve reduced dsRNA levels in an IVT reaction independent of nucleotide content of the produced RNA; in some such embodiments, nucleotide content of the produced RNA is assessed excluding any poly(A) tail.

Capping

In some embodiments, capping of RNA molecules (e.g., produced by the technologies of the present disclosure) is assessed and/or monitored (e.g., determined at one or more points over time). In some embodiments, capping of in vitro transcribed RNA can be verified, for example, by assessing translation (which typically requires presence of a functional cap). In some embodiments, a biological activity test, for example that may be performed during process characterization of animal trial materials, is confirmatory that the RNA is translated into a polypeptide (e.g., protein) of correct size. In some embodiments, capping of in vitro transcribed RNA is assessed by conducting a nuclease-based assay. In some embodiments, capping of in vitro transcribed RNA is assessed by conducting a catalytic nucleic acid-based assay. Alternatively or additionally, in some embodiments, non-clinical studies are performed to demonstrate capping of various different mRNA batches.

In some embodiments, capping of RNA molecule (e.g., as produced by technologies disclosed herein) is assessed by (a) assessing translation of functionally capped RNA; (b) performing a biological activity test to confirm the RNA molecule is translated into a polypeptide (e.g., protein) of correct size; (c) conducting a nuclease-based assay; and/or (d) conducting a catalytic nucleic acid-based assay.

In some such embodiments, a nuclease-based assay comprises an RNase-based assay. In some such embodiments, an RNase-based assay comprises one or more of: (a) annealing a multitude of RNA molecules to one or more probes binding the RNA molecules to form RNA-probe complexes; (b) digesting the RNA-probe complexes with RNase to generate fragments comprising the 5' terminus of the RNA molecules; (c) purifying the fragments using affinity-based purification, chromatography-based purification, or a combination thereof, (d) subjecting the purified fragments to mass spectrometry (MS); (e) identifying capped and uncapped fragments based on observed MS values; and/or (f) comparing the amount of capped and uncapped fragments to calculated the percentage of capped RNA. In some embodiments, an RNase comprises RNase H.

In some embodiments, a nuclease-based assay comprises one or more of: (a) contacting a multitude of the RNA molecules with one or more DNA oligonucleotides complementary to a sequence in a 5' untranslated region of the RNA molecules adjacent to a 5' RNA cap or an uncapped penultimate base of the RNA; (b) annealing the one or more DNA oligonucleotides to the sequence in the 5' untranslated region of the RNA molecules to form DNA/RNA hybrid complexes; (c) degrading the DNA/RNA hybrid complexes and/or unannealed RNA molecules with one or more nucleases to produce capped and uncapped 5' terminal RNA fragments and 3' RNA fragments; (d) separating the capped and uncapped 5' terminal RNA fragments from the 3' RNA fragments using affinity-based purification, chromatography-based purification, or a combination thereof, and/or (e) comparing the amount of capped and uncapped 5' terminal RNA fragments to calculate the percentage of capped RNA.

In some embodiments, catalytic nucleic acid-based assay comprises one or more of: (a) cleaving a multitude of RNA molecules with a catalytic nucleic acid molecule into 5' terminal RNA fragments and at least one 3' RNA fragments, wherein the RNA molecules have a cleavage site for a catalytic nucleic acid molecule; (b) separating the 5' terminal RNA fragments and 3' RNA fragments using affinity-based purification, chromatography-based purification, or a combination thereof, (c) measuring the amount of capped and uncapped 5' terminal RNA fragments using spectroscopy, quantitative mass spectrometry, sequencing, or a combination thereof, and/or (d) comparing the amount of capped and uncapped 5' terminal RNA fragments to calculate the percentage of capped RNA. In some such embodiments, the catalytic nucleic acid molecule comprises a DNAzyme or a ribozyme.

In some embodiments, at least about 40%, 50%, 60%, 70%, 80%, 90%, or 99% of the RNA molecules produced in accordance with technologies provided herein are capped. In some embodiments, capping of the RNA molecules produced in accordance with technologies provided herein is increased at least about 1%, 2%, 3%, 4%, 5%, 6%, 7%, 8%, 9%, or 10% relative to an appropriate comparator (e.g., an otherwise comparable in vitro transcription reaction, for example utilizing a reaction mixture in which a is not at least 1.25, b is not at least 1.25, and/or c is not at least 1.10). In some embodiments, capping of the RNA molecules produced in accordance with technologies provided herein is increased at least about 1%, 2%, 3%, 4%, 5%, 6%, 7%, 8%, 9%, or 10% relative to an appropriate comparator (e.g., an otherwise comparable in vitro transcription reaction, for example utilizing a reaction mixture in which a is not at least about 1.10-fold greater than x, b is not at least about 1.10-fold greater than y, and/or c is not at least about 1.10-fold greater than z). In some embodiments, capping of the RNA molecules produced in accordance with technologies provided herein is increased at least about 5% relative to an appropriate comparator.

Yield

In some embodiments, yield of RNA molecules produced by technologies of the present disclosure is assessed. In some embodiments, yield is determined as g/L starting IVT volume) In some embodiments, yield is determined by measuring total amount of RNA generated in an IVT reaction relative to the theoretical value of RNA calculated to be produced by the IVT reaction. In some embodiments, yield is determined according to the equation:

Estimated RNA Yield (e.g., mg/mL)=$(D) \times (W) \times (Z)/(X)=(Y)$;

wherein (D), (W) (e.g., mg/mL), Z (e.g., mL), X (e.g., mL), and Y (e.g., mg/mL) represent: the dilution factor that was used to re-suspend the pellet (e.g., in water, e.g., RNase free water), RNA concentration (e.g., measured by ARD), the theoretical total reaction volume after proteinase K digestion step, the initial volume of the IVT process, and yield, respectively.

In some embodiments, yield is at least about 70%, 75%, 80%, 85%, 90%, 95%, 100%, 105%, 110%, 115%, 120%, 125% or more of the theoretical value or more. In some embodiments, yield is about 70-125%, 75-125%, 80-125%, 85-125% 70-120%, 75-120%, 80-120%, or 85-120%. In some embodiments, yield (g/L starting IVT volume) is greater than or equal to 3.30, 3.31, 3.32, 3.33, 3.34, 3.35, 3.36, 3.37, 3.38, 3.39, 3.40, 3.50, 3.60, 3.70, 3.80, 3.90, 4.0 or greater.

Use

In some embodiments, RNA (e.g., therapeutic RNA, e.g., mRNA) produced by technologies of the present disclosure has an increase in yield, integrity, and/or capping and/or decreased formation of aberrant products and/or contaminants (e.g., dsRNA). In some embodiments, RNA produced is pharmaceutical-grade RNA. In some embodiments, RNAs produced by technologies of the present disclosure can be used as therapeutic agents to treat or prevent infection (e.g., bacterial, viral) and/or diseases and/or disorders. In some embodiments, RNAs as described herein can be used as therapeutic agents to treat and/or prevent conditions associated with infections and/or diseases and/or disorders.

In some embodiments, RNAs produced by technologies of the present disclosure may be useful to detect and/or characterize one or more of the features of an immune response (e.g., by detecting binding to a provided antigen by serum from a subject with an infection and/or disease and/or disorder).

In some embodiments, RNAs produced by technologies of the present disclosure are useful to raise antibodies to one or more epitopes included herein; such antibodies may themselves be useful, for example, for detection and/or treatment of infection and/or disease and/or disorders.

In some embodiments, the present disclosure provides use of RNAs to produce encoded antigens and/or use of DNA constructs to produce RNA.

EXEMPLIFICATION

Example 1: Exemplary Reference In Vitro Transcription (IVT) Reactions

The present Example provides an exemplary reference IVT reaction.

In some embodiments, a reference (e.g., control or standard) IVT reaction was performed in the presence of a DNA template (linearized plasmid), m2$^{7,3'\text{-}O}$Gppp(m$^{2'\text{-}O}$)ApG (CC413) cap analog (1.5 mM) for co-transcriptional capping and nucleoside triphosphates (GTP, ATP, and m1ΨTP) at the final concentration of 9 mM each. Starting concentrations of GTP/m1ΨTP were reduced to 0.5 mM (1/18*9 mM) of the starting concentration and fed over the course of the transcription reaction in 11 additions until the final concentrations were reached. The reaction was performed for 105 minutes at 37° C. with HEPES buffer (40 mM, pH 8.3) containing Magnesium Acetate (MgAc, 40 mM), dithiothreitol, and spermidine in the presence of a T7 RNA polymerase, RNAse inhibitor (Ribolock) and inorganic pyrophosphatase (0.0001 U/μl). After IVT, the DNA template was removed via DNase digestion and the RNA was purified using Magnetic beads for immobilization (see, for example, Berensmeier, S. Magnetic particles for the separation and purification of nucleic acids. Appl.Microbiol.Biotechnol. 73, 495-504; 10.1007/s00253-006-0675-0 (2006)). RNA was eluted in water.

Constructs utilized were BNT162b1 or BNT162b2 (see, for example, Shoura et al. *Assemblies of putative SARS-CoV-2-spike-encoding mRNA sequences for vaccines BNT-162b2 and mRNA-1273*, PCT/EP21/59947, U.S. Ser. No. 17/233,396).

Example 2: Exemplary Methods of Producing an RNA by In Vitro Transcription (IVT)

The present Example demonstrates exemplary methods of producing RNA by IVT utilizing strategies as described herein.

Figure 7:
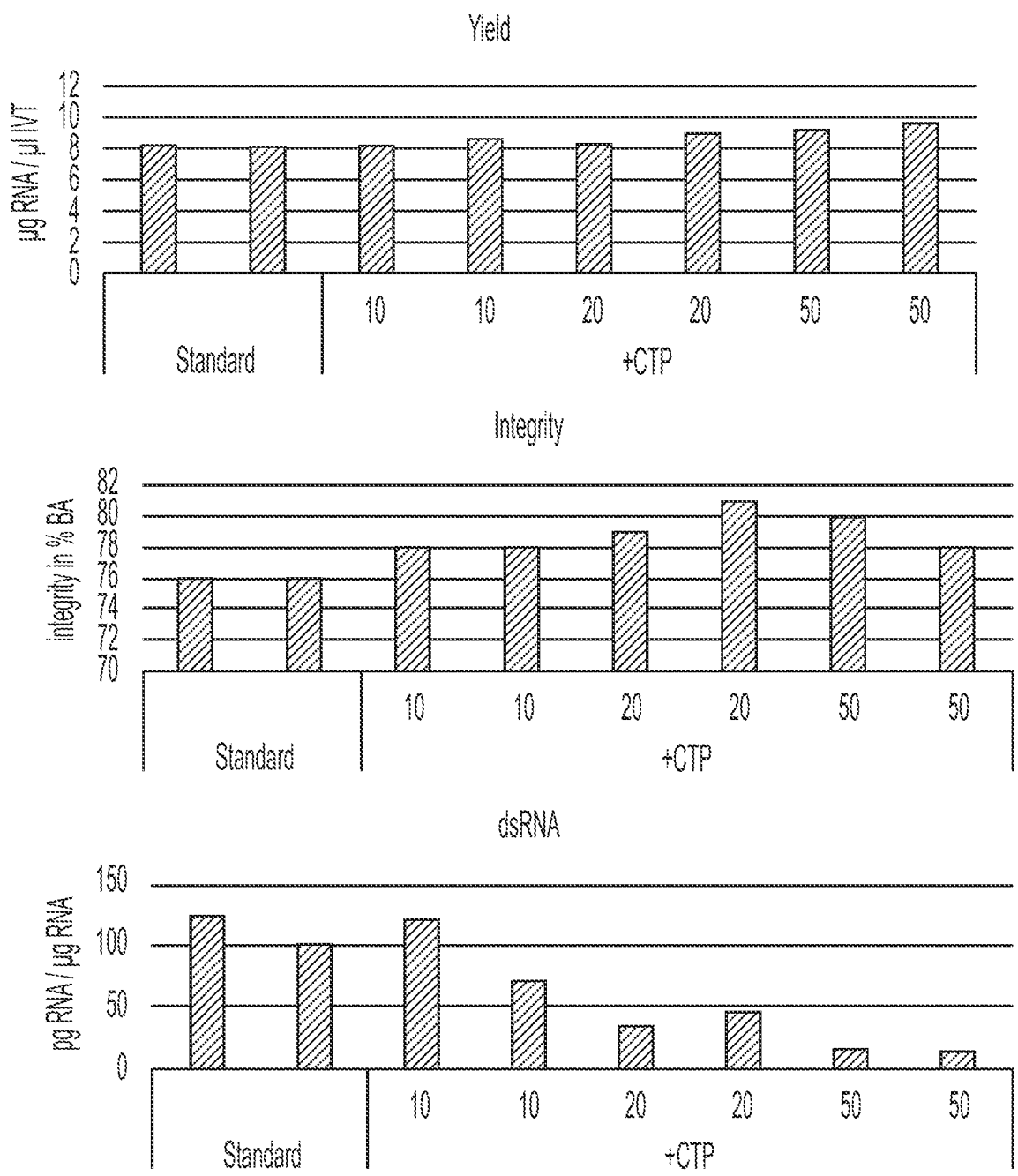
FIG. 7 shows yield (top), RNA integrity (middle), and residual double-stranded RNA (bottom)) from exemplary IVT reactions utilizing conditions summarized in FIG. 1. Exemplary IVT reactions compared reaction mixtures comprising either +10%, +20%, or +50% CTP relative to control (+0% CTP). Starting concentrations of GTP/m1ΨTP were reduced to 0.5 mM (1/18*9 mM) of the starting concentration and fed over the course of the transcription reaction in 11 additions until the final concentrations were reached.

An IVT reaction was conducted using N1-methyl-pseudouridine (m1ψTP) fed-batch. IVT reaction mixture components and conditions are summarized in FIG. 1. Those skilled in the art, reading the present disclosure (e.g., with reference to FIGS. 7 and/or 17) will appreciate that, in some embodiments, dsRNA may be lower when elevated C is used, when elevated A is used, and/or when both elevated C and elevated A are used. In some embodiments, dsRNA may be decreased (e.g., by an amount within a range of about 25 to about 50 pg dsRNA/μg RNA) when C is used at a concentration within a range of, for example, +10% to +50%, relative to an appropriate comparator as described herein. In some embodiments, dsRNA may be decreased (e.g, by an amount within a range of about 0-10 pg dsRNA/μg RNA) when A is used at a concentration with a range of, for example, +20% to +50% relative to an appropriate comparator as described herein. In some embodiments, dsRNA may be decreased (e.g., by an amount within a range of about 0 to about 10 pg dsRNA/μg RNA) when C is used at a concentration within a range of, for example, +10% to +50%, and A is used at a concentration within a range of, for example, +20 to +50%, relative to an appropriate comparator as described herein.

Residual nucleotide triphosphates (NTPs) following an exemplary, large-scale IVT production (37.6 L) was analyzed for two constructs (FIG. 2).

Example 3: Exemplary IVT Reaction Mixtures with Increased CTP and/or ATP

The present Example provides exemplary IVT reactions wherein the starting volume of ATP and/or CTP in the reaction mixture was adjusted from a control reaction as described in Example 1 (the nomenclature "+0%" CTP and/or ATP is used to indicate the control conditions). Exemplary RNA was synthesized from a DNA template using IVT and additionally processed by steps comprising a DNAse I digestion (e.g., to remove DNA template) and a Proteinase K digestion (e.g., to facilitate removal of proteins, e.g., polymerase, by ultrafiltration/diafiltration). Reaction samples were taken after the proteinase K digestion step and purified for analysis. IVT was conducted in a microbioreactor (e.g., AMBR15®) according to the conditions summarized in Table 2.1.

TABLE 2.1

Summary of exemplary model method

| IVT Operational Step | Process Parameter | Units | AMBR15 ® Target |
|---|---|---|---|
| In Vitro Transcription | Initial Reaction Volume | mL | 8 |
| | Temperature | ° C. | 37 |
| | 5'-Cap Volume | mL | 0.12 |
| | CTP Volume | mL | 0.72 |
| | ATP Volume | mL | 0.72 |
| | Initial N1-methylpseudo UTP Volume | mL | 0.04 |
| | Initial GTP Volume | mL | 0.04 |
| | 10× Transcription Buffer Volume | mL | 0.8 |
| | DNA Concentration | mg/mL | 0.1 |
| | RNase Inhibitor Volume | mL | 0.01 |
| | Pre-Enzyme Agitation Rate | Rpm | 420 |
| | Pyrophosphatase Volume | mL | 0.008 |
| | T7 Polymerase Volume | mL | 0.64 |
| | Agitation rate | Rpm | 420 |
| | Incubation Time During GTP/N1-methylpsuedo UTP Bolus Feeds | min:sec | 75:00 |
| | Time Between GTP/N1-methylpsuedo UTP Bolus Feeds | min:sec | 6:15 |
| | GTP/N1-methylpseudo UTP Volume Per Bolus Feed | mL | 0.124 |
| | Total GTP/N1-methylpseudo UTP Bolus Volume | mL | 1.364 |
| | Total GTP/N1-methylpseudo UTP Bolus Additions | Number of Feeds | 11 |
| | Final IVT Incubation Time | min:sec | 30:00 |
| DNase 1 Digestion | Temperature | ° C. | 37 |
| | Agitation Rate | rpm | 420 |
| | DNase Volume | mL | 0.060 |
| | CaCl2 Volume | mL | 0.017 |
| | Incubatiuon Time | min:sec | 35:00 |
| | EDTA Volume | mL | 1.245 |
| | EDTA Incubation Time | min:sex | 1:00 |
| Proteinase K Digestion | Temperature | ° C. | 37 |
| | Agitation Rate | rpm | 420 |
| | Proteinase K Volume | mL | 0.008 |
| | Incubation Time | min:sec | 10:00 |

Produced RNA samples were analyzed for RNA concentration, RNA integrity, 5'-capping, residual NTPs, and poly (A) tail integrity. Without wishing to be bound by any one theory, these characteristics were selected for analysis due to their potential impact from the change in CTP concentration. To calculate RNA yield for each scale, the below equation was utilized:

Estimated RNA Yield (mg/mL)=$(D) \times (W) \times (Z)/(X)$=$(Y)$ wherein (D), W (mg/mL), Z (mL), X (mL), and Y (mg/mL) represent the dilution factor utilized to re-suspend the RNA in water. The theoretical total reaction volume after proteinase K digestion step, the initial volume of the IVT process, and yield, respectively. To minimize the impact of sampling on yield at small scale, theoretical total reaction volume was used to estimate the total amount of RNA produced in the IVT process.

Samples for residual NTP analyses were taken post-Proteinase K digestion. Upon residual NTP analysis, CTP- was identified to be below the limit of quantitation (Table 2.2).

TABLE 2.2

Nucleotide results from two exemplary manufacturing runs post-Proteinase K digestion.

| Parameter | Run 1 | Run 2 |
|---|---|---|
| ATP concentration (µM) | 1324.6 | 1215.0 |
| CTP concentration (µM) | NMT 125.0 | NMT 125.0 |

TABLE 2.2-continued

Nucleotide results from two exemplary manufacturing runs post-Proteinase K digestion.

| Parameter | Run 1 | Run 2 |
|---|---|---|
| GTP concentration (µM) | 903.7 | 838.2 |
| modUTP concentration (µM) | 2544.7 | 2357.2 |

To improve produced RNA based on observed CTP depletion, CTP concentration in an IVT reaction mixtures was evaluated from 10% less CTP volume to 50% additional CTP volume relative to control/standard (+0% CTP) (Table 2.3).

TABLE 2.3

Exemplary conditions assessed in exemplary CTP study

| CTP volume (% from target) | Concentration of CTP (mM) | Scaled volume of 100 mM CTP solution added (mL/L starting volume) |
|---|---|---|
| −10 | 8.1 | 81 |
| 0 (control) | 9 | 90 |
| +10 | 9.9 | 99 |
| +20 | 10.8 | 108 |
| +50 | 13.5 | 135 |

Figure 3:
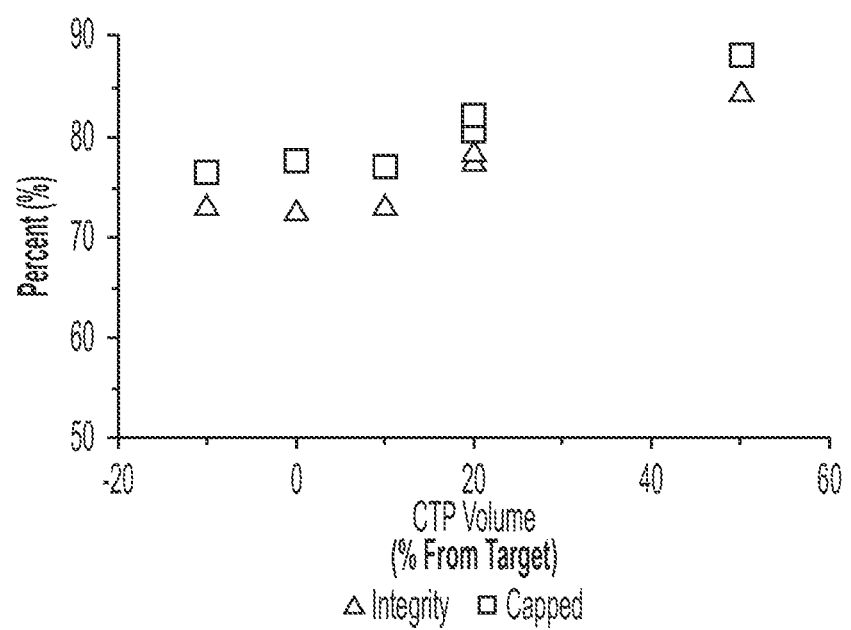
FIG. 3 shows RNA integrity and percent capping of RNA produced from exemplary IVT reactions utilizing IVT reaction mixtures comprising either −10%, +10%, +20%, or +50% CTP volume relative to a control (e.g., standard) IVT reaction mixture comprising +0% CTP volume. These reactions showed that increasing CTP volume led to increased RNA integrity and capping at +20% CTP volume and +50% CTP volume, but were relatively stable at +/−10% CTP starting concentration compared to RNA produced using the control IVT reaction mixture.
Figure 4:
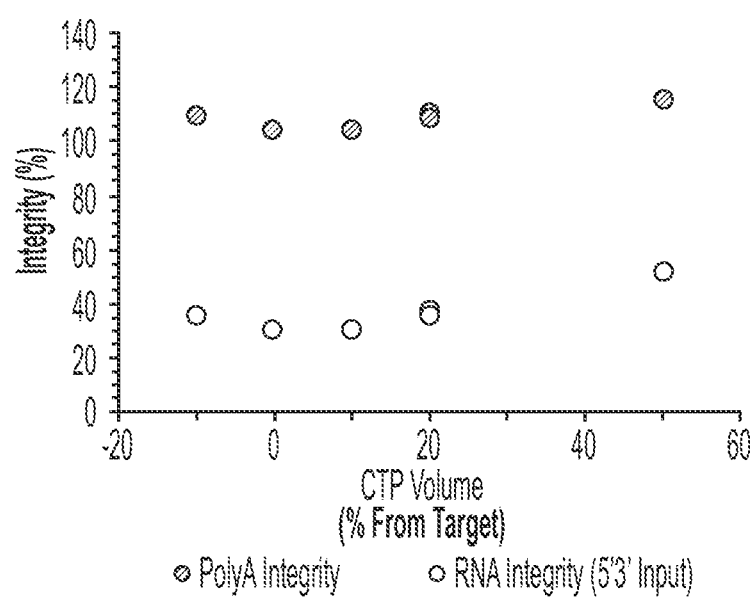
FIG. 4 shows PolyA integrity and RNA integrity of RNA produced from exemplary IVT reactions utilizing IVT reaction mixtures comprising either −10%, +10%, +20%, or +50% CTP volume relative to a control (e.g., standard) IVT reaction mixture comprising +0% CTP volume. Increasing CTP resulted in increased poly(A) and RNA integrity of the produced RNA relative to control.
Figure 5:
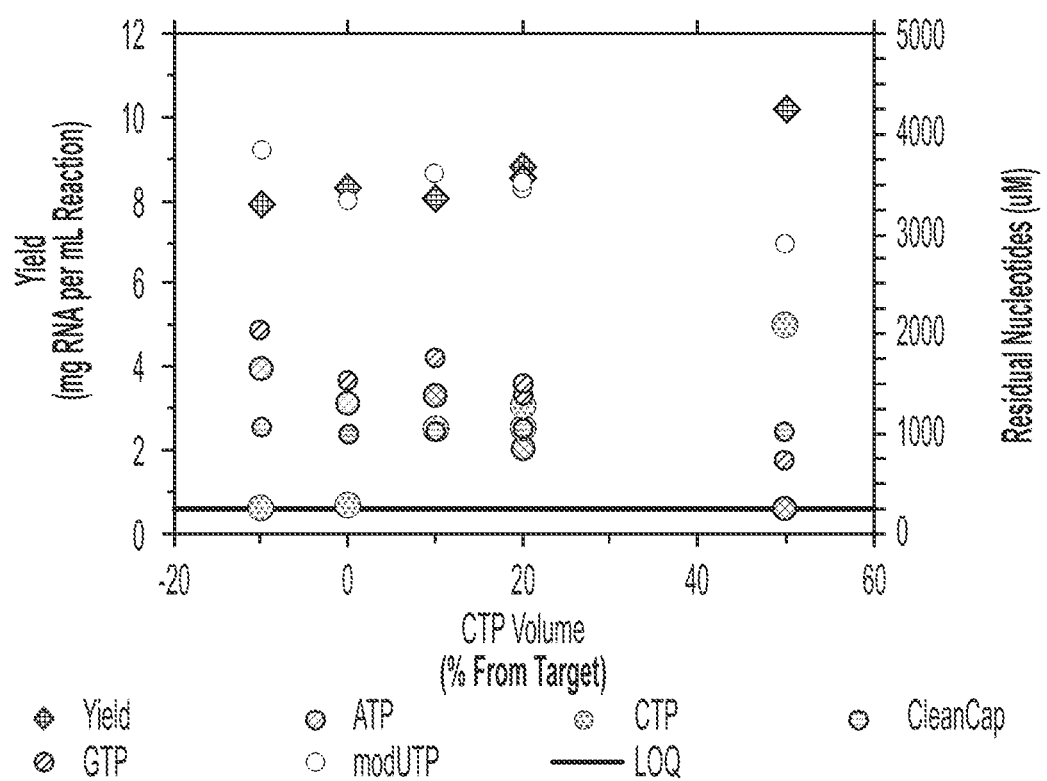
FIG. 5 shows residual NTP and cap levels as well as yield from exemplary IVT reactions utilizing IVT reaction mixtures comprising either −10%, +10%, +20%, or +50% CTP volume relative to a control (e.g., standard) IVT reaction mixture comprising +0% CTP volume. An increase in yield was observed with increasing CTP concentration. Increasing CTP volume above control resulted in maintenance of CTP concentrations above the limit of quantitation. Higher CTP concentrations resulted in ATP concentrations below the limit of quantitation.

RNA produced from the varying exemplary conditions of Table 2.3 were then assessed for RNA integrity and capping. Increasing CTP volume demonstrated increased integrity and capping at +20% CTP volume and +50% CTP volume, but were relatively stable at +/−10% CTP starting concentration (FIG. 3). Additionally, RNA produced was assessed for Poly(A) integrity and RNA integrity by digital droplet polymerase chain reaction (ddPCR). Increasing CTP resulted in increased poly(A) and RNA integrity of the produced RNA (FIG. 4). An increase in yield was also observed with increasing CTP concentration (FIG. 5). Increasing CTP volume above control (+0%) also resulted in maintenance of CTP concentrations above the limit of quantitation (FIG. 5). However, higher CTP concentrations (e.g., +50% from control), resulted in ATP concentrations below the limit of quantitation (FIG. 5).

Additional studies further demonstrated that an increase in CTP starting concentration (+10% CTP, +20% CTP, +50% CTP relative to control) in an exemplary IVT reaction mixture resulted in increased integrity and capping. Yield was also evaluated and further confirmed increasing CTP starting concentration results in increased yield (FIG. 6).

Further exemplary IVT reactions were performed in the presence of a DNA template (linearized plasmid), m2$^{7,3'}$-oGppp(m$^{2'-O}$)ApG (CC413) cap analog (1.5 mM) for co-transcriptional capping and nucleoside triphosphates (GTP, ATP, and m1ΨTP) at the final concentration of 9 mM each. The starting CTP concentration was 9 mM (standard/control), 9.9 mM (+10%), 10.8 mM (+20%) and 13.5 mM (+50%). The starting concentrations of GTP/m1ΨTP were reduced to 0.5 mM (1/18*9 mM) of the starting concentration and fed over the course of the transcription reaction in 11 additions until the final concentrations were reached; without wishing to be bound by any particular theory, we propose that such an approach may enhance capping efficiency and/or reduce dsRNA. The reaction was performed for 105 minutes at 37° C. with HEPES buffer (40 mM, pH 8.3) containing Magnesium Acetate (MgAc, 40 mM), dithiothreitol, and spermidine in the presence of a T7 RNA polymerase, RNAse inhibitor (Ribolock) and inorganic pyrophosphatase (0.0001 U/μl). After IVT, the DNA template was removed via DNase digestion and the RNA was purified using Magnetic beads for immobilization (see, for example, Berensmeier, S. Magnetic particles for the separation and purification of nucleic acids. Appl. Microbiol. Biotechnol. 73, 495-504; 10.1007/s00253-006-0675-0 (2006)). RNA was eluted in water. RNA concentration was measured by UV (Nanodrop) and the yield of the IVT was calculated (produced RNA in μg/IVT reaction volume in μl). RNA integrity was analyzed on an Agilent Bioanalyzer. For this, 250 ng of RNA in 50% Formamid was denatured for 10 minutes at 70° C. and processed further with the Agilent RNA 6000 Nano Kit (5067-1511, Agilent). Integrity was later calculated by the relation for the main peak integral against the integral of the complete electorpherogram. To determine the amount of dsRNA, 1 μg of RNA was spotted in 5 μl aliquots onto a nylon blotting membrane (Nytran SuPerCharge (SPC) Nylon Blotting Membrane (GE Healthcare Life Sciences, Cat #10416216). The membrane was then blocked for 1 h in TBS-T buffer (20 mM TRIS pH 7.4, 137 mM NaCl, 0.1% (v/v) TWEEN-20) containing 5% (w/v) skim milk powder. For detection of dsRNA the membrane was incubated for 1 h with J2 dsRNA-specific mouse mAb (English & Scientific Consulting, Szirák, Hungary) diluted 1:10,000 in TBS-T buffer containing 1% (w/v) skim milk powder. After washing with TBS-T the membrane was incubated for 1 h with HRP-conjugated donkey anti-mouse IgG (Jackson ImmunoResearch, Cat #715-035-150) diluted 1:10,000 in TBS-T buffer containing 1% (w/v) skim milk powder, washed with TBS-T and developed using Amersham ECL Prime Western Blotting Detection Reagent (Fisher Scientific, Cat #RPN2232) and the ChemiDoc MP Imaging system (BIO-RAD).

Enrichment of CTP levels in exemplary IVT reaction mixtures enhanced produced RNA yield (FIG. 7A). Without wishing to be bound by any one theory, this indicates that the reduction of CTP during the IVT reaction reaches a point that less RNA can be produced. Increasing the CTP starting concentration can circumvent this effect. The same effect can be seen for the integrity. Here, limiting CTP levels reduces the integrity, most likely through non-finished RNA transcript. Again, this effect can be rescued by the elevation of CTP levels (FIG. 7B). As an additional positive effect, increasing the CTP starting concentration reduces the dsRNA formation (FIG. 7C). One insight provided by the present disclosure is that use of elevated CTP and/or ATP, as described herein, may provide certain advantages even independent of depletion. Thus, in some embodiments, the present disclosure provides an insight that provided reaction conditions may be utilized independent of construct sequence (e.g., in some embodiments, when C and/or A is/are present in a transcript at a lower level and/or relevant ratio [as recited herein] than in the reaction mix) Among other things, this insight provides standardized IVT production technologies, as described herein, with particular advantages and efficiencies for commercial grade and/or scale production. For example, ability to utilize comparable conditions and/or components for various multiple productions (e.g., of different RNA transcript products) can significantly facilitate and/or improve reproducibility, feasibility, and/or reliability of such commercial grade and/or scale production.

Increasing CTP concentration not only enhanced integrity, but also enhanced yield and reduced dsRNA content.

Additional IVT reaction mixtures comprising increased CTP concentrations were evaluated. All attributes were measured post-proteinase K digestion.

TABLE 2.4

Conditions tested

| CTP volume (% from target) | Concentration of CTP (mM) | Scaled volume of 100 mM CTP solution added (mL/L starting volume) |
|---|---|---|
| 0 (control) | 9 | 90 |
| +40 | 12.6 | 126 |
| +50 | 13.5 | 135 |
| +60 | 14.4 | 144 |

Figure 8:
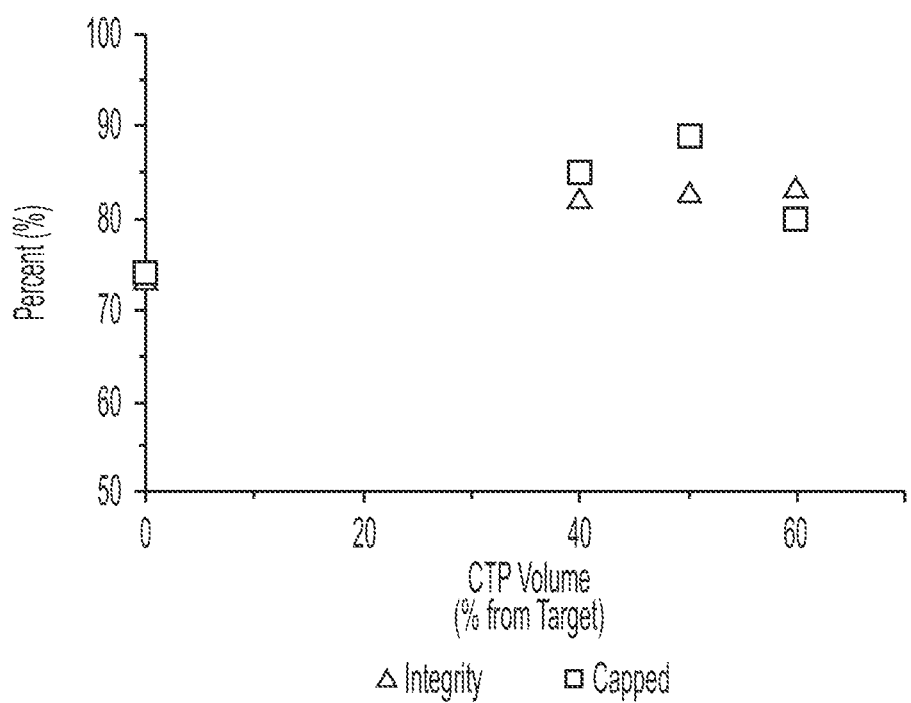
FIG. 8 shows RNA integrity and percent capping of RNA produced from exemplary IVT reactions utilizing IVT reaction mixtures comprising either +40%, +50%, or +60% CTP volume relative to a control (e.g., standard) IVT reaction mixture comprising +0% CTP volume.
Figure 9:
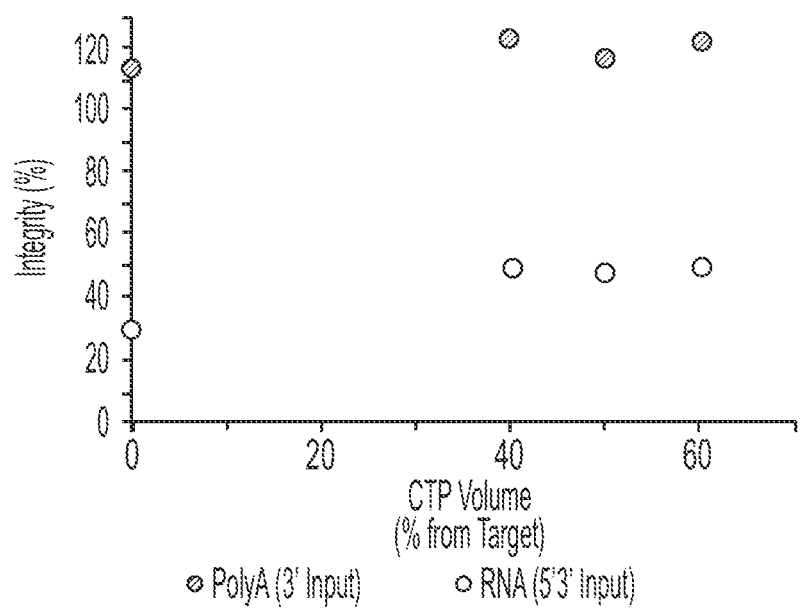
FIG. 9 shows PolyA integrity and RNA integrity of RNA produced from exemplary IVT reactions utilizing IVT reaction mixtures comprising either +40%, +50%, or +60% CTP volume relative to a control (e.g., standard) IVT reaction mixture comprising +0% CTP volume.
Figure 10:
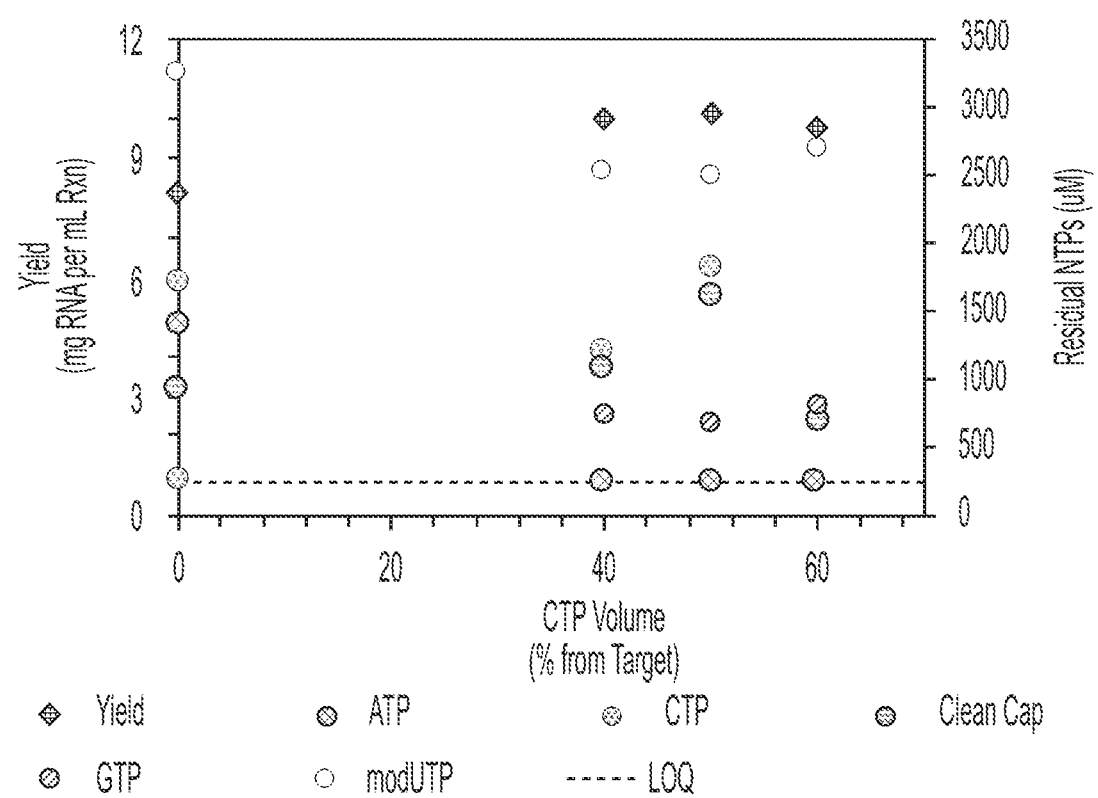
FIG. 10 shows residual NTP and cap levels as well as yield from exemplary IVT reactions utilizing an IVT reaction mixtures comprising either +40%, +50%, or +60% CTP volume relative to a control (e.g., standard) IVT reaction mixture comprising +0% CTP volume.

RNA produced from the varying exemplary conditions of Table 2.4 were assessed for integrity and capping by CTP volume as measured post-Proteinase K digestion (FIG. 8). Additionally, RNA produced was assessed for Poly(A) integrity and RNA integrity by digital droplet polymerase chain reaction (ddPCR). Increasing CTP resulted in increased poly(A) and RNA integrity of the produced RNA (FIG. 9). While the +40% to +60% CTP comprising IVT reaction mixtures shows very little difference between these conditions for integrity (by fragment analyzer), 5'-cap, poly (A) tail, and integrity by ddPCR, these conditions do show improvement over the control IVT reaction mixture (+0% IVT). FIG. 10 shows yield increases over the control for the +40% to +60% IVT reaction mixtures, but is consistent amongst the +40% to +60% range. Residual nucleotide analysis showed all conditions continued to deplete ATP (FIG. 10).

Figure 11:
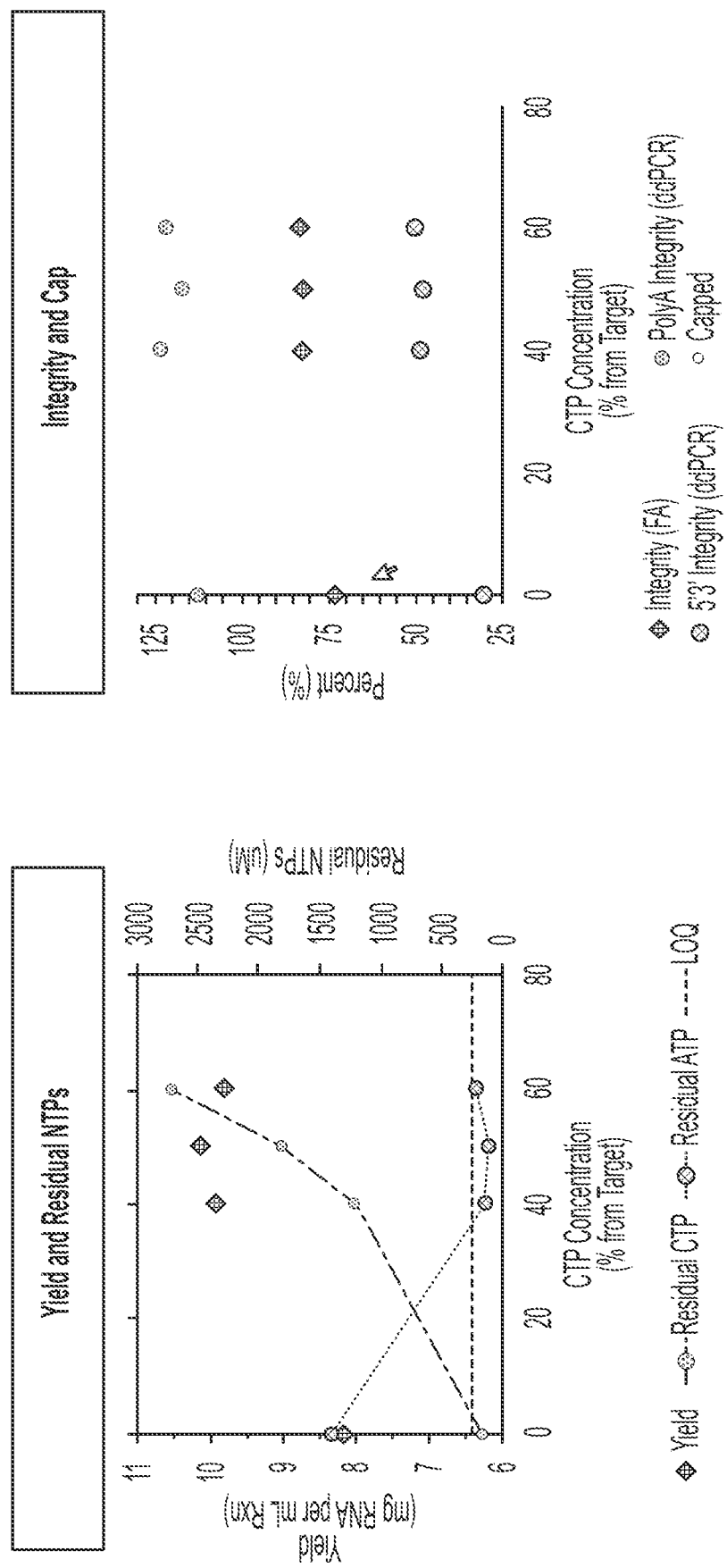
FIG. 11 shows additional exemplary studies demonstrating RNA integrity and percent capping as well as yield and residual CTP levels from exemplary IVT reactions utilizing IVT reaction mixtures comprising either +40%, +50%, or +60% CTP volume relative to a control (e.g., standard) IVT reaction mixture comprising +0% CTP volume. Increasing CTP to +40%, +50%, and +60% CTP volume depleted ATP below limit of quantitation, increased yield to 10 mg/mL, and increased integrity (FA) from 73.4% to 83.4%.

Additional studies further demonstrated that an increase in starting CTP concentration (+40% CTP, +50% CTP, +60% CTP relative to control) in an exemplary IVT reaction mixture resulted in increased yield and residual CTP, while ATP became the limiting NTP in this reaction. Interestingly, there was no further yield or integrity improvement observed in these reactions mixtures with more than +40% CTP. Integrity and capping of RNAs produced by IVT reaction mixtures with increased starting CTP concentration were increased relative to control (FIG. 11).

To evaluate exemplary produced RNA by IVT with increased CTP and ATP, IVT reactions were conducted with +50% CTP volume and increased ATP volumes in the reaction mixtures. Without wishing to be bound by any one theory, ATP may be particularly important, among other reasons, for synthesis of the Poly(A) tail. Conditions tested to evaluated the effect of additionally increasing ATP volume is summarized in Table 2.5.

TABLE 2.5

Exemplary conditions tested with increasing ATP volume

| ATP volume (% from target) | Concentration of ATP (mM) | Scaled volume of 100 mM ATP solution added (mL/L starting volume) |
|---|---|---|
| 0 (control) | 9 | 90 |
| +10 | 9.9 | 99 |
| +20 | 10.8 | 108 |

Figure 12:
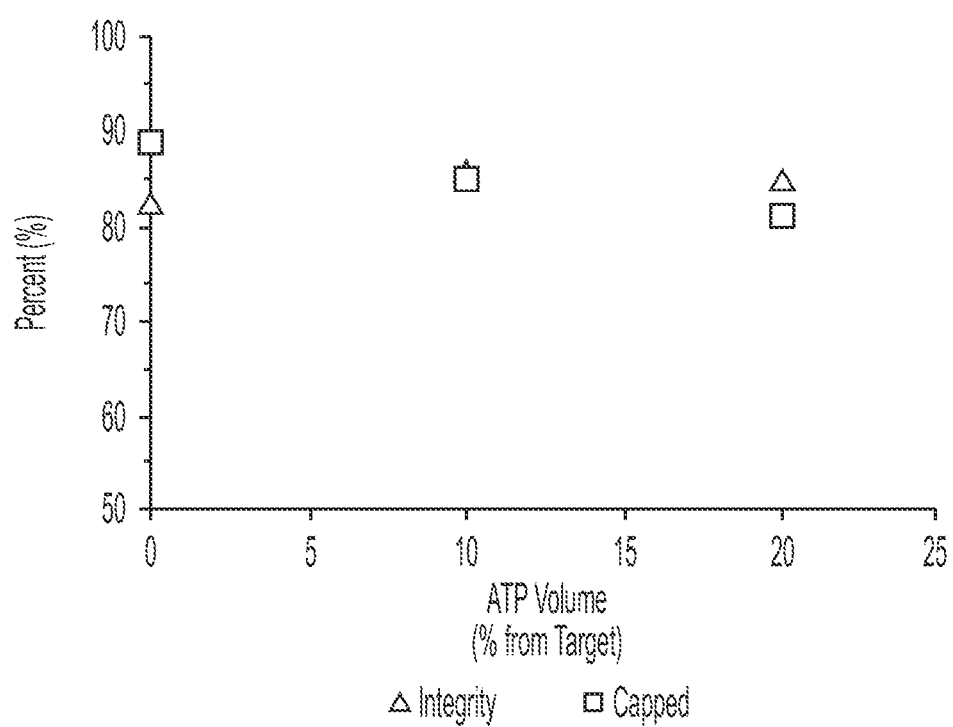
FIG. 12 shows RNA integrity and percent capping of RNA produced from exemplary IVT reactions utilizing IVT reaction mixtures comprising either +50% CTP volume and +10% ATP volume or +50% CTP volume and +20% ATP volume relative to a control IVT reaction mixing comprising +50% CTP volume and +0% ATP volume.
Figure 13:
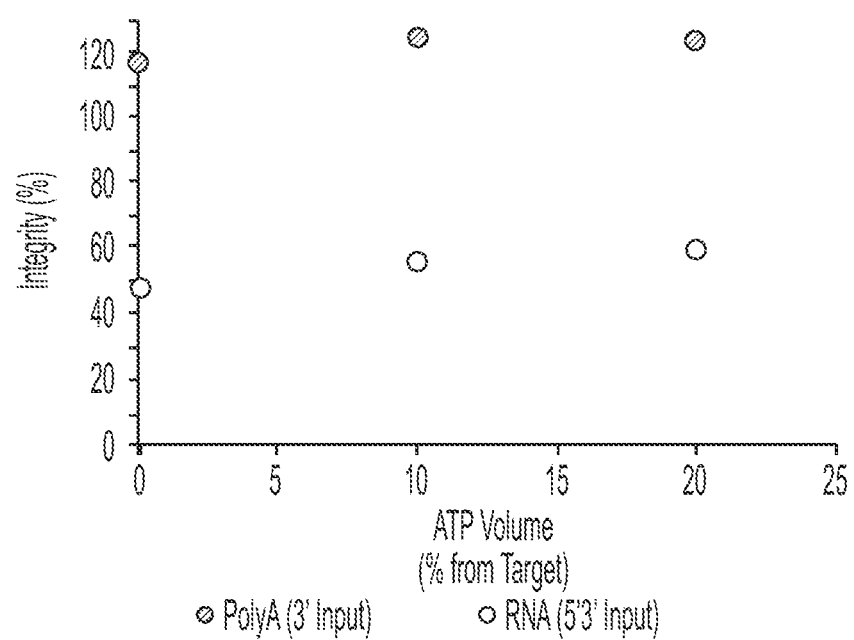
FIG. 13 shows PolyA integrity and RNA integrity of RNA produced from exemplary IVT reactions utilizing IVT reaction mixtures comprising either +50% CTP volume and +10% ATP volume or +50% CTP volume and +20% ATP volume relative to a control IVT reaction mixing comprising +50% CTP volume and +0% ATP volume.
Figure 14:
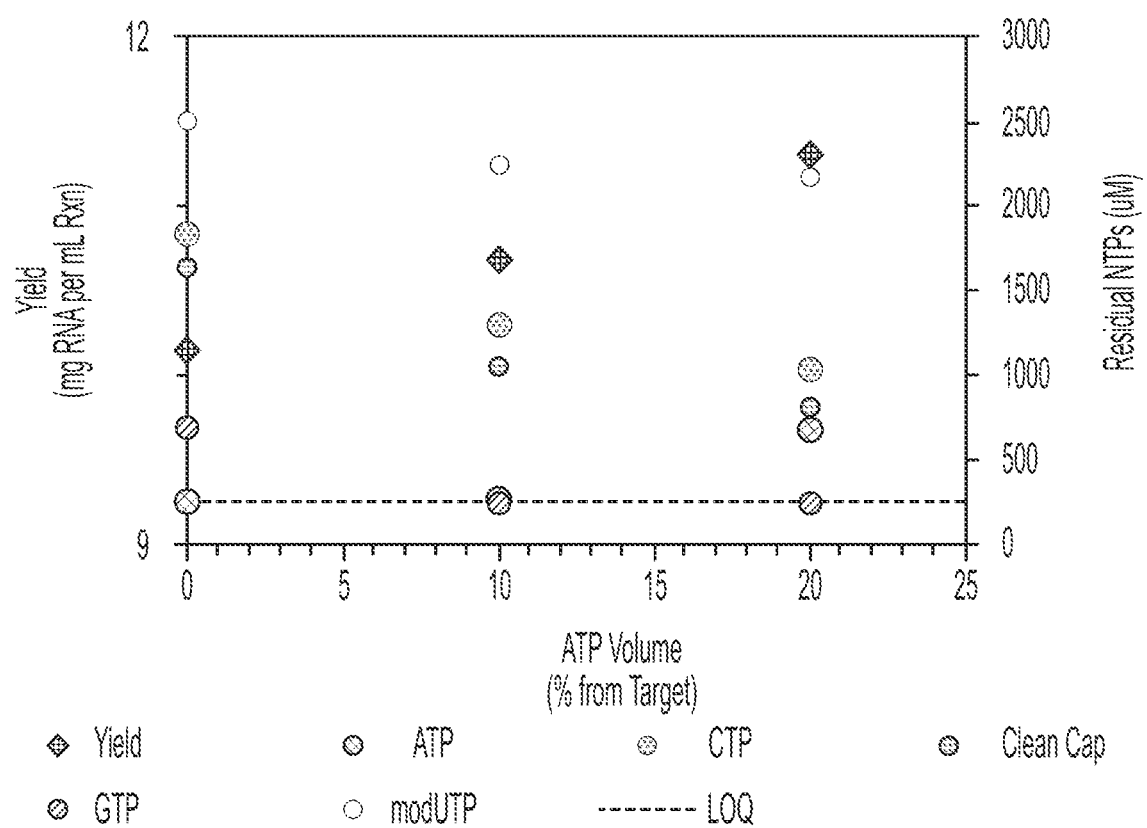
FIG. 14 shows additional exemplary studies demonstrating RNA integrity and percent capping as well as yield and residual NTP levels from exemplary IVT reactions utilizing IVT reaction mixtures comprising either +50% CTP volume and +10% ATP volume or +50% CTP volume and +20% ATP volume relative to a control IVT reaction mixing comprising +50% CTP volume and +0% ATP volume.

RNA produced from the varying exemplary conditions of Table 2.5 were then assessed for integrity and capping by CTP volume as measured post-Proteinase K digestion (FIG. 12). Additionally, RNA produced was assessed for Poly(A) integrity and RNA integrity by digital droplet polymerase chain reaction (ddPCR). Increasing CTP resulted in increased poly(A) and RNA integrity of the produced RNA (FIG. 13). FIG. 14 shows yield increases over the control for the +10% and +20% ATP comprising IVT reaction mixtures and an increase from the +10 and +20% ATP comprising IVT reaction mixtures. ATP levels were above the limit of quantification for the +20% ATP comprising IVT reaction mixtures, while ATP levels were at or below the limit of quantification for the control and +10% ATP comprising IVT reaction mixtures (FIG. 14).

Figure 15:
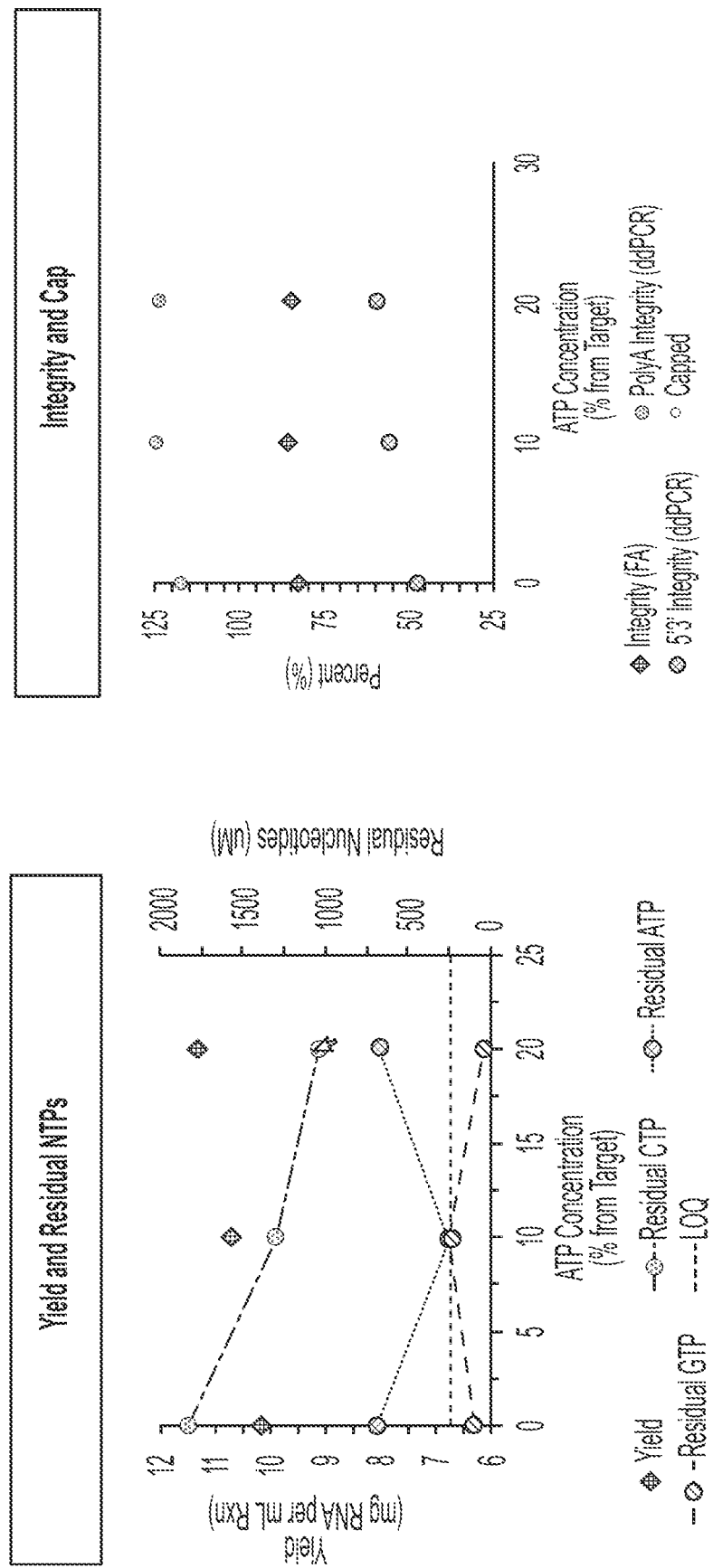
FIG. 15 shows additional exemplary studies demonstrating RNA integrity and percent capping as well as yield and residual CTP levels from exemplary IVT reactions utilizing IVT reaction mixtures comprising either +50% CTP volume and +10% ATP volume or +50% CTP volume and +20% ATP volume relative to a control IVT reaction mixing comprising +50% CTP volume and +0% ATP volume. When CTP was +50%, increasing ATP to +10% increased yield and integrity, but ATP was still depleted or nearly depleted. When CTP was +50%, increasing ATP to +20% further increases yield, but no significant improvement in integrity was observed and GTP became depleted.

Additional studies further demonstrated that an increase in starting ATP concentration (+10% ATP, +20% ATP relative to control) in addition to increasing starting CTP concentration (+50% CTP relative to control) in an exemplary IVT reaction mixture resulted in increases in yield, integrity, and capping at +10% ATP, but ATP is still depleted or nearly depleted. +20% ATP IVT reaction mixtures demonstrated further increases in yield, but no significant improvement in integrity or capping and GTP becomes depleted (FIG. 15).

Example 4: Additional Exemplary Assessment of IVT Reaction Mixtures

The present example demonstrates additional exemplary assessment of IVT reactions mixtures. FIG. 16 summarizes exemplary IVT reaction mixtures assessed and exemplary characterization of produced RNAs when CTP in the IVT reaction mixture is increased. Both RNA yield and integrity increased with higher CTP starting concentrations, while dsRNA content decreases with higher CTP concentration. Residual DNA was increased with higher CTP starting concentration (FIG. 16). Without wishing to be bound by any one theory, residual DNA may have increased with higher CTP starting concentration due to activity of DNAse I being decreased from, for example, lower free magnesium cation levels.

Positive effect(s) of additional CTP cannot only be caused by circumventing its limitation. Elevation of other NTP levels (e.g., ATP) could increase IVT performance further. Without wishing to be bound by any one theory, additional ATP could reduce "free" $Mg2+$ ions and benefit transcription of the polyA tail, resulting in improved transcription termination", potentially reducing the dsRNA formation further. Enrichment of CTP and/or ATP in the IVT reaction mixture with 40 mM MgAc is only possible to this extend, because we feed GTP and UTP and with keep the overall NTP concentration low enough the enrichment of ATP and CTP does not harm the IVT performance.

The exemplary IVT was performed in presence of a DNA template (linearized plasmid), $m2^{7,3'-O}Gppp(m^{2'-O})ApG$ (CC413) cap analog (1.5 mM) for co-transcriptional capping and the nucleoside triphosphates GTP and m1ΨFTP at the final concentration of 9 mM each. The starting CTP and ATP concentration was 9 mM (Standard/control) and 13.5 mM (+50%). Elevated CTP and ATP concentration were tested alone and in combination.

RNA was in vitro transcribed, purified and analyzed as described in Example 2.

Figure 17:
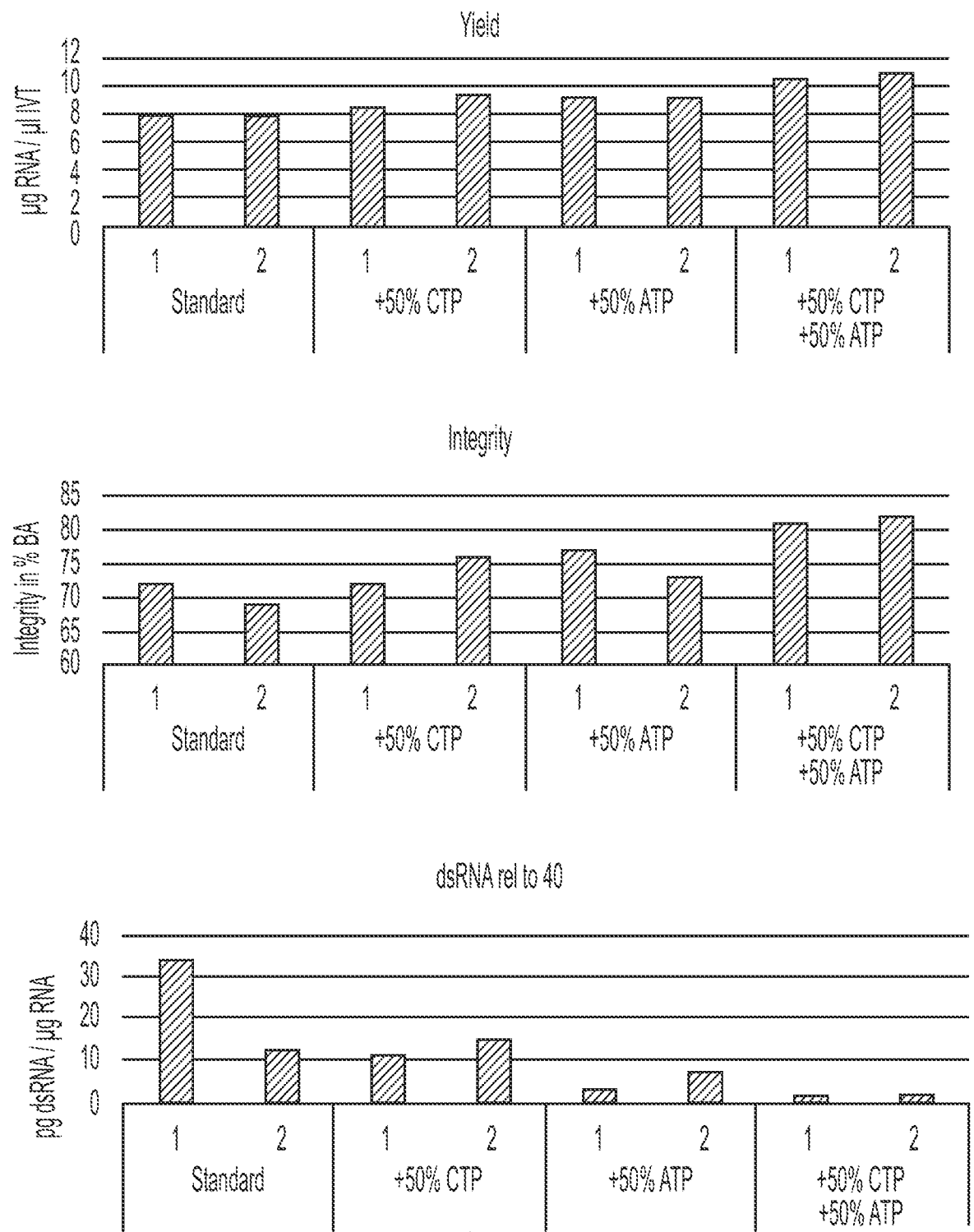
FIG. 17 shows additional exemplary studies of yield (top), RNA integrity (middle), and dsRNA (bottom)). Exemplary IVT reactions utilized IVT reaction mixtures comprising either +50% CTP volume, +50% ATP volume, or +50% CTP volume and +50% ATP volume relative to a control reaction mixture (+0% CTP volume, +0% ATP volume).

Enrichment of CTP levels in the IVT reaction mixtures enhanced produced RNA yield (FIG. 17A). Without wishing to be bound by any one theory, we propose that, in these reactions, reduction of CTP as the reaction progressed reached a point that less RNA could be produced. Increasing the CTP starting concentration circumvented this effect. An analogous effect was seen for the integrity. Here, limiting CTP levels reduced integrity, most likely through non-finished RNA transcripts. Again, this effect was rescued by elevation of CTP levels (FIG. 17B) As an additional positive effect, increasing the CTP starting concentration reduced the dsRNA formation (FIG. 17C).

Among other things, the present disclosure provides an insight that increasing CTP starting concentration may be beneficial independent of CTP representation in a produced transcript. For example, without wishing to be bound by any particular theory, it is proposed that reduction in dsRNA formation may be observed independent of level of CTP in the transcript. Alternatively or additionally, in some embodiments, elevated CTP may improve integrity independent of CTP representation in a produced transcript. Regardless, the present disclosure teaches that increasing CTP to levels above that at which it is represented in a produced transcript, in many embodiments, does no harm in an in vitro transcription reaction so that, among other things, in some embodiments, the present disclosure provide IVT reaction conditions (e.g., reaction mixture NTP concentrations useful therein) that may be generally, or even universally applied, to production of a variety of transcripts—e.g., of different lengths and/or different nucleotide compositions.

Figure 19:
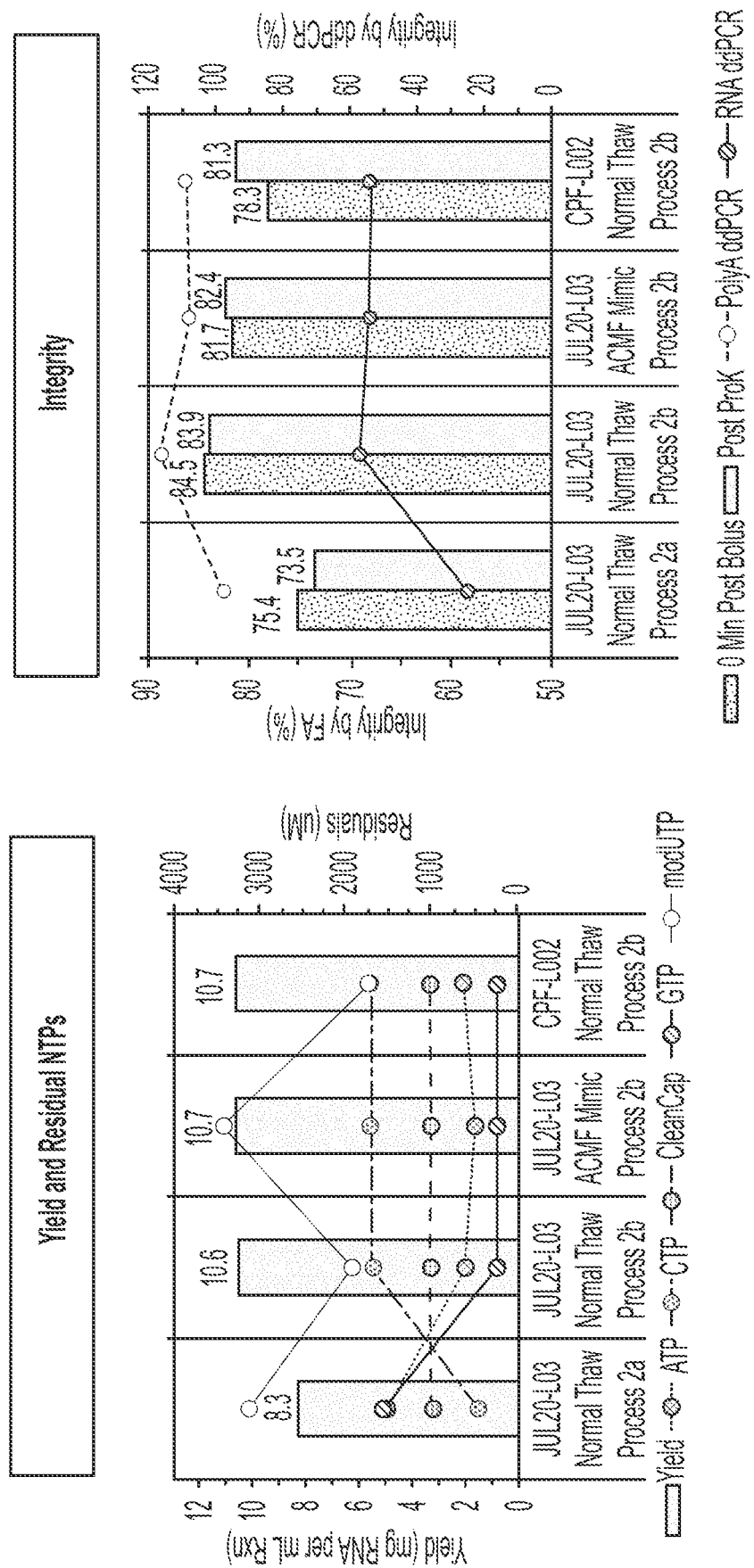
FIG. 19 shows exemplary assessment of yield, residual NTPs, and integrity of exemplary IVT reactions utilizing reaction mixtures comprising either +50% CTP and +20% ATP (Process 2b) or a standard/control (e.g., 1:1:1:1, e.g., 9 mM each) reaction mixture (process 2a).

FIG. 18 summarizes exemplary IVT reaction mixtures assessed and exemplary characterization of produced RNAs when CTP and/or ATP in the IVT reaction mixture was increased. It was further confirmed that IVT reaction mixtures produced a higher RNA yield and higher RNA integrity with +50% CTP and +20% ATP (FIGS. 18 and 19). Yield, integrity, and residual NTPs were stable as ATP volume was increased. Levels of ATP, CTP, GTP, and modUTP were above the limit of quantification and above stable with increasing amounts of ATP (FIG. 19).

FIG. 20 shows exemplary assessment of yield, integrity, and residual dsRNA content of exemplary IVT reactions utilizing reaction mixtures comprising either +25% ATP and +7% CTP, −21% ATP and −37% CTP, +25% ATP, or +7% CTP relative to control.

Additional transcripts (e.g., non-BNT162b1 and BNT162b2) were evaluated with varying nucleotide content. Additional ATP and/or CTP were added to reaction mixtures in exemplary IVT reactions to produce the transcripts. Relative to control reaction mixtures comprising 13.5 mM, 10.8 mM ATP, 9 mM GTP, and 9 mM UTP, either of +50% ATP or +50% ATP and +20% CTP were utilized. Nucleotide content of additional transcripts and exemplary reaction mixtures are shown in Table 4.1.

TABLE 4.1

Exemplary reaction mixtures to produce transcripts with varying nucleotide content.

| | Length | A (%) | G (%) | C (%) | U (%) | Standard NTP | Tested 1 | Tested 2 | |
|---|---|---|---|---|---|---|---|---|---|
| Transcript 1 | 3056 | 33 | 22 | 20 | 25 | 9/9/9/9 | 13.5/9/9/9 | 13.5/9/10.8/9 | (A/G/C/U) |
| Transcript 2 | 2000 | 32 | 21 | 19 | 27 | 9/9/9/9 | 13.5/9/9/9 | 13.5/9/10.8/10 | (A/G/C/U) |
| Transcript 3 | 2243 | 33 | 21 | 20 | 26 | 9/9/9/9 | 13.5/9/9/9 | 13.5/9/10.8/12 | (A/G/C/U) |

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims.

---

We claim:

1. A method of producing a ribonucleic acid (RNA) molecule through in vitro transcription, the method comprising creating a reaction mixture under reaction conditions to form the RNA molecule, the reaction mixture comprising a nucleic acid polymerase, a nucleic acid template, and:
   a molar ratio a of total cytidine triphosphate (CTP) and/or one or more CTP analog(s) to total guanosine triphosphate (GTP) and/or one or more GTP analog(s); and/or
   a molar ratio b of total CTP and/or one or more CTP analog(s) to total uridine triphosphate (UTP) and/or one or more UTP analog(s); and/or
   a molar ratio c of total CTP and/or one or more CTP analog(s) to total adenosine triphosphate (ATP) and/or one or more ATP analog(s),
   wherein:
   a is at least 1.25; and/or
   b is at least 1.25; and/or
   c is at least 1.10,
   so that the molar ratio of total CTP to GTP to UTP to ATP is not 1:1:1:1, and further wherein;
   the method is independent of the sequence of the RNA molecule.

2. The method of claim 1, wherein a is at least 1.30, 1.35, 1.40, 1.45, 1.50, 1.55, 1.60, 1.65, 1.70, 1.75, or 1.8.

3. The method of claim 1, wherein b is at least 1.30, 1.35, 1.40, 1.45, 1.50, 1.55, 1.60, 1.65, 1.70, 1.75, or 1.8.

4. The method of claim 1, wherein c is at least 1.15, 1.20, 1.25, 1.30, 1.35, 1.40, 1.45, or 1.50.

5. The method of claim 1, further comprising combining into the reaction mixture:
   a molar ratio d of total ATP and/or one or more ATP analog(s) to total GTP and/or one or more GTP analog(s); and/or
   a molar ratio e of total ATP and/or one or more ATP analog(s) to total UTP and/or one or more UTP analog(s),
   wherein:
   d is at least 1.10; and/or
   e is at least 1.10.

6. The method of claim 5, wherein d is at least 1.15, 1.20, 1.25, 1.30, 1.35, 1.40, 1.45, or 1.50.

7. A method of producing a ribonucleic acid (RNA) molecule through in vitro transcription, the method comprising creating a reaction mixture under reaction conditions to form the RNA molecule, the reaction mixture comprising a nucleic acid polymerase, a nucleic acid template, and:
   a molar ratio a of total cytidine triphosphate (CTP) and/or one or more CTP analog(s) to total guanosine triphosphate (GTP) and/or one or more GTP analog(s); and/or
   a molar ratio b of total CTP and/or one or more CTP analog(s) to total uridine triphosphate (UTP) and/or one or more UTP analog(s); and/or
   a molar ratio c of total CTP and/or one or more CTP analog(s) to total adenosine triphosphate (ATP) and/or one or more ATP analog(s); and/or
   a molar ratio d of total ATP and/or one or more ATP analog(s) to total GTP and/or one or more GTP analog(s); and/or
   a molar ratio e of total ATP and/or one or more ATP analog(s) to total UTP and/or one or more UTP analog(s),
   wherein:
   a is at least 1.25; and/or
   b is at least 1.25; and/or
   c is at least 1.10, and/or
   d is at least 1.10, and/or
   e is at least 1.15, 1.20, 1.25, 1.30, 1.35, 1.40, 1.45, or 1.50.

8. The method of claim 1, wherein a portion or all of the total CTP, GTP, UTP, or ATP and/or one or more CTP, GTP, UTP, or ATP analog(s) is added to the reaction mixture before transcription begins and/or at a start of transcription and a remaining portion of the total CTP, GTP, UTP, or ATP and/or one or more CTP, GTP, UTP, or ATP analog(s) is added to the reaction mixture after the start of transcription.

9. The method of claim 1, wherein the RNA molecule is single-stranded.

10. The method of claim 1, wherein the nucleic acid template is a DNA template.

11. The method of claim 1, wherein the reaction mixture further comprises one or more of a reaction buffer, an RNase inhibitor, a pyrophosphatase, one or more salts, a reducing agent, and spermidine.

12. The method of claim 1, wherein RNA integrity of RNA molecules produced by the method is at least about 40%, 45%, 50%, 55%, 60%, 65%, 70%, 75%, 80%, 85%, 90%, or 95%.

13. The method of claim 1, wherein RNA integrity of RNA molecules produced by the method is increased at least about 1%, 2%, 3%, 4%, 5%, 6%, 7%, 8%, 9%, 10%, 11%, 12%, 13%, 14%, 15%, 16%, 17%, 18%, 19%, or 20% compared to in vitro transcription in a reaction mixture in which a is not at least 1.25, b is not at least 1.25, and/or c is not at least 1.10.

14. The method of claim 1, wherein the concentration of RNA molecules produced by the method is at least about 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 11 mg/mL, 12 mg/mL, 13 mg/mL, 14, mg/mL, or 15 mg/mL.

15. The method claim 1, wherein residual dsRNA during and/or after transcription of RNA molecules produced by the method is at least about 25 pg dsRNA/µg RNA, 50 pg dsRNA/µg RNA, 75 pg dsRNA/µg RNA, 100 pg dsRNA/µg RNA, 125 pg dsRNA/µg RNA, 150 pg dsRNA/µg RNA, 175 pg dsRNA/µg RNA, 200 pg dsRNA/µg RNA, 225 pg dsRNA/µg RNA, 250 pg dsRNA/µg RNA, 275 pg dsRNA/µg RNA, or 300 pg dsRNA/µg RNA.

16. The method of claim 1, wherein residual dsRNA during and/or after transcription of RNA molecules produced by the method is decreased at least about 60%, 61%, 62%, 63%, 64%, 65%, 66%, 67%, 68%, 69%, 70%, 71%, 72%, 73%, 74%, 75%, 76%, 77%, 78%, 79%, or 80% compared to in vitro transcription in a reaction mixture in which a is not at least 1.25, b is not at least 1.25, and/or c is not at least 1.10.

17. The method of claim 1, wherein at least about 40%, 50%, 60%, 70%, 80%, 90%, or 99% of the RNA molecules produced by the method are capped.

18. The method of claim 1, wherein the RNA is a therapeutic RNA.

* * * * *